US012358950B2

(12) United States Patent
Allegretti et al.

(10) Patent No.: US 12,358,950 B2
(45) Date of Patent: *Jul. 15, 2025

(54) IL-17A BINDING PEPTIDES AND MEDICAL USES THEREOF

(71) Applicant: Dompe' Farmaceutici S.P.A., Milan (IT)

(72) Inventors: Marcello Allegretti, L'Aquila (IT); Andrea Aramini, L'Aquila (IT); Andrea Beccari, L'Aquila (IT); Marica Gemei, Naples (IT); Flavio Mantelli, L'Aquila (IT)

(73) Assignee: Dompe' Farmaceutici S.P.A., Milan (IT)

( * ) Notice: Subject to any disclaimer, the term of this patent is extended or adjusted under 35 U.S.C. 154(b) by 512 days.

This patent is subject to a terminal disclaimer.

(21) Appl. No.: 17/555,154

(22) Filed: Dec. 17, 2021

(65) Prior Publication Data

US 2022/0112244 A1     Apr. 14, 2022

Related U.S. Application Data

(60) Division of application No. 17/158,728, filed on Jan. 26, 2021, now Pat. No. 11,236,129, which is a continuation of application No. PCT/EP2019/070265, filed on Jul. 26, 2019.

(30) Foreign Application Priority Data

Jul. 27, 2018   (EP) .................................... 18186029

(51) Int. Cl.
  *C07K 7/08*      (2006.01)
  *A61K 38/00*     (2006.01)

(52) U.S. Cl.
  CPC ............... *C07K 7/08* (2013.01); *A61K 38/00* (2013.01)

(58) Field of Classification Search
  CPC ...... C07K 7/08; C07K 2319/00; A61K 38/00; A61K 38/04; A61P 11/06; A61P 19/02
  See application file for complete search history.

(56) References Cited

U.S. PATENT DOCUMENTS

| | | | |
|---|---|---|---|
| 6,515,173 | B1 | 2/2003 | Ternansky et al. |
| 11,236,129 | B2* | 2/2022 | Allegretti .................. C07K 7/08 |
| 2007/0249533 | A1 | 10/2007 | Levin et al. |
| 2012/0308566 | A1 | 12/2012 | Martin et al. |
| 2014/0357512 | A1* | 12/2014 | Yang .................. G01N 33/5011 435/7.1 |
| 2021/0300969 | A1 | 9/2021 | Allegretti et al. |

FOREIGN PATENT DOCUMENTS

| | | |
|---|---|---|
| CN | 106573964 | 4/2017 |
| WO | WO 2011/046958 | 4/2011 |

OTHER PUBLICATIONS

Caro-Quintero et al. Genome Sequencing of Five Shewanella baltica Strains Recovered from the Oxic-Anoxic Interface of the Baltic Sea. J Bacteriology, Genome announcement, 1 page (Year: 2012).*
Arican et al., "Serum Levels of TNF-α, IFN-γ, IL-6, IL-8, IL-12, IL-17, and IL-18 in Patients With Active Psoriasis and Correlation With Disease Severity," Mediators of Inflammation, 2005, 5:273-279.
Chauhan et al., "Autoimmunity in dry eye is due to resistance of Th17 to Treg Suppression," The Journal of Immunology, 2009, 182:1247-1252.
Chauhan et al., "Role of Th17 cells in the immunopathogenesis of dry eye disease," Mucosal Immunology, Jul. 2009, 2(4):375-376.
De Paiva et al., "Chapter 17: New understandings on pathogenesis of dry eye—From animal models to clinical therapy," Ophthalmology—Current Clinical and Research Updates, 2014, 415-441.
De Paiva et al., "IL-17 disrupts corneal barrier following desiccating stress," Mucosal Immunology, May 2009, 2(3):243-253.
Espada et al., "A Binding Site on IL-17A for Inhibitory Macrocycles Revealed by Hydrogen/Deuterium Exchange Mass Spectrometry," Journal of Medicinal Chemistry, Feb. 6, 2016, 59(5):2255-2260.
Fujino et al., "Increased expression of interleukin 17 in inflammatory bowel disease," Gut, Jan. 1, 2003, 52:65-70.
Garbutcheon-Singh KB et al., "A review of the cytokine IL-17 in ocular surface disease," Current Eye Research, Sep. 19, 2018, 44(1): 26 pages.
Goepfert et al., "The human IL-17A/F heterodimer: a two-faced cytokine with unique receptor recognition properties," Science Reports, Aug. 21, 2017, 7(8906): 13 pages.
Gu et al., "IL-17 family: Cytokines, receptors and signaling," Cytokine, Sep. 3, 2013, 64(2):477-485.
Hah et al., "Ascorbis acid conentraitons in aqueous humor after systemic vitamin C supplementation in patients with cataract: pilot study," BMC Ophthalmology, Jul. 11, 2017, 17(121):1-5.
Krueger et al., "IL-17A is essential for cell activation and inflammatory gene circuits in subjects with psoriasis," The Journal of Allergy and Clinical Immunology, Jun. 7, 2012, 130(1):145-154.
Lai et al., "Epitope Targeted Macrocyclic Peptide Ligand with Picomolar Cooperative Bin-ding to Interleukin-17F," Chemsitry, Jan. 10, 2018, 24(15):3760-3767.
Liu et al., "Binding site elucidation and structure guided design of macrocyclic IL-17A antagonists," Scientific Reports, Aug. 16, 2016, 6(30859): 12 pages.
Liu et al., "Crystal structures of interleukin 17A and its complex with IL-17 receptor A," Nature Communications, May 21, 2013, 4:1888, 9 pages.
Liu et al., "Inhibiting complex IL-17A and IL-17RA interactions with a linear peptide," Scientific Reports, May 17, 2016, 6(26071): 11 pages.

(Continued)

Primary Examiner — Sudhakar Katakam
(74) Attorney, Agent, or Firm — Fish & Richardson P.C.

(57) ABSTRACT

The invention relates to IL-17A binding peptides, inhibitors of the interaction of IL-17A with the receptor IL-17RA, and to bioconjugates, dimers, pharmaceutical compositions and medical use thereof.

10 Claims, 10 Drawing Sheets

Specification includes a Sequence Listing.

(56) References Cited

OTHER PUBLICATIONS

Lubberts et al., "Treatment with a neutralizing anti☐murine interleukin☐17 antibody after the onset of collagen☐induced arthritis reduces joint inflammation, cartilage destruction, and bone erosion," Arthritis & Rheumatology, Feb. 5, 2004, 50(2):650-659.

Murcia et al., "The Interleukin-17 Induced Activation and Increased Survival of Equine Neutrophils Is Insensitive to Glucocorticoids," PLOS ONE, May 3, 2016, 11(5):e0154755, 14 pages.

Onishi et al., "Interleukin-17 and its target genes: mechanisms of interleukin-17 function in disease," Immunology, Feb. 2, 2010, 129(3):311-321.

PCT International Search Report and Written Opinion in International Appln. No. PCT/EP2019/070265, dated Sep. 10, 2019, 16 pages.

Ronkko et al., "Human corneal cell culture models for drug toxicity studies," Drug Delivery and Translational Research, Sep. 9, 2016, 6:660-675.

Shabgah et al., "Interleukin-17 in human inflammatory diseases," Postepy Dermatol Allergol, 2014, 31(4):256-261.

Singh et al., "Ocular adverse effects if antu-cancer chemotherapy and targeted therapy," Journal of Cancer Therapeuctics & Research, 2012, 1-7.

Snirivasan et al., "TEER measurement techniques for in vitro barrier model systems," Journal of Laboratory Automation, Jan. 13, 2015, 20(2):107-126.

Stern et al., "Autoimmunity at the ocular surface: pathogenesis and regulation," Mucosal Immunology, Sep. 2010, 3(5):425-442.

Stevenson et al., "Dry Eye Disease," Arch Ophthalmol, Jan. 2012, 130(1):90-100.

Subbarayal et al., "IL-17 Augments Biomolecules Cell Activation in Ocular Surface Autoimmunity," The Journal of Immunology, Sep. 21, 2016, 197:3464-3470.

Sugrue et al., "ZO1 in Corneal Epithelium : Association to the Zonula Occludens and Adherens Junctions," Experimental Eye Research, Jan. 1997, 64(1):11-20.

Takahashi et al., "Serum cytokines and growth factor levels in Japanese patients with psoriasis," Clinical Experimental Dermatology, Jul. 2, 2010, 35(6):645-649.

Ting et al., "Utilization of peptide phage display to investigate hotspots on IL-17A and what it means for drug discovery," PLoS One, Jan. 12, 2018, 13(1): e0190850, 11 pages.

Xiang et al., "Characterization of human corneal epithelial cell model as a surrogate for corneal permeability assessment: Metabolism and transport," Drug Metabolism and Disposition, 2009, 37(5):992-998.

Xu et al., "Interleukin-17 and its expanding biological functions," Cellular & Molecular Immunology, Apr. 12, 2010, 7:164-174.

Zeichner et al., "The Role of IL-17 in the Pathogenesis and Treatment of Psoriasis," Journal of Clinical and Aesthetic Dermatology, Jun. 2016, 9(6 Suppl 1):S3-S6.

Zhong et al., "Pyroglutamate and O-Linked Glycan Determine Functional Production of Anti-IL17A and Anti-IL22 Peptide-Antibody Bispecific Genetic Fusions," The Journal of Biological Chemistry, Jan. 11, 2013, 288(2):1409-1419.

Anonymous, "User Manual: PathHunter IL17RA/IL17RC Dimerization Bioassay Kit, for Chemiluminescent Detection of IL 17RA/IL17RC Dimerization," Eurofins, DiscoverX, available on or before Dec. 6, 2023, retrieved from URL<chrome-extension://efaidnbmnnnibpcajpcglclefindmkaj/https://www.discoverx.com/content/uploads/2023/07/70-402-PathHunter-IL17RA_IL17RC-Dimerization-Bioassay-Kit_REV0-1.pdf>, 11 pages.

CN Office Action in Chinese Appln. No. 201980050055.4, dated Dec. 6, 2023, 14 pages (with English translation).

\* cited by examiner

IL-17A BINDING PEPTIDES AND MEDICAL USES THEREOF

CROSS-REFERENCE TO RELATED APPLICATIONS

This application is a divisional of U.S. patent application Ser. No. 17/158,728, filed Jan. 26, 2021, which is a continuation and claims the benefit of PCT Application No. PCT/EP2019/070265, filed Jul. 26, 2019, which claims benefit of European Patent Application No. 18186029.7, filed Jul. 27, 2018, all of which are incorporated by reference herein in their entirety.

REFERENCE TO SEQUENCING LISTING FILED ON EFS-WEB

The instant application contains a sequence listing which has been submitted electronically in ASCII format and is hereby incorporated by reference in its entirety. Said ASCII copy, created on Jun. 17, 2021, is named "Sequence_Listing.txt" and is 50,167 bytes in size.

The present invention relates to IL-17A binding peptides, inhibitors of the binding of IL-17A to the IL-17AR receptor and thereby of the formation of the complex IL-17A/IL-17RA/IL17RC. Object of the invention are also bioconjugates and dimers comprising the above peptides, pharmaceutical compositions and medical uses of the above peptides, bioconjugates and dimers.

BACKGROUND OF THE INVENTION

Human cytotoxic T lymphocyte-associated antigen 8 (CTLA8), named also Interleukin 17 (IL-17), was first cloned in 1993. The first biological activity described for human IL-17 was the induction of the production of Interleukin 6 (IL-6) and Interleukin 8 (IL-8) from rheumatoid arthritis synoviocytes. This finding suggested a role for IL-17 in inflammation through IL-6, and in neutrophil recruitment through IL-8 Xu S et al, Cell Mol Immunol. 2010, 164-74; Murcia R Y et al, PLOS ONE 2016, 11(5): e0154755doi:10.1371/journal.pone.0154755).

It was later found that this molecule, later named IL-17A, is part of a larger family which includes five additional members, namely IL-17B to F. IL-17F shares the greatest homology (about 56%) with the first discovered IL-17, IL-17A, while IL-17E displays the lowest sequence conservation (about 16%). The members of IL-17 family exert their functions binding to their receptors in the form of homodimers, with the exception of IL-17A and IL-17F which may also act as heterodimers (Goepfert A et al, Sci Rep, 2017, 7 (1), 8906).

The most widely investigated cytokine of this family, IL-17A, plays an essential role in host defense against microbial infections and it is considered the major driver for a number of inflammatory and autoimmune conditions. Pathological production of IL-17A leads to excessive inflammation and evident tissue damage.

In particular, through induction of a variety of molecules including cytokines, chemokines, acute phase proteins, antimicrobial peptides, mucins, and matrix metalloproteinases, IL-17A can amplify cascades of events that lead to neutrophil recruitment, inflammation and host defense. Although IL-17A is the signature cytokine produced by T helper 17 (Th17) cells, IL-17A, as other IL-17 family cytokines, has multiple sources ranging from immune cells to nonimmune cells.

IL-17B, IL-17C, and IL-17D are also considered pro-inflammatory cytokines but their role is not fully known. IL-17E, also known as IL-25, has the lowest homology and is involved in Th2 cell responses against parasites and allergy. CCL20 drives the recruitment of Th17 and dendritic cells to the inflammatory site. In turn, Th17 cells are activated thus producing inflammatory mediators and leading to chronic inflammation.

The cytokines belonging to IL-17 family signal via their related receptors and activate downstream pathways that include NFκB, MAPKs and C/EBPs to induce the expression of antimicrobial peptides, cytokines and chemokines. The proximal adaptor Act1 is a common mediator during the signaling of all IL-17 cytokines, and it is involved in IL-17-mediated host defense and in IL-17-driven autoimmune conditions.

The IL-17 receptor family consists of five members, IL-17RA, RB, RC, RD and RE, all of which, like their ligands, share sequence homology.

IL-17RA is ubiquitously expressed on a wide range of tissues and cell types and binds to IL-17-A, C, E and F. Receptor signaling occurs through heterodimeric receptors formed of a common IL17-RA subunit and a second subunit that depends on the ligand and regulates signaling specificity. Upon stimulation with the ligand, IL-17RA forms a heterodimeric receptor complex with IL-17RB (for IL-17E), IL-17RC (for IL-17A and IL-17F) or IL-17RE (for IL-17C). It is proposed that the binding of ligand to the first IL-17RA receptor subunit promotes the second binding event, thus inducing the formation of a heterodimeric receptor complex. In particular, the signal of IL-17A and IL-17F is mediated by the complex between IL-17RA and IL-17RC. IL-17F binds to IL-17RA with about 100 to 1000 times lower affinity than IL-17A, while the binding affinity for IL-17RC is comparable between the two cytokines (Onishi R M et al, Immunology 2010, 129(3), 311-321; Gu C et al. Cytokine 2013, 64(2), 477-485).

IL-17A in humans plays a pivotal role in various autoimmune and inflammatory conditions, such as rheumatoid arthritis, multiple sclerosis, psoriasis, Crohn's disease, systemic lupus erythematosus, asthma, Behçet's disease, and hyper IgE syndrome (Fujino S et al Gut. 2003, 52, 65.70; Shabgah A G et al, Postepy Dermatol Allergol 2014, 31 (4), 256-261). Furthermore, IL-17A blockade has shown preclinical and clinical efficacy in ankylosing spondylitis and rheumatoid arthritis (Liu S et al, Nature-Scientific Reports 2016, doi:10.1038/srep26071; Lubberts E et al, Arthritis Rheum 2004, 50, 650-659).

Also, IL-17A has been shown to be involved in ocular diseases, and in particular in the pathogenesis of ocular surface and corneal diseases, such as dry eye disease (DED), viral and bacterial keratitis. Antibodies developed to neutralize IL-17A have shown promising results in reducing the severity of these diseases (Garbutcheon-Singh K B et al, Curr Eye Res, 2018, DOI:10.1080/02713683.2018.1519834).

DED is an inflammatory and autoimmune ophthalmic disease of the tear system and ocular surface that results in discomfort, visual disturbance and tear film impairment. DED is one of the most common cause of acquired visual impairment in adult population (Stern M E et al, Mucosal Immunol 2010. 3(5), 425-442; Stevenson W et al, Arch Ophthalmol 2012, 130(1), 90-100, Parul Singh, Parul Singh 2012, Hah, Chung et al. 2017). The disease involves an immune and inflammatory process that affects the ocular surface and, in severe cases, may lead to blindness. Current treatment of DED is mainly symptomatic, consisting in ocular lubricants and non-specific anti-inflammatory agents such as corticosteroids, cyclosporine A, and tacrolimus. IL-17A is associated with damage to the corneal epithelial barrier function, which is the most sight threatening complication of DED. An increase in Th17 cells is reported in DED patient ocular tissues that induces an increase in IL-6, TGF-β, IL-23 and IL-17A concentrations on the ocular surface, as well as increased concentration of IL-17 in tears, and number of Th17 cells on the ocular surface of experimental DED models. In addition, it has also been demonstrated that in vivo neutralization of IL-17A results in a markedly attenuated induction and severity of disease (De Paiva C S et al. Mucosal Immunol. 2009; 2(3): 243-253, Chauhan et al. Mucosal Immunol, 2009, 2(3), 243-253; Chauhan S K et al, Mucosal Immunol 2009, 2(4), 375-376; Chauhan, El Annan et al. 2009, De Paiva, Chotikavanich et al. 2009, de Paiva. Huang et al. 2014, Subbarayal, Chauhan et al. 2016).

IL-17A has also been implicated in psoriasis. Psoriasis is a chronic inflammatory disease. It manifests itself as dry, raised, red skin lesions (plaques) covered with silvery scales. Numerous clinical phenotypes exist (i.e. plaque, guttate, pustular, inverse), with disease severity ranging from a few scattered plaques to extensive body surface involvement. Individuals with psoriasis have an increased risk of developing other chronic and serious diseases such as psoriatic arthritis, metabolic syndrome, cardiovascular diseases and depression. A central role of IL-17A in the pathophysiology of psoriasis has been demonstrated (Zeichner J A et al J Clin Aesthet Dermatol 2016, 9 (6 Suppl 1), S3-S6). In psoriasis, expression of IL-17 mRNA is higher in lesional compared with nonlesional skin. Additionally, IL-17A levels are significantly correlated to disease severity (Arican O et al. Mediators Inflamm 2005, 2005, 273-279, Takahashi K et al. Clin Exp Dermatol 2010, 35, 645-649). Blockade of IL-17A has been shown to reduce keratinocyte hyperproliferation, T-cell infiltration into the dermis, and mRNA expression of key disease-propagating genes (Krueger J G et al, J Allergy Clin Immunol 2012, 130, 145-154).

Anti-IL-17A antibodies secukinumab (AIN457, Consentyx™), a fully human IgG1k anti-IL-17A mAb, and ixekizumab (LY2439821), a humanized IgG4 antibody, were tested in clinical trials in psoriasis and approved for the treatment of moderate to severe psoriasis. During clinical trials, both antibodies were able to reduce the severity of the disease by at least 75% (PAS175) in 80% of the patient population. Moreover, current advanced clinical trials have shown promising results also for treatment of ankylosing spondylitis and psoriatic arthritis. Other antibodies are now in clinical trials for the same indications.

The above evidence strongly supports the development of molecules able to target IL-17A and inhibit its signaling for the treatment of the above pathologies. Until recently, targeting of IL17-A and its receptors has remained the domain of antibodies. The reason for the preference for antibodies is that cytokines, as IL-17A, constitute a protein-protein interaction (PPI) target difficult to target, so far considered undruggable. In fact, PPI interfaces are generally flat and lack deep subpockets and grooves that are usually necessary to bind Small Molecular Weight (SMW) molecules. Despite this, in recent years new research identified a few SMW IL-17A antagonists able to bind IL-17A and prevent its interaction with IL-17RA receptor, and thus inhibit IL-17A pathway activation (Espada A et al. J Med Chem 2016, 59(5), 2255-2260; Ting J P et al PLoS One 2018, 13(1), e0190850; Liu S et al, Scientific reports, 6:26071, doi: 10.1038/srep26071). Among these, a peptide of sequence IHVTIPADLWDWINK (SEQ ID NO: 1), which was named High Affinity Peptide (HAP) has been described (Liu S et al, Scientific reports, 6:26071, doi: 10.1038/srep26071).

However, there is still the need of identifying and characterizing new molecules able to bind with high affinity to IL-17A and prevent IL-17A pathway activation for the development of new therapeutic options for the treatment of disorders involving IL-17A/IL-17RA axis.

SUMMARY OF THE INVENTION

The present inventors have surprisingly found peptides able to bind to a specific site on the N-terminal portion of IL-17A and thereby to inhibit the interaction with IL-17RA and the formation of the IL-17A71L-17RA/IL17RC complex.

The inhibition of said interaction blocks the IL-17A signaling pathway. The peptides according to the invention are therefore able to reduce TH17-related inflammation and the subsequent damage observed in inflammatory and autoimmune diseases where these cells and IL-17A exert a pivotal role.

As will be shown in the experimental section, the peptides of the invention have physical-chemical properties that make them particularly suitable for topical treatment of ophthalmic and dermatological diseases.

Said peptides are useful to design innovative and specific topical treatment of diseases dependent on an excessive production or activity of IL-17A.

Objects of the present invention are peptides able to inhibit IL-17A binding to IL-17RA, dimers and bioconjugates, pharmaceutical compositions comprising said peptides, dimers or bioconjugates and the use of the above in the prevention and/or treatment of autoimmune and inflammatory diseases depending on IL-17A.

DEFINITIONS

Figure 1:
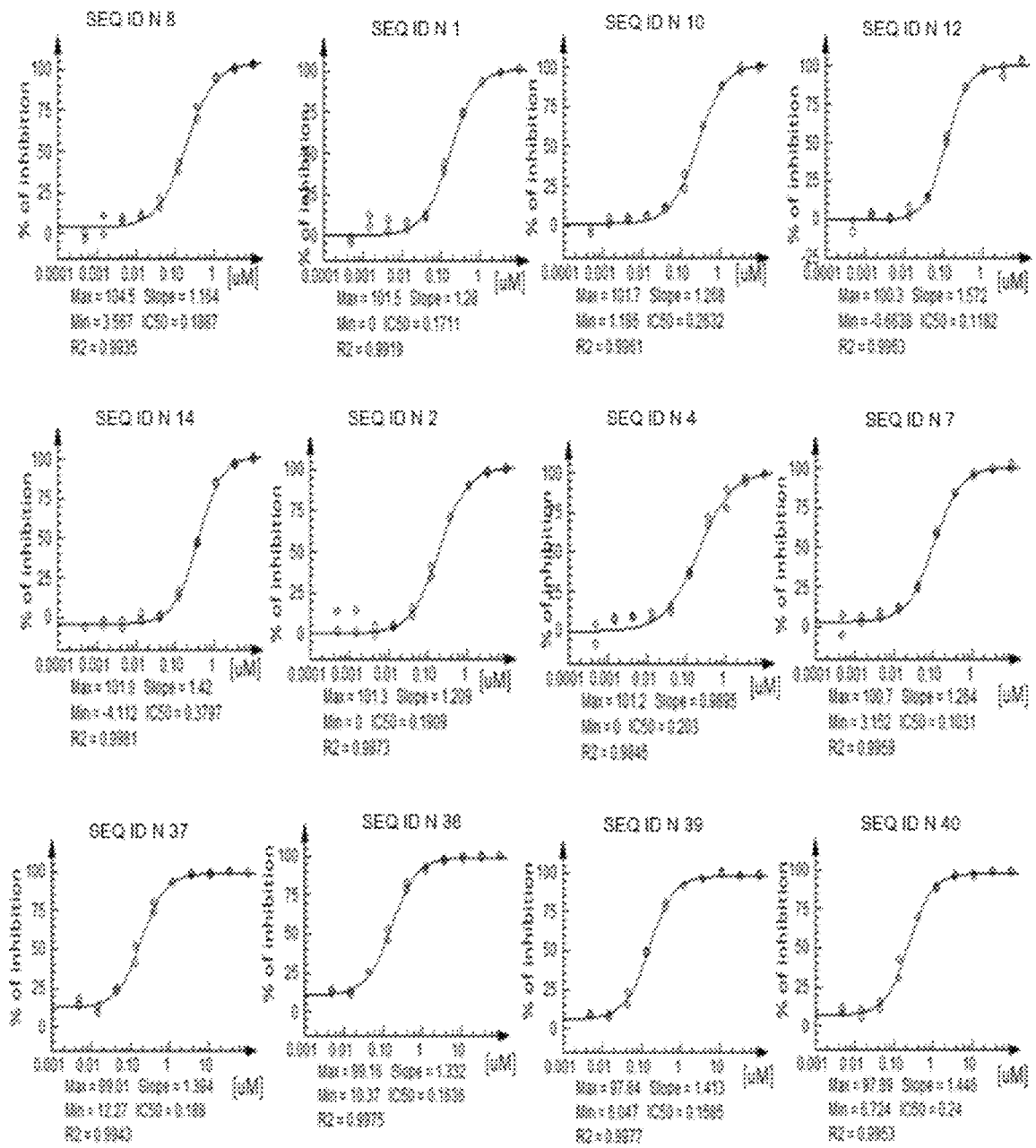
FIG. 1 shows some dose-response curves obtained in the IL-17RA-IL17RC dimerization assay described in Example 5 of with representative IL-17A binding peptides according to the invention. The percentage of inhibition of IL-17RA/IL17RC dimerization induced by IL-17A obtained by treatment with different peptides is reported.

Unless otherwise defined, all terms of art, notations and other scientific terminology used herein are intended to have the meanings commonly understood by those persons skilled in the art to which this disclosure pertains. In some cases, terms with commonly understood meanings are defined herein for clarity and/or for ready reference; thus, the inclusion of such definitions herein should not be construed to represent a substantial difference over what is generally understood in the art.

The term "pharmaceutically acceptable excipient" refer to substances other than the active pharmaceutical ingredient (API) that have been appropriately evaluated for safety and are intentionally included in a drug delivery system. Pharmaceutically acceptable excipients are well known in the prior art and are disclosed, for example in the Handbook of Pharmaceutical Excipients, seventh edition 2013, which is included here for reference (Rowe, Sheskey et al. 2012).

Excipients are normally classified according to the function that they have in the final pharmaceutical composition. Preferably, suitable excipients according to the present invention are for example diluent, adsorbent, glidant, binder, lubricant, surfactant, disintegrating, preservatives, antioxidant or mixtures thereof.

The terms "approximately" and "about" herein refers to the range of the experimental error, which may occur in a measurement.

The terms "comprising", "having", "including" and "containing" are to be construed open-ended terms (i.e. meaning "including, but not limited to") and are to be considered as providing support also for terms as "consist essentially of", "consisting essentially of", "consist of" or "consisting of".

The terms "consist essentially of". "consisting essentially of" are to be construed as semi-closed terms, meaning that no other ingredients which materially affects the basic and novel characteristics of the invention are included (optional excipients may thus be included).

The terms "consists of," "consisting of" are to be construed as closed terms.

The term "bioconjugate" as used herein refers to a conjugate formed by a stable covalent link between different molecules, preferably two molecules, optionally linked by means of a spacer, at least one of which is a biomolecule.

The term "biomolecule" as used herein refers to molecules of biological origin. The term includes macromolecules, such as carbohydrates, lipids and proteins or small natural products. For the purpose of the present invention "biomolecules" are preferably selected from ascorbic acid, capric acid, capronic acid, N-Acetyl-Glucosamine (also referred to as NAG), N-Acetylmuramic acid (also referred to as NAM), hyaluronic acid, alginic acid, chitin, $(GalNAc)_2$, Gal-alpha1,3-GalNAc or trigalacturonic acid.

The definition "conservative substitution" herein refers to a conservative replacement (also called a conservative mutation or a conservative substitution) is an amino acid replacement that changes a given amino acid to a different amino acid with similar biochemical properties (Simon French 1983).

DESCRIPTION OF THE INVENTION

The present inventors have identified a number of peptides that are able to bind with high affinity to IL-17A and inhibit its interaction with the ILRA receptor. These compounds act as inhibitors of IL-17A signaling.

Accordingly, a first object of the present invention is a peptide, able to inhibit IL-17A binding to ILRA, having the amino acid sequence of either:

formula (I):

(I)
(SEQ ID NO: 258)
$X_1-X_2-X_3-X_4-X_5-X_6-X_7-X_8-X_9-X_{10}-X_{11}-X_{12}-X_{13}-X_{14}-X_{15}$ wherein, independently from each other.
$X_1$ is I, V, D, K, W, A, G, L or P;
$X_2$ is H, M, K, N, R, E, Q, W or Y:
$X_3$ is V, F, A, G, L, P, I, Y or W;
$X_4$ is T, Q, H, S, N or Y;
$X_5$ is I, F, A, G, L, P, V or Y;
$X_6$ is P, G, A, L, V, I or N;
$X_7$ is A, Q, G, L, P, V, I, N or E;
$X_8$ is D, E, N, Q or Y;
$X_9$ is L, V, F, W, A, G, P, I or H;
$X_{10}$ is W, Y, F or Q or it is absent;
$X_{11}$ is D, E or N or it is absent;
$X_{12}$ is W, F, V, H or Y or it is absent;
$X_{13}$ is I, V, F, E, K, A, G, L, P or Y or its absent;
$X_{14}$ is N, R, E, F, Q or D or it is absent;
$X_{15}$ is K, R, E, F, V, W, H or D or it is absent;
with the proviso that said sequence is not IHVTIPADLWDWINK (SEQ ID NO: 1) or a 12-14 amino acid long C-terminal truncated sequence thereof IHVTIPADLWDWIN (SEQ ID NO: 259), IHVTIPADLWDWI (SEQ ID NO: 260), or IHVTIPADLWDW (SEQ ID NO: 261); or formula (II):

(II)
(an-SEQ ID NO: 41-bn')
$a_n$-DLSAVCWAFPWDPECH-$b_{n'}$.

wherein, independently from each other:
a, b are selected from A, R, N, D, C, E, Q, G, H, I, L, K, M, F, P, S, T, W, Y or V;
n=integer from 0 to 3;
n'=integer from 0 to 3.

Preferably, in formula (II) each of the aminoacids different from a or b can be replaced with a conservative substitution.

A preferred peptide of formula (II) is DLSAVCWAFPWDPECH (SEQ ID NO: 41).

Particularly preferred are the peptides of formula (I).

According to a preferred embodiment, in said peptide of formula (I):
- $X_1$ is I, V, D, K or W;
- $X_2$ is H, M, K or N;
- $X_3$ is V or F;
- $X_4$ is T, Q, H, V or Y;
- $X_5$ is I or F;
- $X_6$ is P or G;
- $X_7$ is A or Q;
- $X_8$ is D, E, N;
- $X_9$ is L, V, F or W;
- $X_{10}$ is W, Y, F or it is absent;
- $X_{11}$ is D, E, N or it is absent;
- $X_{12}$ is W, F, V or it is absent;
- $X_{13}$ is I, V, F or it is absent;
- $X_{14}$ is N, R, E, F or it is absent;
- $X_{15}$ is K, R, E, F, V, W or it is absent;
- with the proviso that said sequence is not IHVTIPADLWDWINK (SEQ ID NO: 1) or a 12-14 amino acid long C-terminal truncated sequence thereof IHVTIPADLWDWIN (SEQ ID NO: 259), IHVTIPADLWDWI (SEQ ID NO: 260), or IHVTIPADLWDW (SEQ ID NO: 261).

According to an alternative preferred embodiment, in said peptide of formula (I):
- $X_1$ is I, V, A, G, L, or P;
- $X_2$ is H, M, K, R, E, Q, W or Y;
- $X_3$ is V, F, A, G, L, P, I, Y or W;
- $X_4$ is T, Q, S, N or Y;
- $X_5$ is I, F, A, G, L, P, V or Y;
- $X_6$ is P, G, A, L, V, I or N;
- $X_7$ is A, Q, G, L, P, V, I, N or E;
- $X_8$ is D, E, N, Q or Y;
- $X_9$ is L, V, F, W, A, G, P, I or H;
- $X_{10}$ is W, Y, F or Q or it is absent;
- $X_{11}$ is D, E or N or it is absent;
- $X_{12}$ is W, F, H or Y or it is absent;
- $X_{13}$ is I, V, F, E, K, A, G, L, P or Y or its absent;
- $X_{14}$ is N, R, E, Q or D or it is absent;
- $X_{15}$ is K, R, E, V, W, H or D or it is absent;
- with the proviso that said sequence is not IHVTIPADLWDWINK (SEQ ID NO: 1) or a 12-14 amino acid long C-terminal truncated sequence thereof IHVTIPADLWDWIN (SEQ ID NO:259), IHVTIPADLWDWI (SEQ ID NO:260), or IHVTIPADLWDW (SEQ ID NO:261).

Preferably, in the above peptide of formula (I) all aminoacids $X_1$ to $X_{15}$ are present and the above described peptides of formula (I) have a 15 amino acid sequence. Preferably, in the peptides of formula (I) having a sequence of less than 15 aminoacids, when one amino acid is absent, also all aminoacids at the N terminal of said amino acid are absent. For example, if amino acid $X_{10}$ is absent, also aminoacids $X_{11}$ to $X_{15}$ are absent.

Particularly preferred peptides of formula (I) are those wherein $X_1$ is V.

A particular preferred peptide having $X_1$ as V is the peptide of SEQ ID NO: 2.

As will be demonstrated in the experimental section, the present inventors have found that the peptide of SEQ ID NO: 2, where the first amino acid Isoleucine in the peptide HAP of SEQ ID NO:1 has been replaced by a Valine, surprisingly shows strikingly different functional and chemical-physical properties as well as improved tolerability compared to HAP.

In particular, as demonstrated in the Examples, the peptide shows improved chemical-physical properties, that are particularly advantageous for topical and ophthalmic use, a better permeability and an increased affinity for IL-17A compared to the corresponding peptide of SEQ ID NO: 1. Also, the inventors have found that the peptide HAP, independently from its activity on IL-17A signaling, exerts a direct toxicity effect on corneal cells by inducing the expression of inflammatory cytokines. Surprisingly, the peptide of SEQ ID NO: 2 does not show this effect and therefore is characterized by an improved tolerability compared to HAP.

Preferably, in the above peptide of formula (I):
- $X_1$ is I, V or L;
- $X_2$ is H, M, R, K or E;
- $X_3$ is V, F or I;
- $X_4$ is T, Q, S, Y or N;
- $X_5$ is I, F or V;
- $X_6$ is P;
- $X_7$ is A, Q, or L;
- $X_8$ is D, E, or Q;
- $X_9$ is L, W, F, V or I;
- $X_{10}$ is W, Y or F;
- $X_{11}$ is D, E or N;
- $X_{12}$ is W or F;
- $X_{13}$ is I, V, F or L;
- $X_{14}$ is N, R, Q or E;
- $X_{15}$ is K, R, H or E;
- with the proviso that said sequence is not IHVTIPADLWDWINK (SEQ ID NO: 1);

or
- $X_1$ is I or V;
- $X_2$ is H, M or R,
- $X_3$ is V or F;
- $X_4$ is T or Q;
- $X_5$ is I, F or V;
- $X_6$ is P or G;
- $X_7$ is A or Q;
- $X_8$ is D or E;
- $X_9$ is L;
- $X_{10}$ is W or Y;
- $X_{11}$ is D or E;
- $X_{12}$ is W;
- $X_{13}$ is I or V;
- $X_{14}$ is N, R or E;
- $X_{15}$ is K, R or E;
- with the proviso that said sequence is not IHVTIPADLWDWINK (SEQ ID NO: 1):

or
- $X_1$ is I or V;
- $X_2$ is H or M,
- $X_3$ is V;
- $X_4$ is T;
- $X_5$ is I;
- $X_6$ is P;
- $X_7$ is A;
- $X_8$ is D;
- $X_9$ is L, W, F, V or I;
- $X_{10}$ is W or Y;
- $X_{11}$ is D or E;
- $X_{12}$ is W;
- $X_{13}$ is I or V;
- $X_{14}$ is N, R or E;
- $X_{15}$ is K, R or E;

with the proviso that said sequence is not IHVTI-PADLWDWINK (SEQ ID NO: 1);
or
$X_1$ is I, V, A, G, L, or P;
$X_2$ is M, K, R, E, Q, W or Y;
$X_3$ is V, F, A, G, L, P, I, Y or W;
$X_4$ is T, Q, S, N or Y;
$X_5$ is I, F, A, G, L, P, V or Y;
$X_6$ is P, G, A, L, V, I or N;
$X_7$ is A, Q, G, L, P, V, I, N or E;
$X_8$ is D, E, N, Q or Y;
$X_9$ is L, V, F, W, A, G, P, I or H;
$X_{10}$ is Y, F or Q;
$X_{11}$ is D, E or N;
$X_{12}$ is W, F, H or Y;
$X_{13}$ is I, V, F, E, K, A, G, L, P;
$X_{14}$ is N, R, E, Q or D;
$X_{15}$ is K, R, E, V, W, H or D;
or
$X_1$ is V, A, G, L, or P;
$X_2$ is H, M, K, R, E, Q, W or Y;
$X_3$ is V, F, A, G, L, P, I, Y or W;
$X_4$ is T, Q, S, N or Y;
$X_5$ is I, F, A, G, L, P, V or Y;
$X_6$ is P, G, A, L, V, I or N;
$X_7$ is A, Q, G, L, P, V, I, N or E;
$X_8$ is D, E, N, Q or Y;
$X_9$ is L, V, F, W, A, G, P, I or H;
$X_{10}$ is Y, F or Q;
$X_{11}$ is D, E or N;
$X_{12}$ is W, F, H or Y;
$X_{13}$ is I, V, F, E, K, A, G, L, P or Y;
$X_{14}$ is N, R, E, Q or D;
$X_{15}$ is K, R, E, V, W, H or D;
or
$X_1$ is V, A, G, L, or P;
$X_2$ is M, K, R, E, Q, W or Y;
$X_3$ is V, F, A, G, L, P, I, Y or W;
$X_4$ is T, Q, S, N or Y;
$X_5$ is I, F, A, G, L, P, V or Y;
$X_6$ is P, G, A, L, V, I or N;
$X_7$ is A, Q, G, L, P, V, I, N or E;
$X_8$ is D, E, N, Q or Y;
$X_9$ is L, V, F, W, A, G, P, I or H;
$X_{10}$ is Y, F or Q;
$X_{11}$ is D, E or N;
$X_{12}$ is W, F, H or Y;
$X_{13}$ is I, V, F, E, K, A, G, L, P or Y;
$X_{14}$ is N, R, E, Q or D;
$X_{15}$ is K, R, E, V, W, H or D;
or
$X_1$ is V, A, G, L, or P;
$X_2$ is H, M, K, R, E, Q, W or Y;
$X_3$ is V, F, A, G, L, P, I, Y or W;
$X_4$ is T, Q, S, N or Y;
$X_5$ is I, F, A, G, L, P, V or Y;
$X_6$ is P, G, A, L, V, I or N;
$X_7$ is A, Q, G, L, P, V, I, N or E;
$X_8$ is D, E, N, Q or Y;
$X_9$ is L, V, F, W, A, G, P, I or H;
$X_{10}$ is W, Y, F or Q;
$X_{11}$ is D, E or N;
$X_{12}$ is W, F, H or Y;
$X_{13}$ is V, F, E, K, A, G, L, P or Y;
$X_{14}$ is N, R, E, Q or D;
$X_{15}$ is K, R, E, V, W, H or D;
or
$X_1$ is I, V, A, G, L, or P;
$X_2$ is M, K, R, E, Q, W or Y;
$X_3$ is V, F, A, G, L, P, I, Y or W;
$X_4$ is T, Q, S, N or Y;
$X_5$ is I, F, A, G, L, P, V or Y;
$X_6$ is P, G, A, L, V, I or N;
$X_7$ is A, Q, G, L, P, V, I, N or E;
$X_8$ is D, E, N, Q or Y;
$X_9$ is L, V, F, W, A, G, P, I or H;
$X_{10}$ is W, Y, F or Q;
$X_{11}$ is D, E or N;
$X_{12}$ is W, F, H or Y;
$X_{13}$ is V, F, E, K, A, G, L, P or Y;
$X_{14}$ is N, R, E, Q or D;
$X_{15}$ is K, R, E, V, W, H or D;
or
$X_1$ is I, V, A, G, L, or P;
$X_2$ is H, M, K, R, E, Q, W or Y;
$X_3$ is V, F, A, G, L, P, I, Y or W;
$X_4$ is T, Q, S, N or Y;
$X_5$ is I, F, A, G, L, P, V or Y;
$X_6$ is P, G, A, L, V, I or N;
$X_7$ is A, Q, G, L, P, V, I, N or E;
$X_8$ is D, E, N, Q or Y;
$X_9$ is L, V, F, W, A, G, P, I or H;
$X_{10}$ is Y, F or Q;
$X_{11}$ is D, E or N;
$X_{12}$ is W, F, H or Y;
$X_{13}$ is V, F, E, K, A, G, L, P or Y;
$X_{14}$ is N, R, E, Q or D;
$X_{15}$ is K, R, E, V, W, H or D;
or
$X_1$ is I, V, A, G, L, or P;
$X_2$ is M, K, R, E, Q, W or Y;
$X_5$ is V, F, A, G, L, P, I, Y or W;
$X_4$ is T, Q, S, N or Y;
$X_5$ is I, F, A, G, L, P, V or Y;
$X_6$ is P, G, A, L, V, I or N;
$X_7$ is A, Q, G, L, P, V, I, N or E;
$X_8$ is D, E, N, Q or Y;
$X_9$ is L, V, F, W, A, G, P, I or H;
$X_{10}$ is Y, F or Q;
$X_{11}$ is D, E or N;
$X_{12}$ is W, F, H or Y;
$X_{13}$ is V, F, E, K, A, G, L, P or Y;
$X_{14}$ is N, R, E, Q or D;
$X_{15}$ is K, R, E, V, W, H or D;
or
$X_1$ is V, A, G, L, or P;
$X_2$ is H, M, K, R, E, Q, W or Y;
$X_5$ is V, F, A, G, L, P, I, Y or W;
$X_4$ is T, Q, S, N or Y;
$X_5$ is I, F, A, G, L, P, V or Y;
$X_6$ is P, G, A, L, V, I or N;
$X_7$ is A, Q, G, L, P, V, I, N or E;
$X_8$ is D, E, N, Q or Y;
$X_9$ is L, V, F, W, A, G, P, I or H;
$X_{10}$ is Y, F or Q;
$X_{11}$ is D, E or N;
$X_{12}$ is W, F, H or Y;
$X_{13}$ is V, F, E, K, A, G, L, P or Y;
$X_{14}$ is N, R, E, Q or D;
$X_{15}$ is K, R, E, V, W, H or D;
or
$X_1$ is V, A, G, L, or P;
$X_2$ is M, K, R, E, Q, W or Y;
$X_3$ is V, F, A, G, L, P, I, Y or W;

$X_4$ is T, Q, S, N or Y:
$X_5$ is I, F, A, G, L, P, V or Y;
$X_6$ is P, G, A, L, V, I or N;
$X_7$ is A, Q, G, L, P, V, I, N or E;
$X_8$ is D, E, N, Q or Y;
$X_9$ is L, V, F, W, A, G, P, I or H:
$X_{10}$ is Y, F or Q;
$X_{11}$ is D, E or N;
$X_{12}$ is W, F, H or Y;
$X_{13}$ is V, F, E, K, A, G, L, P or Y;
$X_{14}$ is N, R, E, Q or D;
$X_{15}$ is K, R, E, V, W, H or D;
or
$X_1$ is I, V, A, G, L or P;
$X_2$ is M, K, N, R, E, Q, W or Y;
$X_3$ is V, F, A, G, L, P, I, Y or W;
$X_4$ is T, Q, S, N or Y;
$X_5$ is I, F, A, G, L, P, V or Y;
$X_6$ is P, G, A, L, V, I or N;
$X_7$ is A, Q, G, L, P, V, I, N or E;
$X_8$ is D, E, N, Q or Y:
$X_9$ is L, V, F, W, A, G, P, I or H:
$X_{10}$ is W, Y, F or Q;
$X_{11}$ is E or N;
$X_{12}$ is W, F, H or Y;
$X_{13}$ is I, V, F, E, K, A, G, L, P or Y;
$X_{14}$ is N, R, E, Q or D;
$X_{15}$ is K, R, E, V, W, H or D;
or
$X_1$ is I, V, A, G, L or P;
$X_2$ is H, M, K, N, R, E, Q, W or Y;
$X_3$ is V, F, A, G, L, P, I, Y or W;
$X_4$ is T, Q, S, N or Y;
$X_5$ is I, F, A, G, L, P, V or Y;
$X_6$ is P, G, A, L, V, I or N;
$X_7$ is A, Q, G, L, P, V, I, N or E;
$X_8$ is D, E, N, Q or Y:
$X_9$ is L, V, F, W, A, G, P, I or H;
$X_{10}$ is W, Y, F or Q;
$X_{11}$ is E or N;
$X_{12}$ is W, F, H or Y;
$X_{13}$ is I, V, F, E, K, A, G, L, P or Y;
$X_{14}$ is N, R, E, Q or D;
$X_{15}$ is K, R, E, V, W, H or D;
or
$X_1$ is V, A, G, L or P;
$X_2$ is M, K, N, R, E, Q, W or Y;
$X_3$ is V, F, A, G, L, P, I, Y or W;
$X_4$ is T, Q, S, N or Y;
$X_5$ is I, F, A, G, L, P, V or Y;
$X_6$ is P, G, A, L, V, I or N;
$X_7$ is A, Q, G, L, P, V, I, N or E;
$X_8$ is D, E, N, Q or Y;
$X_9$ is L, V, F, W, A, G, P, I or H;
$X_{10}$ is W, Y, F or Q;
$X_{11}$ is E or N;
$X_{12}$ is W, F, H or Y;
$X_{13}$ is I, V, F, E, K, A, G, L, P or Y;
$X_{14}$ is N, R, E, Q or D;
$X_{15}$ is K, R, E, V, W, H or D;
or
$X_1$ is I, V, A, G, L, or P;
$X_2$ is H, M, K, R, E, Q, W or Y;
$X_3$ is V, F, A, G, L, P, I, Y or W;
$X_4$ is T, Q, S, N or Y;
$X_5$ is I, F, A, G, L, P, V or Y;
$X_6$ is P, G, A, L, V, I or N;

$X_7$ is A, Q, G, L, P, V, I, N or E;
$X_8$ is D, E, N, Q or Y;
$X_9$ is L, V, F, W, A, G, P, I or H;
$X_{10}$ is Y, F or Q;
$X_{11}$ is E or N;
$X_{12}$ is W, F, H or Y;
$X_{13}$ is I, V, F, E, K, A, G, L, P or Y;
$X_{14}$ is N, R, E, Q or D;
$X_{15}$ is K, R, E, V, W, H or D;
Or
$X_1$ is I, V, A, G, L, or P;
$X_2$ is H, M, K, R, E, Q, W or Y;
$X_3$ is V, F, A, G, L, P, I, Y or W;
$X_4$ is T, Q, S, N or Y;
$X_5$ is I, F, A, G, L, P, V or Y;
$X_6$ is P, G, A, L, V, I or N;
$X_7$ is A, Q, G, L, P, V, I, N or E;
$X_8$ is D, E, N, Q or Y;
$X_9$ is L, V, F, W, A, G, P, I or H;
$X_{10}$ is W, Y, F or Q:
$X_{11}$ is E or N;
$X_{12}$ is W, F, H or Y;
$X_{13}$ is V, F, E, K, A, G, L, P or Y;
$X_{14}$ is N, R, E, Q or D;
$X_{15}$ is K, R, E, V, W, H or D;
or
$X_1$ is I, V, A, G, L, or P;
$X_2$ is H, M, K, R, E, Q, W or Y;
$X_3$ is V, F, A, G, L, P, I, Y or W;
$X_4$ is T, Q, S, N or Y;
$X_5$ is I, F, A, G, L, P, V or Y;
$X_6$ is P, G, A, L, V, I or N;
$X_7$ is A, Q, G, L, P, V, I, N or E;
$X_8$ is D, E, N, Q or Y;
$X_9$ is L, V, F, W, A, G, P, I or H;
$X_{10}$ is Y, F or Q;
$X_{11}$ is E or N;
$X_{12}$ is W, F, H or Y;
$X_{13}$ is V, F, E, K, A, G, L, P or Y;
$X_{14}$ is N, R, E, Q or D;
$X_{15}$ is K, R, E, V, W, H or D;
or
$X_1$ is I, V, A, G, L, or P;
$X_2$ is H, M, K, R, E, Q, W or Y;
$X_3$ is V, F, A, G, L, P, I, Y or W;
$X_4$ is T, Q, S, N or Y;
$X_5$ is I, F, A, G, L, P, V or Y;
$X_6$ is P, G, A, L, V, I or N;
$X_7$ is A, Q, G, L, P, V, I, N or E;
$X_8$ is D, E, N, Q or Y:
$X_9$ is L, V, F, W, A, G, P, I or H;
$X_{10}$ is W, Y, F or Q;
$X_{11}$ is D, E or N;
$X_{12}$ is W, F, H or Y;
$X_{13}$ is I, V, F, E, K, A, G, L, P or Y;
$X_{14}$ is R, E, Q or D;
$X_{15}$ is R, E, V, W, H or D;
or
$X_1$ is V, A, G, L, or P;
$X_2$ is H, M, K, R, E, Q, W or Y;
$X_3$ is V, F, A, G, L, P, I, Y or W;
$X_4$ is T, Q, S, N or Y;
$X_5$ is I, F, A, G, L, P, V or Y;
$X_6$ is P, G, A, L, V, I or N;
$X_7$ is A, Q, G, L, P, V, I, N or E;
$X_8$ is D, E, N, Q or Y:
$X_9$ is L, V, F, W, A, G, P, I or H;

$X_{10}$ is W, Y, F or Q;
$X_{11}$ is D, E or N;
$X_{12}$ is W, F, H or Y;
$X_{13}$ is I, V, F, E, K, A, G, L, P or Y;
$X_4$ is R, E, Q or D;
$X_{15}$ is R, E, V, W, H or D;
or
$X_1$ is I, V, A, G, L, or P;
$X_2$ is M, K, R, E, Q, W or Y;
$X_3$ is V, F, A, G, L, P, I, Y or W;
$X_4$ is T, Q, S, N or Y;
$X_5$ is I, F, A, G, L, P, V or Y;
$X_6$ is P, G, A, L, V, I or N;
$X_7$ is A, Q, G, L, P, V, I, N or E;
$X_8$ is D, E, N, Q or Y:
$X_9$ is L, V, F, W, A, G, P, I or H;
$X_{10}$ is W, Y, F or Q;
$X_{11}$ is D, E or N;
$X_{12}$ is W, F, H or Y;
$X_{13}$ is I, V, F, E, K, A, G, L, P or Y;
$X_{14}$ is R, E, Q or D;
$X_{15}$ is R, E, V, W, H or D.

Particularly preferred peptides of formula (I) among those described above are those wherein $X_1$ is V.

As will be demonstrated in the experimental section, when the first amino acid in the peptide of formula (I) is a valine, the peptide surprisingly shows chemical-physical properties particularly advantageous for topical and ophthalmic use and an increased affinity for IL-17A. Preferably, in the above peptide of formula (I) all aminoacids $X_1$ to $X_1S$ are present. Preferred individual peptides of formula (I) according to the present invention are listed in Table 1 below.

TABLE 1

| SEQ ID NO: | Sequence |
| --- | --- |
| SEQ ID NO: 2 | VHVTIPADLWDWINK |
| SEQ ID NO: 3 | IMVTIPADLWDWINK |
| SEQ ID NO: 4 | VMVTIPADLWDWINK |
| SEQ ID NO: 5 | IHVTIPAELWDWINK |
| SEQ ID NO: 6 | IHVTIPADLYDWINK |
| SEQ ID NO: 7 | IHVTIPADLYEWINK |
| SEQ ID NO: 8 | IHVTIPADLWDVNK |
| SEQ ID NO: 9 | IHVTIPADLWDWIRK |
| SEQ ID NO: 10 | IHVTIPADLWDWINR |
| SEQ ID NO: 11 | IHVTIPADLWDWIEK |
| SEQ ID NO: 12 | IHVTIPADLWDWINE |
| SEQ ID NO: 13 | IHVTIPADLYEWINK |
| SEQ ID NO: 14 | IHVTIPADLWDWRR |
| SEQ ID NO: 15 | IHVTIPADLWDWVEE |
| SEQ ID NO: 16 | VMVTIPADLYEWINK |
| SEQ ID NO: 17 | VMVTIPADLYEWIRR |
| SEQ ID NO: 18 | VMVTIPADLYEWIEE |
| SEQ ID NO: 42 | IMVTIPADLYEWIEE |

TABLE 1-continued

| SEQ ID NO: | Sequence |
| --- | --- |
| SEQ ID NO: 111 | VHVTIPAELWEWVRR |
| SEQ ID NO: 112 | VHFTIPADLWEWVRR |
| SEQ ID NO: 113 | VHVQIPADLWEWVRR |
| SEQ ID NO: 114 | VHVTFPADLWEWVRR |
| SEQ ID NO: 115 | VHVTIPQDLWEWVRR |
| SEQ ID NO: 116 | VHVTIPANLWEWVRR |
| SEQ ID NO: 117 | VHVTIPADFWEWVRR |
| SEQ ID NO: 118 | VHVTIPADLYEWVRR |
| SEQ ID NO: 119 | VHVTIPADLWNWVRR |
| SEQ ID NO: 120 | VHVTIPADLWEFVRR |
| SEQ ID NO: 121 | VHVTIPADLWEWFRR |
| SEQ ID NO: 122 | VHVYIPAELWEWVRR |
| SEQ ID NO: 123 | VHVTIPAEWWEWVRR |
| SEQ ID NO: 124 | VHFTFPQDLWEWVRR |
| SEQ ID NO: 125 | VHFTFPQDFWEWVRR |
| SEQ ID NO: 126 | VHFTIPQDLYEWVRR |
| SEQ ID NO: 127 | VHFTFPQDLWNWVRR |
| SEQ ID NO: 128 | VHFTFPQDLWEFVRR |
| SEQ ID NO: 129 | VHFTFPQDLWEWFRR |
| SEQ ID NO: 130 | VHFQPADLWEWVRR |
| SEQ ID NO: 131 | VHFQPADFWEVWRR |
| SEQ ID NO: 132 | VHFQFPADLYEWVRR |
| SEQ ID NO: 133 | VHFQFPADLWNWVRR |
| SEQ ID NO: 134 | VHFQFPADLWEFVRR |
| SEQ ID NO: 135 | VHFQFPADLWEWFRR |
| SEQ ID NO: 136 | VHFQFPQDWWEWVRR |
| SEQ ID NO: 137 | VHFQIPQDWWEWVRR |
| SEQ ID NO: 138 | VHFQFPQDWYEWVRR |
| SEQ ID NO: 139 | VHFQFPQDWWNWVRR |
| SEQ ID NO: 140 | VHFQFPQDLWEFVRR |
| SEQ ID NO: 141 | VHFQFPQDWWEWFRR |
| SEQ ID NO: 142 | VHFTIPADFWEWFRR |
| SEQ ID NO: 143 | VHVQIPADFWEWFRR |
| SEQ ID NO: 144 | VHVTFPADLWEWFRR |
| SEQ ID NO: 145 | VHVTIPQDFWEWFRR |
| SEQ ID NO: 146 | VHFTIPQDWWEWVRR |
| SEQ ID NO: 147 | VHFTFPQDLYNWVRR |
| SEQ ID NO: 148 | VHFTFPQDLYNFVRR |
| SEQ ID NO: 149 | VHVTIPADLYNFFRR |

TABLE 1-continued

| SEQ ID NO: | Sequence |
| --- | --- |
| SEQ ID NO: 150 | VHFQFPQDLWEWVRR |
| SEQ ID NO: 151 | VHFTIPQDLYNWRR |
| SEQ ID NO: 152 | VHFTIPADLYNFVRR |
| SEQ ID NO: 153 | VHFQIPQDLYNFFRR |
| SEQ ID NO: 154 | VHFQFPQEWYNWFRR |
| SEQ ID NO: 155 | VRFQFGQEWYNFFRR |
| SEQ ID NO: 158 | AHVTIPADLWDWINK |
| SEQ ID NO: 159 | GHVTIPADLWDWINK |
| SEQ ID NO: 160 | LHVTIPADLWDWINK |
| SEQ ID NO: 161 | PHVTIPADLWDWINK |
| SEQ ID NO: 162 | IRVTIPADLWDWINK |
| SEQ ID NO: 163 | IKVTIPADLWDWINK |
| SEQ ID NO: 164 | IEVTIPADLWDWINK |
| SEQ ID NO: 165 | IQVTIPADLWDWINK |
| SEQ ID NO: 166 | IYVTIPADLWDWINK |
| SEQ ID NO: 167 | IHATIPADLWDWINK |
| SEQ ID NO: 168 | IHGTIPADLWDWINK |
| SEQ ID NO: 169 | IHLTIPADLWDWINK |
| SEQ ID NO: 170 | IHPTIPADLWDWINK |
| SEQ ID NO: 171 | IHITIPADLWDWINK |
| SEQ ID NO: 172 | IHYTIPADLWDWINK |
| SEQ ID NO: 173 | IHWTIPADLWDWINK |
| SEQ ID NO: 174 | IHFTIPADLWDWINK |
| SEQ ID NO: 175 | IHVSIPADLWDWINK |
| SEQ ID NO: 176 | IHVYIPADLWDWINK |
| SEQ ID NO: 177 | IHVNIPADLWDWINK |
| SEQ ID NO: 178 | IHVQIPADLWDWINK |
| SEQ ID NO: 179 | IHVTAPADLWDWINK |
| SEQ ID NO: 180 | IHVTGPADLWDWINK |
| SEQ ID NO: 181 | IHVTLPADLWDWINK |
| SEQ ID NO: 182 | IHVTPPADLWDWINK |
| SEQ ID NO: 183 | IHVTVPADLWDWINK |
| SEQ ID NO: 184 | IHVTFPADLWDWINK |
| SEQ ID NO: 185 | IHVTYPADLWDWINK |
| SEQ ID NO: 186 | IHVTIAADLWDWINK |
| SEQ ID NO: 187 | IHVTIGADLWDWINK |
| SEQ ID NO: 188 | IHVTILADLWDWINK |
| SEQ ID NO: 189 | IHVTIVADLWDWINK |
| SEQ ID NO: 190 | IHVTIIADLWDWINK |
| SEQ ID NO: 191 | IHVTINADLWDWINK |
| SEQ ID NO: 192 | IHVTIPQDLWDWINK |
| SEQ ID NO: 193 | IHVTIPLDLWDWINK |
| SEQ ID NO: 194 | IHVTIPPDLWDWINK |
| SEQ ID NO: 195 | IHVTIPVDLWDWINK |
| SEQ ID NO: 196 | IHVTIPIDLWDWINK |
| SEQ ID NO: 197 | IHVTIPNDLWDWINK |
| SEQ ID NO: 198 | IHVTIPQDLWDWINK |
| SEQ ID NO: 199 | IHVTIPAQLWDWINK |
| SEQ ID NO: 200 | IHVTIPAYLWDWINK |
| SEQ ID NO: 201 | IHVTIPADAWDWINK |
| SEQ ID NO: 202 | IHVTIPADGWDWINK |
| SEQ ID NO: 203 | IHVTIPADPWDWINK |
| SEQ ID NO: 204 | IHVTIPADVWDWINK |
| SEQ ID NO: 205 | IHVTIPADIWDWINK |
| SEQ ID NO: 206 | IHVTIPADLHDWINK |
| SEQ ID NO: 207 | IHVTIPADLFDWINK |
| SEQ ID NO: 208 | IHVTIPADLWNWINK |
| SEQ ID NO: 209 | IHVTIPADLWDHINK |
| SEQ ID NO: 210 | IHVTIPADLWDFINK |
| SEQ ID NO: 211 | IHVTIPADLWDYINK |
| SEQ ID NO: 212 | IHVTIPADLWDWENK |
| SEQ ID NO: 213 | IHVTIPADLWDWKNK |
| SEQ ID NO: 214 | IHVTIPADLWDWANK |
| SEQ ID NO: 215 | IHVTIPADLWDWGNK |
| SEQ ID NO: 216 | IHVTIPADLWDWLNK |
| SEQ ID NO: 217 | IHVTIPADLWDWPNK |
| SEQ ID NO: 218 | IHVTIPADLWDWFNK |
| SEQ ID NO: 219 | IHVTIPADLWDWYNK |
| SEQ ID NO: 220 | IHVTIPADLWDWIQK |
| SEQ ID NO: 221 | IHVTIPADLWDWIDK |
| SEQ ID NO: 222 | IHVTIPADLWDWINH |
| SEQ ID NO: 223 | IHVTIPADLWDWIND |
| SEQ ID NO: 224 | VHVTVPQELWEWVRR |
| SEQ ID NO: 225 | VHVTVPQELFEWVRR |
| SEQ ID NO: 226 | VHVTVPQELYEWVRR |
| SEQ ID NO: 227 | VHVTVPQELWEWVEE |
| SEQ ID NO: 228 | VHVTVPQELFEWVEE |
| SEQ ID NO: 229 | VHVTVPQELYEWVEE |

TABLE 1-continued

| SEQ ID NO: | Sequence |
|---|---|
| SEQ ID NO: 230 | VHVSIPQELWEWVRR |
| SEQ ID NO: 231 | VHVSVPQELWEWVRR |
| SEQ ID NO: 232 | VHVSVPQELYEWVRR |
| SEQ ID NO: 233 | VRVTIPQELWEWVRR |
| SEQ ID NO: 234 | VRVTVPQELYEWVRR |
| SEQ ID NO: 235 | VRVTVPQELWEWVRR |
| SEQ ID NO: 236 | VHVTVPQEIYEWVRR |
| SEQ ID NO: 237 | VHVTIPQEIWEWVRR |
| SEQ ID NO: 238 | VHFTVPQELYEWVRR |
| SEQ ID NO: 239 | VKISVPADLWDWINK |
| SEQ ID NO: 240 | LRISVPADLWDWINK |
| SEQ ID NO: 241 | LRIYVPADLWDWINK |
| SEQ ID NO: 242 | VRGYVPADLWDWINK |
| SEQ ID NO: 243 | VRAYVPADLWDWINK |
| SEQ ID NO: 244 | VRLYVPADLWDWINK |
| SEQ ID NO: 245 | VRIYLPADLWDWINK |
| SEQ ID NO: 246 | IHVTIPLEIFEWLQH |
| SEQ ID NO: 247 | IHVTIPLEIFEWAQH |
| SEQ ID NO: 248 | IHVTIPLEIFEWLQR |
| SEQ ID NO: 249 | IHVTIPLEVFEWLQH |
| SEQ ID NO: 250 | IHVTIPGEIFEWLQH |
| SEQ ID NO: 251 | VRFSVPQEIYEWVRR |
| SEQ ID NO: 252 | LRISVPLEIFEWLQH |
| SEQ ID NO: 253 | LRGSVPLEIFEWLQH |
| SEQ ID NO: 254 | VKISVPLEIFEWLQH |
| SEQ ID NO: 255 | VEFNFPQQVYEWFDD |
| SEQ ID NO: 256 | VEFNFPQQVYEWVRR |
| SEQ ID NO: 257 | TWYVFNEQHQEYVRK |

Other peptides inhibitor of IL-17A according to the invention are those of Table 1A

TABLE 1A

| SEQ ID NO: 156 | VPGAGVPGAGIHVTI |
|---|---|
| SEQ ID NO: 157 | VPGAGVPGAGIHVTIPA |

Further amino acid sequences may be added at the N- or C-terminal of the peptides according to the first object of the invention.

According to a preferred embodiment, the above described peptides of formula (I) or (II) are bound at their N- and/or C-terminal to a further amino acid sequence. Sequence A, having the amino acid sequence of formula (III)

$$Y_1\text{-}Y_2\text{-}Y_3\text{-}Y_4\text{-}Y_5\text{-}Y_6\text{-}Y_7\text{-}Y_8\text{-}Y_9\text{-}Y_{10}\text{-}Y_{11}\text{-}Y_{12}\text{-}Y_{13}\text{-}Y_{14}\text{-}Y_{15}\text{-}Y_{16}$$

wherein:
$Y_1$ is A, T, V, K, R, I, L, X or G;
$Y_2$ is R, W, P, E, Q or A;
$Y_3$ is K, W, G, T, I, R or P;
$Y_4$ is K, T, E, W, A, R, D, G X or F;
$Y_5$ is A, E, T, G, W, I, R, P or V;
$Y_6$ is A, W, E, R, G, P or absent;
$Y_7$ is K, S, W, T, F, R, V, G or absent;
$Y_8$ is A, Q, W, R, G or absent;
$Y_9$ is N, G or absent;
$Y_{10}$ is R or absent;
$Y_{11}$ is R or absent;
$Y_{12}$ is M or absent;
$Y_{13}$ is K or absent;
$Y_{14}$ is W or absent;
$Y_{15}$ is K or absent;
$Y_{16}$ is K or absent.

Preferably, in the sequence of formula (III), when an amino acid is absent, also the aminoacids at the N terminal of said aminoacids are absent. For example, if amino acid $Y_6$ is absent, also aminoacids $Y_7$ to $Y_{16}$ are absent.

Preferred sequences of formula (III) according to the present invention are listed in Table 2 below.

TABLE 2

| SEQUENCE ID | Sequence |
|---|---|
| SEQ ID NO: 44 | ARKKAAKA |
| SEQ ID NO: 45 | TWWTEWSQ |
| SEQ ID NO: 46 | TWWETWW |
| SEQ ID NO: 47 | VPGWG |
| SEQ ID NO: 48 | KETWWETW |
| SEQ ID NO: 49 | VPGKG |
| SEQ ID NO: 50 | VPGAG |
| SEQ ID NO: 51 | RQIKIWFQNRRMKWKK |
| SEQ ID NO: 52 | RRRRRRRR |
| SEQ ID NO: 53 | VPGDG |
| SEQ ID NO: 54 | VPGXG |
| SEQ ID NO: 55 | IPGG |
| SEQ ID NO: 56 | AVGVP |
| SEQ ID NO: 57 | IPGXG |
| SEQ ID NO: 58 | IPGVG |
| SEQ ID NO: 59 | LPGXG |
| SEQ ID NO: 60 | LPGVG |
| SEQ ID NO: 61 | VAPGVG |
| SEQ ID NO: 62 | XPGVG |
| SEQ ID NO: 63 | GVGVPGVG |
| SEQ ID NO: 64 | VPGFGVGAG |
| SEQ ID NO: 65 | VPGGVPGG |

Accordingly, a second object of the invention is a peptide having an amino acid sequence comprising, preferably consisting of, the sequence of the peptide of formula (I) or (II)

according to the first object of the invention and at the C- and/or N-terminal of said sequence a Sequence A as above described.

The amino acid sequence Sequence A may be bound to both the N- and C-terminal of the peptide of formula (I) or (II). In such a case, the two amino acid sequences Sequence A bound to the N- and to C-terminal of said peptide may be the same or different.

Alternatively, the amino acid sequence Sequence A may be bound either to the N- or to the C-terminal of the peptide.

Preferred individual peptides according to this object of the invention are listed in Table 3 below.

TABLE 3

| SEQ ID NO: | Sequence |
|---|---|
| SEQ ID NO: 21 | VMVTIPADLYEWIEEARKKAAKA |
| SEQ ID NO: 22 | VMVTIPADLYEWIEEGGTWWTEWSQ |
| SEQ ID NO: 23 | VMVTIPADLYEWIEETWWETWW |
| SEQ ID NO: 24 | VMVTIPADLYEWIEEVPGWG |
| SEQ ID NO: 25 | VMVTIPADLYEWIEEGGKETWWETW |
| SEQ ID NO: 26 | VMVTIPADLYEWIEEVPGKG |
| SEQ ID NO: 27 | VMVTIPADLYEWIEEVPGAG |
| SEQ ID NO: 28 | VMVTIPADLYEWIEERQIKIWFQNRRMKWKK |
| SEQ ID NO: 31 | ARKKAAKAVMVTIPADLYEWIEE |
| SEQ ID NO: 32 | GGTWWTEWSQVMVTIPADLYEWIEE |
| SEQ ID NO: 33 | GGKETWWETWVMVTIPADLYEWIEE |
| SEQ ID NO: 34 | VPGWGVMVTIPADLYEWIEE |
| SEQ ID NO: 35 | VPGAGVMVTIPADLYEWIEE |
| SEQ ID NO: 36 | VPGKGVMVTIPADLYEWIEE |
| SEQ ID NO: 37 | VMVTIPADLYEWIEEVPGAGVPGAG |
| SEQ ID NO: 38 | VPGAGVPGAGVMVTIPADLYEWIEE |
| SEQ ID NO: 39 | VPGDGVMVTIPADLYEWIEE |
| SEQ ID NO: 40 | VMVTIPADLYEWIEEVPGDG |

In an embodiment alternative to the above, said peptides of formula (I) or (II) according to the first object of the invention may be bound at their N- and/or C-terminal to an amino acid sequence $(A)_m$, wherein A is an amino acid selected from R, K, G, E, Q or A, preferably R, K, G, E or A, and m is an integer between 1 and 10.

The amino acid sequence $(A)_m$ may be bound to both the N- and C-terminal of the peptide of formula (I) or (II). In such a case, the two amino acid sequences $(A)_m$ attached to the N- and to the C-terminal of said peptide have may be the same or different.

Alternatively, the amino acid sequence $(A)_m$ may be attached either to the N- or the C-terminal of said peptide.

Accordingly, a third object of the invention is a peptide having an amino acid sequence that comprises, preferably consists of, the sequence of the peptide according to the first object of the invention and at the C- and/or N-terminal of said sequence a sequence $(A)_m$ as above defined.

Preferred individual peptides according to this embodiment of the invention are listed in Table 4 below.

TABLE 4

| SEQ ID NO: | Sequence |
|---|---|
| SEQ ID NO: 19 | VMVTIPADLYEWIEERRRRRR |
| SEQ ID NO: 20 | VMVTIPADLYEWIEERRR |
| SEQ ID NO: 29 | RRRRRRRVMVTIPADLYEWIEE |
| SEQ ID NO: 30 | VMVTIPADLYEWIEERRRRRRRR |
| SEQ ID NO: 43 | IMVTIPADLYEWIEEQ |

In a particular embodiment, said peptides of formula (I) or (II) are bound to both a sequence Sequence A and a sequence $(A)_m$. In this case, said peptides are bound at their N- and/or C-terminal to an amino acid sequence $(A)_m$, as defined above, which is bound at its N- and/or C-terminal to an amino acid sequence Sequence A, as described above.

Accordingly, a fourth object of the invention is a peptide having an amino acid sequence that comprises, preferably consists of, the sequence of the peptide according to the first object of the invention, at the C- and/or N-terminal of said sequence a sequence $(A)_m$ as above described and at the C- and/or N-terminal of said sequence $(A)_m$ a Sequence A as above described.

According to a preferred embodiment of the peptide according to any of the above objects of the invention, said peptide is bound at the C- and/or N-terminal to a protective cap group, able to prevent degradation.

Any protective cap group customary in the art may be used.

Preferably, the protective cap group bound to a C-terminal is selected from amides, preferably N-alkyl amides, aldehydes, esters, preferably methyl and ethyl esters, p-Nitroanilide, 7-Amino-4-methylcoumarin.

Preferably, the protective group cap bound to a N-terminal is selected from acetyl, formyl, pyroglutamyl, fatty acids, urea, carbamate sulfonamide, alkylamine.

Preferably, the above peptides are bound to the protective cap group at the N-terminal only. More preferably said peptides are bound to the protective cap group at the N-terminal only and the protective cap group is acetyl.

It is particularly advantageous to prepare dimers of the above described peptides according any of the different objects of the invention, preferably of the peptides of formula (I) or (II) according to the first object of the invention, in order to increase binding affinity and inhibitor activity.

In accordance with the above, preferably the peptides according to the different objects of the invention above described, preferably of the peptides of formula (I) or (II) according to the first object of the invention, more preferably the peptides of formula (I) according to the first object of the invention, are present in form of dimers.

Accordingly, a fifth object of the present invention is a dimer formed by two peptides according to any of the above objects of the invention. Preferably said peptides are peptides of formula (I) or (II) according to the first object of the invention, more preferably they are peptides of formula (I) according to the first object of the invention.

Preferably, said dimer is a homodimer, wherein the two peptides forming the dimer have an identical sequence. Preferably, in said dimer, the peptides are linked by means of a spacer molecule, preferably a polyethylene glycol spacer.

Preferably, according to this embodiment, polyethylene glycol is linked to the N-terminal of the peptides according to the invention or to the aminoacids $X_4$, $X_7$ or $X_{14}$ of two peptides of formula (I).

According to a further embodiment, in the absence of a protective group cap, the peptides according to the different objects of the invention are bound, preferably at their C- and/or N-terminal, to a biomolecule to form a bioconjugate. Preferably, said biomolecule is selected from capric acid, capronic acid, ascorbic acid, NAG-NAM, NAG, NAM, hyaluronic acid, alginic acid, chitin, $(GalNAc)_2$, Gal-alpha1, 3-GalNAc and trigalacturonic acid.

The biomolecule is bound to the peptide either to add a specific function to the peptide or to modulate the physical chemical properties of the peptide. For example, ascorbic acid provides an antioxidant activity to the peptide, capronic acid favors the anchoring of the peptide to the cell membrane.

Accordingly, a sixth object of the invention is a bioconjugate comprising, preferably consisting of, a peptide according to the different objects of the invention, preferably a peptide of formula (I) or (II) according to the first object of the invention, more preferably a peptide of formula (I) according to the first object of the invention, and at least a biomolecule, as above described. Preferably, in said bioconjugate, said biomolecule is bound to the N- and/or C-terminal of said peptide.

Preferred bioconjugates according to this embodiment are listed in Table 5 below.

TABLE 5

| Bioconjugate name | Sequence |
|---|---|
| Bio-1 | NAM-IMVTIPADLYEWIEE (NAM plus SEQ ID NO: 42) |
| Bio-2 | IMVTIPADLYEWIEEQ-NAG (SEQ ID NO: 42 plus NAG) |
| Bio-3 | NAG-NAM-IMVTIPADLYEWIEE (NAG-NAM plus SEQ ID NO: 42) |
| Bio-4 | capric acid-IMVTIPADLYEWIEE (capric acid plus SEQ ID NO: 42) |
| Bio-5 | Ascorbic acid IMVTIPADLYEWIEE (Ascorbic acid plus SEQ ID NO: 42) |

According to one embodiment, in the above bioconjugate the above biomolecule or protective cap group are bound directly to the N and/or C-terminal of the peptide.

According to one embodiment, said biomolecule is bound to both the N- and C-terminal of the peptide. In such a case, the two biomolecules bound to the N and to the C terminal of said peptide may be the same or different.

According to an alternative embodiment, said biomolecule is bound to either the N- or the C-terminal of the peptide.

According to an alternative embodiment, the above biomolecule or protective cap group are linked to the N- and/or C terminal of the peptide by means of a linker. Preferably, said linker is selected from 4-aminobutyric acid, beta-alanine, 2-aminoethoxy-acetic acid, 5-aminovaleric acid, 6-aminocaproic acid, 8-Amino-3,6-dioxaoctanoic acid, 12-amino-4,7,10-trioxadodecanoic acid, 15-amino-4,7,10,13-tetraoxapenta-decanoic acid and trioxatridecan-succinamic acid. Preferably, when the linker is attached on one amino acid Lysine, said linker is selected from NHS-ester, isocyanates, benzoyl fluorides or carbamates.

In accordance with to the different embodiments described above, the present invention relates to a compound comprising or consisting of the IL-17A binding peptide of formula (I) or (II) above described, and having the following formula (IV):

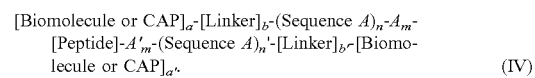

[Biomolecule or CAP]$_a$-[Linker]$_b$-(Sequence $A)_n$-$A_m$-[Peptide]-$A'_{m'}$-(Sequence $A)_{n'}$-[Linker]$_{b'}$-[Biomolecule or CAP]$_{a'}$.     (IV)

wherein, independently from each other:
a=0 or 1;
b=0 or 1;
a'=0 or 1;
b'=0 or 1;
m=0 to 10;
m'=0 to 10:
n=0 or 5;
n'=0 or 5,
and
Peptide is the polypeptide according to formula (I) or formula (II);
A or A' is one amino acid selected from R, K, G, E or A repeated m or m' times; and Sequence A comprises the sequence of formula (III) above described;
Biomolecule is, independently from each other, capronic acid, ascorbic acid, NAG-NAM, NAG, NAM, hyaluronic acid, alginic acid, chitin, $(GalNAc)_2$, Gal-alpha1,3-GalNAc or trigalacturonic acid;
CAP is, independently from each other, amide, aldehyde, ester, p-Nitroanilide, 7-Amino-4-Methylcoumarin, acetyl, formyl, pyroglutamyl or a fatty acid;
Linker is, independently from each other, 4-aminobutyric acid, beta-alanine, 2-aminoethoxy-acetic acid, 5-aminovaleric acid, 6-aminocaproic acid, 8-Amino-3,6-dioxaoctanoic acid, 12-amino-4,7,10-tioxadodecanoic acid, 15-amino-4,7,10,13-tetraoxapenta-decanoic acid or trioxatridecan-succinamic acid.

According to a preferred embodiment, said Sequence A is attached to the N-terminal or to the C-terminal of the peptide of formula (I) or (II).

Some examples of the possible compounds according to the present invention are reported here below, but all the other possible combination comprised in the formula (IV) can be present:

[Biomolecule or Cap]-[Linker]-(Sequence A)-A-[Peptide]-;
[Biomolecule or Cap]-(Sequence A)-A-[Peptide]-;
[Biomolecule or Cap]-A-[Peptide]-;
[Biomolecule or Cap]-[Peptide]-;
[Peptide]-$A_m$-(Sequence $A)_n$-[Biomolecule or Cap]$_{a'}$;
[Peptide]-$A_m$-[Biomolecule or Cap]$_{a'}$;
[Peptide]-[Biomolecule or Cap]$_{a'}$, According to a preferred embodiment, the biomolecule in formula (IV) of the present invention is selected from ascorbic acid, capronic acid, NAG or NAM.

According to a further preferred embodiment the Cap according to the present invention is a C-ter modification selected from amides, preferably N-alkyl amides, aldehydes, esters, preferably methyl and ethyl esters, p-Nitroanilide, 7-Amino-4-Methylcoumarin or N-ter modification selected from acetyl, formyl, pyroglutamyl, fatty acids, preferably capronic acid, urea, carbamate, sulfonamide or alkylamine, preferably said Cap is selected from amides, fatty acids as capronic acid and acetyl.

According to the present invention, said linker, biomolecule or Cap in formula (IV) can be the same or different each other.

In a further preferred embodiment of the present invention the Linker of formula (IV) is selected from 4-aminobutyric acid, beta-alaninine, 2-aminoethoxy-acetic acid, 5-aminovaleric acid or trioxatridecan-succinamic acid.

Preferably, when the linker is attached on one amino acid Lysine, said linker is selected from NHS-ester, isocyanates, benzoyl fluorides or carbamates.

A seventh object of the present invention is a pharmaceutical composition comprising said peptide, dimer or a bioconjugate according to the objects of the invention, as described above, and at least one pharmaceutically acceptable excipient.

The pharmaceutical composition of the present invention can be formulated in a form that is suitable for topical or ophthalmic administration.

Preferably, when the administration of the pharmaceutical composition of the invention is performed by topical route, the pharmaceutical form is selected from cream, ointment, gel, salve, solution, washing, suspension, drops, buffer (buffer solution), suspension, eye drops, drops, spray, wipe, or powder, preferably it is selected from cream, gel, spray, or ointment.

Among the ophthalmic administration, the pharmaceutical form is preferably selected from eye drops, ophthalmic gels, ointments, wash, wipe, spray or cream.

According to a particular embodiment the peptides or bioconjugates of the present invention are administered locally by using microparticles or nanoparticles.

According to the invention, the pharmaceutical composition of the present invention can be administered to animals and humans, defined as adults and as "paediatric population", wherein with the term "pediatric population" is indicated the part of the population from birth to eighteen years of age.

An eighth object of the present invention is the above described peptide, dimer or bioconjugate according to the invention for use in the treatment and/or prevention of an inflammatory and autoimmune disease.

A ninth object of the invention is a method for the treatment and/or prevention of an inflammatory and autoimmune disease, comprising administering to a patient in need thereof a therapeutically effective amount of the above described peptide, dimer or bioconjugate according to the invention.

Preferably, said inflammatory and autoimmune disease is selected from rheumatoid arthritis, multiple sclerosis, Crohn's disease, systemic lupus erythematosus, asthma, Behçet's disease, hyper IgE syndrome, ankylosing spondylitis, psoriasis, psoriatic arthritis, rheumatoid arthritis, keratoconjunctivitis sicca, vernal keratoconjunctivitis, stromal herpetic keratitis, corneal allograft rejection, corneal infections, preferably herpes virus and *Pseudomonas aeruginosa* keratitis, and dry eye disease. More preferably said disease is an autoimmune ophthalmic or dermatological disease, even more preferably it is dry eye disease or psoriasis.

All of the above specified diseases and medical conditions have in common that their origin and/or symptoms are IL-17A and/or Th-17-related.

More specifically for the latter, dry eye disease (DED), a highly prevalent condition that includes a wide spectrum of ocular surface disorders, ocular mucosal inflammation is a peculiar characteristic potentially leading to vision loss if uncontrolled, due to inflammation-induced corneal ulceration and scarring. In the progression of DED, pathogenic immune cells, predominantly Th17 cells continuously migrate to the ocular mucosal surface and secrete pro-inflammatory mediators, including IL17, causing ocular surface inflammation and epitheliopathy.

The peptides, dimers or bioconjugates of the invention are conveniently and preferably administered topically as eye drops or ophthalmic gels and ointments.

In a further embodiment, the peptide, dimer or bioconjugate for use according to the present invention, are administered as the only active principle or in combination with further active principles, and/or in combination with medical devices for the symptomatic treatment of ophthalmic conditions including but not limited to DED, e.g. ocular lubricants or "artificial tears", topical re-epithelizing agents, therapeutic contacts lenses and punctum plugs.

Preferably, said further active principle is an adjuvant, immunosuppressive agent, immunomodulating agent or anti-inflammatory agent.

For example, the IL-17A binding peptide of the present invention may be used in combination with DMSO.

According to a preferred embodiment, the IL-17A binding peptide of the present invention may be used in combination with immunosuppressive monoclonal antibodies, such as monoclonal antibodies with affinity to leukocyte receptors, selected from MHC, CD2, CD3, CD4, CD7, CD8, CD25, CD28, CD40, CD45, CD58, CD80, CD86 or their ligands; other immunomodulatory compounds, preferably a recombinant binding molecule having at least a portion of the extracellular domain of CTLA4 or a mutant thereof, an at least extracellular portion of CTLA4 or a mutant thereof joined to a non-CTLA4 protein sequence. e.g. (e.g. CTLA41 g, designated ATCC 68629) or a mutant thereof, e.g. LEA29Y; adhesion molecule inhibitors, LFA-I antagonists, ICAM-1 or -3 antagonists. VCAM-4 antagonists or VLA-4 antagonists.

In a further preferred embodiment the IL-17A binding peptide of the present invention is used in combination with DMARD (disease-modifying antirheumatic drug), preferably Gold salts, sulphasalazine, anti-malarias, methotrexate, D-penicillamine, azathioprine, mycophenolic acid, cyclosporine A, tacrolimus, sirolimus, minocycline, leflunomide, glucocorticoids; a calcineurin inhibitor, preferably cyclosporin A or FK 506; a modulator of lymphocyte recirculation, preferably FTY720 and FTY720 analogs; a mTOR inhibitor, preferably rapamycin, 40-O-(2-hydroxyethyl)-rapamycin, CCI779, ABT578, AP23573 or TAFA-93; an ascomycin having immuno-suppressive properties, preferably ABT-281, ASM981; corticosteroids; cyclophosphamide; azathioprene; methotrexate; leflunomide; mizoribine; mycophenolic acid; mycophenolate mofetil; 15-deoxyspergualine or an immunosuppressive homologue, analogue or derivative thereof; or a chemotherapeutic agent, preferably paclitaxel, gemcitabine, cisplatinum, doxorubicin or 5-fluorouracil; anti-TNF agents, preferably monoclonal antibodies to TNF, preferably infliximab, adaiimumab, CDP870, or receptor constructs to TNF-RI or TNF-RII, preferably Etanercept, PEG-TNF-RI; blockers of proinflammatory cytokines, IL-1 blockers, preferably Anakinra or IL-1 trap, AAL160, ACZ 885, IL-6 blockers; inhibitors or activators of proteases, preferably metalloproteases, anti-IL-15 antibodies, anti-IL-6 antibodies, anti-IL-23 antibodies, anti-IL-22 antibodies, anti-IL-21 antibodies, anti-IL-12 antibodies, anti-IFN-gamma antibodies, anti-IFN-alpha antibodies, anti-CD20 antibodies, anti-inflammatory agents, preferably aspirin or an anti-infectious agent. Naturally, this list of agents for co-administration is not limiting nor complete.

A further object of the present invention is one the peptides listed in Table 6 for use in the treatment and/or prevention of an inflammatory and autoimmune disease described above.

TABLE 6

| SEQ ID NO: | SEQUENCE |
|---|---|
| SEQ ID NO: 1 | IHVTIPADLWDWINK |
| SEQ ID NO: 66 | IVVTMPADLWDWIKA |
| SEQ ID NO: 67 | IVVTMPADLWDWIRA |
| SEQ ID NO: 68 | IVVTMPADLWDWIRK |
| SEQ ID NO: 69 | IVVTMPADLWDWIAA |
| SEQ ID NO: 70 | IVVTMPADLWDWARA |
| SEQ ID NO: 71 | IVVTMPADLWAWIRA |
| SEQ ID NO: 72 | IVVTMPADLADWIRA |
| SEQ ID NO: 73 | IVVTMPADAWDWIRA |
| SEQ ID NO: 74 | IVVTMPADLWDWIRA |
| SEQ ID NO: 75 | IVVTAPADLWDWIRA |
| SEQ ID NO: 76 | IVVAMPADLWDWIRA |
| SEQ ID NO: 77 | IAVTMPADLWDWIRA |
| SEQ ID NO: 78 | AVVTMPADLWDWIRA |
| SEQ ID NO: 79 | IHVTMPADLWDWIRA |
| SEQ ID NO: 80 | IQVTMPADLWDWIRA |
| SEQ ID NO: 81 | IRVTMPADLWDWIRA |
| SEQ ID NO: 82 | ITVTMPADLWDWIRA |
| SEQ ID NO: 83 | IWVTMPADLWDWIRA |
| SEQ ID NO: 84 | IYVTMPADLWDWIRA |
| SEQ ID NO: 85 | IVVTIPADLWDWIRA |
| SEQ ID NO: 86 | IVVTLPADLWDWIRA |
| SEQ ID NO: 87 | IVVTVPADLWDWIRA |
| SEQ ID NO: 88 | IVVTMPADLWDWIMA |
| SEQ ID NO: 89 | IVVTMPADLWDWINA |
| SEQ ID NO: 90 | IVVTMPADLWDWIQA |
| SEQ ID NO: 91 | IVVTIPADLWDWIRA |
| SEQ ID NO: 92 | IVVTLPADLWDWIRA |
| SEQ ID NO: 93 | IHVTIPADLWDWINK |
| SEQ ID NO: 94 | IHVTIPADLWDWIN |
| SEQ ID NO: 95 | IHVTIPADLWDWI |
| SEQ ID NO: 96 | DSSAVCWAFPHHPLCHMKAT |
| SEQ ID NO: 97 | ADADMCWFFPTSPWCH |
| SEQ ID NO: 98 | DLSAVCWAFPWDPECHM |
| SEQ ID NO: 99 | DSSAVCWAFPYLPECH |
| SEQ ID NO: 100 | DISAVCWAFPFDPECH |

TABLE 6-continued

| SEQ ID NO: | SEQUENCE |
|---|---|
| SEQ ID NO: 101 | AYECPRLEYDMFGALHCLPS |
| SEQ ID NO: 102 | CPRLEYDMFGALHCL |
| SEQ ID NO: 103 | CLDLQYDPWGALHCI |
| SEQ ID NO: 104 | CFDLQYDPWGALHCI |
| SEQ ID NO: 105 | CLDLQYDMFGALHCV |
| SEQ ID NO: 106 | CLDLVYDPWGALHCI |
| SEQ ID NO: 107 | CWVLEYDMFGALHCR |
| SEQ ID NO: 108 | CWALEYDMFGYLHCR |
| SEQ ID NO: 109 | CWVLEYDMFGFLHCR |
| SEQ ID NO: 110 | CWVLEYDMFGYLHCR |

The amount and mode of administration of the peptides according to the present invention will vary depending upon the particular peptide inhibitor of the invention, the individual patient group or patient, the presence of further medically active compounds and the nature and severity of the condition being treated.

According to a preferred embodiment, the prophylactic and/or therapeutic use dosages is of about 5-50 µg/ml, preferably of about 10-25 µg/ml Preferably, the frequency of administration for prophylactic and/or therapeutic uses lies in the range of about once to twice daily applications, preferably once.

The invention is further described by way of illustration in the following examples, none of which are to be interpreted as limiting the scope of the invention as outlined in the appended claims.

EXAMPLES

Example 1 Peptides Synthesis & Purification

We have developed a homology model of IL-17A by use of crystallographic data available (PDB 5 h13, PDB 5vb9 and PDB 4hsa) (Liu et al. Nat Commun 2013. 4, 1888, Liu et al. Sci Rep 2016, 6: 30859, Liu et al. Sci Rep 2016, 6, 26071, Ting, Tung et al. Plos One 2018, 13(1): e01908502018). In our models we have also recreated the loops unresolved in the crystals and optimized models through a molecular dynamics simulation performed with Desmond software, as implemented in Schrodinger Maestro macromodel suite. All molecular simulations were run for 1 microsecond to guarantee the system stability.

Based on structure and properties of IL-17A α-pocket, different peptide sequences have been designed so as to obtain i) a stable secondary and tertiary conformation that engages IL-17A with an optimized protein binding site occupancy, and ii) physical-chemical properties suitable for topical use in ophthalmic and dermatological pathologies (Liu et al. Nat Commun 2013, 4, 1888, Espada et al J Med Chem 2016, 59(5), 2255-2260).

Additionally, we optimized the interactions ligand-IL-17A by the introduction of hydrogen bonds and optimization of hydrophobic interactions.

a. Fmoc-Based Solid-Phase Peptide Synthesis

All the chemicals were purchased and used without further purification.

Peptides of SEQ ID NO: 1 to 43 and 111-257 of Table 1 were prepared by manual or automatic solid-phase peptide synthesis, on Rink Amide-MBHA resin as the solid support, as described below and with N-terminal amine capped with acetyl group.

The Fmoc (9-fluorenylmethoxycarbonyl) group used for Nα-protection was cleaved by 8 min treatment with 20% piperidine in dimethylformamide (DMF) followed by a further treatment with the same reagent for 10 min. After Fmoc cleavage, the peptide-resin complex was washed with DMF (×6). The next residue was then incorporated through the use of 1-[bis(dimethylamino)methylene]-1H-1,2,3-triazolo[4,5-b]pyrdinium3-oxid hexafluorophosphate (HATU)/N,N-diisopropylamine (DIPEA) coupling protocol [Fmoc-amino acid (3 equiv), HATU (3 equiv), and DIPEA (6 equiv)]. After gentle stirring (1 hr) and washing with DMF (×6), part of the peptide-resin was analyzed by Kaiser test. On completion of the assembly, the peptide-resin was washed with DMF (×3), dichloromethane (DCM) (×4) and then dried in vacuo.

Cleavage and Deprotection

The peptide was cleaved from the resin and, when necessary, deprotected by using as cleavage solution a mixture of trifluoroacetic acid/1,2-ethanedithiol/thioanisole/phenol/H2O/triisopropylsilane in the ratio 68.5/10/10/5/3.5/1, v/v. 3 ml of cleavage solution was used per 100 mg of resin. Complete deprotection was achieved under stirring for 4 hours at 30° C. Following the cleavage reaction, the peptide in the mixture was precipitated in cold diethyl ether and dried in vacuo at 50° C.

b. Disulfide Bond Formation in Peptide 41

Disulfide bond formation in peptide of SEQ ID NO: 41 of Table 1 was obtained by incubation of the peptide in a mixture DMSO/H2O (20/80, v/v), which was monitored by RP-HPLC, MS and free sulfhydryl detection (DTNB method).

c. Purification by Preparative RP-HPLC and Purity Assessment by Analytical HPLC

The crude peptide samples were purified by preparative RP-HPLC (Agilent) using a C18 column (10 μm, 100 Å, 50×250 mm). A solvent system consisting of solvent A (0.1% TFA, 2% CH3CN in water) and solvent B (90% CH3CN/H2O) at a flow rate of 25 mL/min was used for elution, and the absorbance was detected at 220 nm. The solvent was removed by lyophilization. The final products were characterized by MALDI-TOF-MS, and the purity of the material assessed by analytical RP-HPLC (C18-250 mm×4.6 mm I.D., flow rate of 1 mL/min), and the absorbance was detected at 220 nm.

Example 2: Preparation of NAM and/or NAG Bioconjugated Peptides BIO-1, BIO-2 and BIO-3

The bioconjugated peptides BIO-1, BIO-2 and BIO-3 were prepared by a conjugation reaction of peptide 42 or 43 according the following procedures.

1. Preparation of Donor and Acceptor

All reactions were performed under $N_2$ atmosphere. NMR spectra were run on a Brucker 400 MHz instrument. HPLC-UV analysis were obtained on an Agilent 1260 Infinity System, equipped with a G1311B Agilent 1260 quaternary pump, G1329B Agilent 1260 autosampler, G1315C Agilent 1260 diode array detector, and G1316A Agilent 1260 column thermostat modules. A Phenomenex GEMINI C18 150×4.6 mm2 (5 μm) column was used. The mobile phase A was MilliQ water with 0.05% TFA, and B was HPLC grade acetonitrile with 0.05% TFA at a flow rate of 1.0 mL/min. The HPLC system was coupled to an Agilent Quadrupole 6120 LC/MS mass spectrometer operated in positive ion mode. Ions were generated using an electrospray ionization ion source. Acquisition data were processed with Agilent Chemstation Software.

a. Synthesis of 1-(2,2,2-Trichloroacetimine)2-deoxy-3-O-acetyl-4,6-Obenzylidene-2-(2,2,2-tri-chloroethoxycarbonylamino)-a-D-glucopyranoside (Donor)

Trichloroethoxycarbonyl chloride (2.1 mL, 15.3 mmol) was added dropwise at room temperature to a vigorously stirred solution of D-glucosamine hydrochloride (3 g, 13.9 mmol) and NaHCO3, (3.5 g, 41.7 mmol) in water (30 mL). The mixture was stirred for 2 h, then neutralized with 1 M HCl, concentrated, and dried in vacuo. 2-deoxy-2-(2,2,2-trichloroethoxycarbonylamino)-a-D-glucopyranoside (intermediate A) was obtained.

The crude product obtained was directly used for the next reaction step without further purification.

In details, zinc chloride (1.9 g, 13.9 mmol) was added to a solution of intermediate A (4.9 g, 13.9 mmol) in benzaldehyde (24 ml) and molecular sieves, 4 Å (4 Å MS, 600 mg). After stirring overnight at room temperature, saturated aq NaHCO3 (30 mL) and diethyl ether (90 mL) were added and the reaction mixture was stirred for 15 min. The formed precipitate was filtered, washed with water, diethyl ether, and dried. The residue was dissolved in pyridine (13 mL) cooled to 0° C., treated with acetic anhydride (6.4 mL, 68 mmol) and stirred overnight at room temperature, then the solution was concentrated with toluene, cooled to 0° C. and extracted with DCM and saturated aq NaHCO3 (3×), then washed with a saturated NaCl solution. The combined organic layers were dried, concentrated, and the crude purified by Isolera (EtPet/EtOAc) to give 1,3-di-O-acetyl 2-deoxy-4,6-O-benzylidene-2-(2,2,2-trichloroethoxycarbonylamino)-a-D-glucopyranoside (intermediate B), as a white solid (3.05 g, 41.7% yield).

Morpholine (1.2 mL, 13.9 mmol) was then added to a solution of intermediate B (3.05 g, 5.8 mmol) in dry ethyl acetate (EtOAc) (12.2 mL). After stirring overnight at room temperature the reaction mixture was quenched with 3N HCl solution (3.5 mL) and then stirred for 20 min. Extracted with EtOAc and washed with water, saturated aq NaHCO3 and a saturated NaCl solution a saturated NaCl solution, dried, and concentrated. The crude was purified by Isolera (EtPet/EtOAc) to give 2-deoxy-3-O-acetyl-4,6-O-benzylidene-2-(2,2,2-trichloroethoxycarbonylamino)-a-D-glucopyranoside (intermediate C) as a white solid (2.2 g, 78.4%). To a solution of intermediate C (2.2 g, 4.54 mmol) in dry DCM (44 ml), Cs2CO3 (680 mg, 2.1 mmol) and CCl3CN (4.4 mL, 43.8 mmol) were added. The reaction mixture was stirred for 2 h at room temperature, then filtered over celite and concentrated to give 1-(2,2,2-Trichloroacetimine)2-deoxy-3-O-acetyl-4,6-Obenzylidene-2-(2,2,2-trichloroethoxycarbonylamino)-a-D-glucopyranoside (Donor) as a light yellow solid (2.2 g, 77%).

b. Synthesis of 1,6-DI-O-benzyl 2-deoxy-3-O—((R)-10-ethoxycarbonylethyl)-2-(2,2,2-trichloroethoxycarbonylamino)-a-D-glucopyranoside (Acceptor)

Allyl chloroformate (6.6 mL, 62.2 mmol) was added dropwise at room temperature to a vigorously stirred solution of D-glucosamine hydrochloride (12.2 g, 56.6 mmol) and NaHCO3, (14.3 g, 169.7 mmol) in water (61 mL). The mixture was stirred for 2 h, then neutralized with 1M HCl, concentrated, and dried in vacuo. Crude 2-deoxy-2-(allyloxycarbonylamino)-a-D-glucopyranoside (Intermediate D) was obtained. The product was used for next reaction step without further purification, Intermediate D (14.9 g, 56.6 mmol) was dissolved in benzyl alcohol (89 mL, and acetyl chloride (15.4 mL, 215.2 mmol) was added dropwise at 0° C. After stirring for 3 h at 80° C. the reaction mixture was quenched with cold saturated aq $NaHCO^3$ (20 ml) and stirred for additional 30 min. Cold water and diethyl ether were added and the reaction mixture was stirred for 30 min. The two phases were separated, and the aqueous phase was concentrated, and dried in vacuo. 30 ml of water and 200 ml of ethyl ether were added until the formation of a precipitate that was filtered and washed several times with cold diethyl ether (until no traces of benzyl alcohol were detected. Benzyl 2-deoxy-2-(allyloxycarbonylamino)-a-D-glucopyranoside (intermediate E) was obtained as a white solid (11 g, 55%) and directly used for next reaction step without further purification. Zinc chloride (4.2 g, 31.1 mmol) was added to a solution of intermediate E (11 g, 31.1 mmol) in benzaldehyde (55 mL) and 4 Å MS (4.9 g). After 2 h, more zinc chloride (4.2 g, 31.1 mmol) was added. After stirring overnight at room temperature, the reaction mixture was treated with saturated aq $NaHCO_3$ (70 mL), petroleum ether (420 mL), and stirred for 10 min. The precipitate was filtered, washed with petroleum ether and dissolved in DCM. The organic solution was extracted with saturated aq $NaHCO_3$, water, and a saturated NaCl solution dried and concentrated. The crude was purified by Isolera (DCM/EtOAc) to give Benzyl 2-deoxy-4,6-O-benzylidene-2-(allyloxycarbonylamino)-a-D-glucopyranoside (intermediate F) as a white solid (2.75 g, 20%).

To a solution of intermediate F (2.75 g, 6.2 mmol) in dry DCM (40.6 mL), cooled to 0° C., sodium hydride (NaH, 348.8 mg, 8.7 mmol, 60% oil dispersion) was added, and the mixture stirred for 30 min at room temperature. The mixture was then treated with neat (−)-ethyl (S)-2-trifluromethanesulfonyl propionate dropwise and stirred for 2 h at room temperature. The reaction mixture was quenched by addition of ice, and extracted with DCM. The organic solution was washed with saturated aq $NaHCO_3$, a saturated NaCl solution, dried and concentrated. The residue was purified by Isolera (DCM/EtOAc) to give benzyl 2-deoxy-3-O—((R)-10-ethoxycarbonylethyl)-4,6-Obenzylidene-2-(allyloxy-carbonylamino)-a-D-glucopyranoside (intermediate G) as a white solid (2.35 g, 69.7%).

Tetrakis(triphenylphosphine) palladium (1.5 g, 1.3 mmol) and acetic acid (AcOH, 0.385 mL, 6,725 mmol) were added to a solution of the intermediate G (2.35 g, 4.34 mmol) in dry DCM (42.7 mL). The reaction mixture was stirred at room temperature for 15 min and then 2,2,2-trichloroethyl chloroformate (TrocCl, 1.224 mL, 8,895 mmol) was added dropwise, and the resulting solution stirred for 1 h at room temperature. The reaction mixture was quenched with saturated aq $NaHCO_3$, extracted with DCM, washed with $H_2O$ and a saturated NaCl solution. After concentration in vacuo, the residue was dissolved in diethyl ether (100 ml) and insoluble materials filtered off. The organic phase was dried, concentrated, and purified by Isolera (Cyclohexane/AcOEt) to give benzyl 2-deoxy-3-O—((R)-10-ethoxycarbonylethyl)-4,6-O-benzylidene-2-(2,2,2-tri-chloroethoxycarbonylamino)-a-D-glucopyranoside (intermediate H) as a white solid (2.3 g, 83.7%).

To a solution of intermediate H (2.4 g, 3.8 mmol) in dry $CH_3CN$ (38 mL) at 0° C. a solution of $Me_3N$—$BH_3$ (332 mg, 4.55 mmol) in $CH_3CN$ (2.2 mL) was added, followed by a solution of $BF_3$-$OEt_2$ (2.89 mL, 23.4 mmol) in $CH_3CN$ (8 mL) added dropwise. After stirring for 3 h at 0° C., the mixture was quenched with cold saturated aq $NaHCO_3$(30 mL), diluted with EtOAc (350 ml), and washed with saturated aq $NaHCO_3$ (100 ml), 5% citric acid (4×50 ml), saturated aq $NaHCO_3$ (50 mL), and a saturated NaCl solution (40 mL). The organic layer was dried, concentrated, and the crude was purified by Isolera (Cyclohexane/AcOEt) to give 1,6-di-O-benzyl 2-deoxy-3-O—((R)-10-ethoxycarbonylethyl)-2-(2,2,2-trichloroetho-xycarbonylamino)-a-D-glucopyranoside (Acceptor), as a colorless foam (1.2 g, 49.8%).

2. Synthesis of NAG-NAM Conjugated Peptide BIO-3

Donor (1.6 g, 2.6 mmol) and Acceptor (1.1 g, 1.73 mmol), suspended in dry DCM (55 mL) with 4 Å molecular sieves (200 mg), were treated with Trimethylsilyl trifluoromethanesulfonate (TMSOTf, 188 µL, 1.04 mmol) at −15° C. After stirring for 20 min, more 0.75 eq of Donor and 0.3 eq of TMSOTf were added. After stirring for 20 min, more 0.75 eq of Donor and 0.3 eq of TMSOTf were added. The mixture was then quenched with cold saturated aq solution of $NaHCO_3$ (15 mL) and extracted with DCM (60 mL). The organic layer was washed with saturated aq $NaHCO_3$ and a saturated NaCl solution, dried and concentrated. The residue was purified by Isolera reverse phase (H2O/ACN neutral phases) to give benzyl 6-O-benzyl-4-O-[2-deoxy-3-O-acetyl-4,6-Obenzylidene-2-(2,2,2-trichloroethoxycarbonylamino)-b-Dglucopyranosyl]-2-deoxy-3-O—[(R)-1'-ethoxycarbonyl ethyl]-2-(2,2,2-trichloroethoxycarbonylamino)-a-D-glucopyranoside (intermediate L), as a white foam (1.2 g, 62.9%).

A solution of intermediate L (1.2 g, 1.09 mmol) and zinc-copper couple (3.12 g, 24.2 mmol) in a mixture AcOH/Ac2O/THF 1:1:1 (12 mL) was stirred for 4 h at room temperature. The reaction mixture was filtered over celite, washed with EtOAc, and concentrated. The crude was concentrated and purified by column chromatography (Cyclohexane/AcOEt) to give benzyl 6-O-benzyl-4-O-[2-deoxy-3-O-acetyl-4,6-Obenzylidene-2-acetylamino-b-D-glucopyranosyl]-2-deoxy-3-O—[(R)-10-ethoxycarbonylethyl]-2-acetylamino-a-D-glucopyranoside (intermediate M) as a white solid (560 mg, 0.67 mmol, 61.6%). HPLC-MS (ESI+) m/z: $C_{44}H_{54}N_2O_{14}$+Na: 857.3472. Found: 857.6124.

To a solution of intermediate M (91 mg, 0.109 mmol) in THF/1,4-dioxane/$H_2O$ 4:2:1 (2.8 mL) was added $LiOH.H_2O$ (56 mg, 1.34 mmol). After stirring for 2 h at room temperature, the reaction mixture was filtered over Dowex H+ (freshly activated with 1N HCl). The residue was purified by diaion HP-20 column chromatography (2×7 cm) previously washed with water, MeOH and water. Column was eluted first with $H_2O$ (50 mL) and then with MeOH (30 mL). The alcohol fractions were concentrated to give benzyl 6-O-benzyl-4-O-[2-deoxy-4,6-O-benzylidene-2-acetylamino-b-D-glucopyranosyl]-2-deoxy-3-O—[(R)-10-ethoxycarbonylethyl]-2-acetylamino-a-D-glucopyranoside (intermediate N), as a whitish solid (57.4 mg, 69%). Mp 102-105° C., 1H NMR (600 MHz, $CD_3OD$) δH 7.51-7.27 (m, 15H, ArH), 5.59 (s, 1H, CHPh), 5.36 (d, J 3.1 Hz, H-1), 4.85 (m) $H_2O$, H-10, ½ $CH_2Ph$), 4.66-4.57 (m, 3H, J 12.1 Hz, $CHCH_3$, $CH_2$-Ph), 4.46 (d, 1H, J 12.2 Hz, ½ $CH_2Ph$), 4.29 (dd, 1H, J 10.3 Hz, J 5.0 Hz, H-60b), 4.07 (t, 1H, J 9.6 Hz, H-30), 3.95 (t, 1H, J 9.1 Hz, H-4), 3.82-3.77 (m, 2H, H-6b, H-3), 3.72-3.62 (m, 3H, H-60a, H-5, H-6a), 3.55-3.40 (m, 3H, H-20, H-40, H-2), 3.30-3.27 (m, 1H, H-50), 1.98 (s, 3H, $COCH_3$), 1.96 (s, 3H, $COCH_3$), 1.37 (d, J 6.9 Hz, 3H, $CHCH_3$). HPLC-MS (ESI+) m/z: $C_{40}H_{48}N_2O_{13}$+Na: 787.3054 Found: 787.7830.

The peptide of SEQ ID NO: 42 was coupled to compound N in the conditions used for amino acid coupling and the resulting bioconjugate was cleaved from the solid support by treatment with trifluoroacetic acid (1% solution in DCM). The resulting bioconjugate (0.026 mmol) was dissolved in acetic acid (8 mL), and Pd(OH)2/C (58 mg) was added. The resulting mixture was stirred at room temperature for 6 h under hydrogen atmosphere. The mixture was filtered over celite and concentrated to give the bioconjugate BIO-3 in quantitative yield. The bioconjugate was cleaved from the resin and the last residue deprotected by using as cleavage solution a mixture of trifluoroacetic acid/1,2-ethanedithiol thioanisole/phenol/H2O/triisopropylsilane in a ratio of 68.5/10/10/5/3.5/1, v/v. 3 ml of cleavage solution was used per 100 mg of resin. Complete deprotection was achieved after 4 hours at 30° C. Following the cleavage reaction, the crude peptide was precipitated by addition of cold diethyl ether and dried in vacuo at 50° C.

The crude bioconjugate was purified by preparative RP-HPLC (Agilent) using a C18 column (10 μm, 100 Å, 50×250 mm). A solvent mixture consisting of solvent A (0.1% TFA, 2% $CH_3CN$ in $H_2O$) and solvent B (90% $CH_3CN/H_2O$) at a flow rate of 25 mL/min was used for elution, and the absorbance detected at 220 nm. The solvent was removed by lyophilization and the final products characterized by MALDI-TOF-MS. The purity of the purified material was assessed by analytical RP-HPLC (C18-250 mm×4.6 mm I.D., flow rate of 1 mL/min), and the absorbance was detected at 220 nm.

3. Synthesis of NAG and NAM Bioconjugates BIO-1 and BIO-2

Synthesis of NAM-Peptide and Peptide-NAG were performed starting from the peptide anchored resin (Example 1), wherein the peptide was the peptide of SEQ ID NO: 42 (for BIO-1) or the peptide of SEQ ID NO: 43 (for BIO-2), respectively, and Donor and Acceptor were the molecules described above according the procedure described in Swaminathan et al., Proc Natl Acad Sci USA. 2006, 17; 103 (3):684-9.

Example 3: Synthesis of Capric Acid Bioconjugate BIO-4

Peptides capped with Capric Acid were synthetized according the procedure described in Example 1 by using a N-terminal amine capped with Capric Acid.

Example 4: Synthesis of Ascorbic Acid Bioconjugate BIO-5

5,6-O-isopropylidene-L-ascorbic acid (iASA) was synthesized by Jung's method (Jung, M. E.; Shaw, T. J. J. Am. Chem. Soc. 1980, 102. 6304). For the activation, CDI (10 eq.) was added to the peptide anchored resin for 2 h. Activation of N-terminal amine of peptide, after cleavage from the resin, was confirmed by RP-HPLC using the following conditions: A to B (A: 0.1% TFA in $H_2O$, B: 0.1% TFA in $CH_3CN$; from 0% to 60% B over 30 min, at a flow rate of 1.0 mL/min); detection, UV 230 nm. Next, iASA was introduced to the activated peptide anchored resin. The product was separated from the resin by treating with 50% TFA/DCM (v/v) for 1 h. The resin was filtered, the filtrate was concentrated in high vacuum, and precipitated with cold diethyl ether. The structure of the resulting bioconjugate BIO-5 was confirmed by LC/MS using 0.1% formic acid/methanol as eluent at a flow rate of 250 μL/min over 30 min, and monitored at 230 nm.

Example 5: IL-17RA/IL17RC Dimerization Assay in Response to IL-17 Å

The peptides of Table 7 were tested for their ability to inhibit the binding of IL-17 Å to its receptor and the subsequent interaction of IL-17RA and IL17RC.

Interleukin receptor RA and RC dimerization assay (DiscoverX) was used to measure the interaction of the receptor chains IL-17RA and IL17RC upon activation by IL-17 Å in the absence or presence of the peptides of Table 7.

In the PathHunter® Cytokine Receptor Assay, one cytokine receptor chain is tagged with a small peptide epitope ProLink (PK) and the other chain is tagged with Enzyme Acceptor (EA). Ligand binding induces dimerization of the two receptors, facilitating complementation of PK and EA fragments. This interaction generates an active unit of b-galactosidase, which is detected using a chemoluminescent substrate. PathHunter cell lines were expanded from freezer stocks according to standard procedures. Cells were seeded in a total volume of 20 μL into white walled, 384-well microplates and incubated for the appropriate time prior to testing. For agonist activity inhibition, cells were incubated with sample to induce response. Intermediate dilution of sample stocks was performed to generate 5× sample in assay buffer. 5 μL of 5× sample was added to cells and incubated at 37° C., or room temperature for 60 minutes. Vehicle concentration was 1%. 5 μL of 6× $EC_{50}$ agonist (IL-17 Å) in assay buffer was added to the cells and incubated at 37° C. for 6 to 16 hours depending on the assay. 1. Assay signal was generated through a single addition of 12.5 or 15 μL (50% v/v) of PathHunter Detection reagent cocktail for agonist (IL-17 Å) and (peptides of table 7) assays respectively, followed by a one hour incubation at room temperature. For some assays, activity was detected using a high sensitivity detection reagent (PathHunter Flash Kit) to improve assay performance. In these assays, an equal volume of detection reagent (25 or 30 uL) was added to the wells, followed by a one hour incubation at room temperature. Microplates were read following signal generation with a PerkinElmer Envision™ instrument for chemiluminescent signal detection. Compound activity was analyzed using CBIS data analysis suite (Cheminnovation, CA). % Inhibition=100%× (1−(mean RLU of test sample−mean RLU of vehicle control)/(mean RLU of EC80 control−mean RLU of vehicle control)).

As reported in Table 7 below, all tested molecules were found active in inhibiting IL-17RA/IL17RC dimerization thus inhibiting the IL-17 Å pathway activation showing a IC50 value in the mid nanomolar range.

TABLE 7

| SEQUENCE | NAME | $IC_{50}$ in IL-17RA/IL7RC dimerization assay |
|---|---|---|
| SEQ ID NO: 1 | | <0.2 μM |
| SEQ ID NO: 2 | | <0.2 μM |
| SEQ ID NO: 3 | | <0.4 μM |
| SEQ ID NO: 4 | | <0.1 μM |
| SEQ ID NO: 5 | | <0.1 μM |
| SEQ ID NO: 6 | | <0.4 μM |
| SEQ ID NO: 7 | | <0.1 μM |
| SEQ ID NO: 8 | | <0.2 μM |
| SEQ ID NO: 9 | | <0.3 μM |
| SEQ ID NO: 10 | | <0.4 μM |
| SEQ ID NO: 11 | | <0.4 μM |
| SEQ ID NO: 12 | | <0.2 μM |
| SEQ ID NO: 13 | | <0.4 μM |
| SEQ ID NO: 14 | | <0.4 μM |

TABLE 7-continued

| SEQUENCE | NAME | IC$_{50}$ in IL-17RA/IL7RC dimerization assay |
|---|---|---|
| SEQ ID NO: 15 | | <0.4 μM |
| SEQ ID NO: 16 | | <0.4 μM |
| SEQ ID NO: 17 | | <0.4 μM |
| SEQ ID NO: 18 | | <0.4 μM |
| SEQ ID NO: 19 | | <1 μM |
| SEQ ID NO: 20 | | <1 μM |
| SEQ ID NO: 21 | | <1 μM |
| SEQ ID NO: 22 | | <1 μM |
| SEQ ID NO: 23 | | <1 μM |
| SEQ ID NO: 24 | | <1 μM |
| SEQ ID NO: 25 | | <1 μM |
| SEQ ID NO: 26 | | <1 μM |
| SEQ ID NO: 27 | | <1 μM |
| SEQ ID NO: 28 | | <1 μM |
| SEQ ID NO: 29 | | <1 μM |
| SEQ ID NO: 30 | | <1 μM |
| SEQ ID NO: 31 | | <1 μM |
| SEQ ID NO: 32 | | <1 μM |
| SEQ ID NO: 33 | | <1 μM |
| SEQ ID NO: 34 | | <1 μM |
| SEQ ID NO: 35 | | <1 μM |
| SEQ ID NO: 36 | | <1 μM |
| SEQ ID NO: 37 | | <0.2 μM |
| SEQ ID NO: 38 | | <0.2 μM |
| SEQ ID NO: 39 | | <0.2 μM |
| SEQ ID NO: 40 | | <0.2 μM |
| SEQ ID NO: 41 | | <0.5 μM |
| SEQ ID NO: 111 | | <0.5 μM |
| SEQ ID NO: 112 | | <0.5 μM |
| SEQ ID NO: 113 | | <0.5 μM |
| SEQ ID NO: 114 | | <0.5 μM |
| SEQ ID NO: 115 | | <0.5 μM |
| SEQ ID NO: 116 | | <0.5 μM |
| SEQ ID NO: 117 | | <0.5 μM |
| SEQ ID NO: 118 | | <0.5 μM |
| SEQ ID NO: 119 | | <0.5 μM |
| SEQ ID NO: 120 | | <0.5 μM |
| SEQ ID NO: 121 | | <0.5 μM |
| SEQ ID NO: 122 | | <0.5 μM |
| SEQ ID NO: 123 | | <0.5 μM |
| SEQ ID NO: 124 | | <0.5 μM |
| SEQ ID NO: 125 | | <0.5 μM |
| SEQ ID NO: 126 | | <0.5 μM |
| SEQ ID NO: 127 | | <0.5 μM |
| SEQ ID NO: 128 | | <0.5 μM |
| SEQ ID NO: 129 | | <0.5 μM |
| SEQ ID NO: 130 | | <0.5 μM |
| SEQ ID NO: 131 | | <0.5 μM |
| SEQ ID NO: 132 | | <0.5 μM |
| SEQ ID NO: 133 | | <0.5 μM |
| SEQ ID NO: 134 | | <0.5 μM |
| SEQ ID NO: 135 | | <0.5 μM |
| SEQ ID NO: 136 | | <0.5 μM |
| SEQ ID NO: 137 | | <0.5 μM |
| SEQ ID NO: 138 | | <0.5 μM |
| SEQ ID NO: 139 | | <0.5 μM |
| SEQ ID NO: 140 | | <0.5 μM |
| SEQ ID NO: 141 | | <0.5 μM |
| SEQ ID NO: 142 | | <0.5 μM |
| SEQ ID NO: 143 | | <0.5 μM |
| SEQ ID NO: 144 | | <0.5 μM |
| SEQ ID NO: 145 | | <0.5 μM |
| SEQ ID NO: 146 | | <0.5 μM |
| SEQ ID NO: 147 | | <0.5 μM |
| SEQ ID NO: 148 | | <0.5 μM |
| SEQ ID NO: 149 | | <0.5 μM |
| SEQ ID NO: 150 | | <0.5 μM |
| SEQ ID NO: 151 | | <0.5 μM |
| SEQ ID NO: 152 | | <0.5 μM |
| SEQ ID NO: 153 | | <0.5 μM |
| SEQ ID NO: 154 | | <0.5 μM |
| SEQ ID NO: 155 | | <0.5 μM |
| SEQ ID NO: 156 | | <0.5 μM |
| SEQ ID NO: 157 | | <0.5 μM |
| NAM-IMVTIPADLYEWIEE (NAM plus SEQ ID NO: 42) | BIO-1 | <1 μM |
| IMVTIPADLYEWIEEQ-NAG (SEQ ID NO: 42 plus NAG) | BIO-2 | <1 μM |
| NAG-NAM-IMVTIPADLYEWIEE (NAG-NAM plus SEQ ID NO: 42) | BIO-3 | <1 μM |
| capric acid-IMVTIPADLYEWIEE (capric acid plus SEQ ID NO: 42) | BIO-4 | <1 μM |
| Ascorbic acid – IMVTIPADLYEWIEE (Ascorbic acid plus SEQ ID NO: 42) | BIO-5 | <1 μM |
| SEQ ID NO: 158 | | <10 μM |
| SEQ ID NO: 159 | | <10 μM |
| SEQ ID NO: 160 | | <10 μM |
| SEQ ID NO: 161 | | <10 μM |
| SEQ ID NO: 162 | | <10 μM |
| SEQ ID NO: 163 | | <10 μM |
| SEQ ID NO: 164 | | <10 μM |
| SEQ ID NO: 165 | | <10 μM |
| SEQ ID NO: 166 | | <10 μM |
| SEQ ID NO: 167 | | <10 μM |
| SEQ ID NO: 168 | | <10 μM |
| SEQ ID NO: 169 | | <10 μM |
| SEQ ID NO: 170 | | <10 μM |
| SEQ ID NO: 171 | | <10 μM |
| SEQ ID NO: 172 | | <10 μM |
| SEQ ID NO: 173 | | <10 μM |
| SEQ ID NO: 174 | | <10 μM |
| SEQ ID NO: 175 | | <10 μM |
| SEQ ID NO: 176 | | <10 μM |
| SEQ ID NO: 177 | | <10 μM |
| SEQ ID NO: 178 | | <10 μM |
| SEQ ID NO: 179 | | <10 μM |
| SEQ ID NO: 180 | | <10 μM |
| SEQ ID NO: 181 | | <10 μM |
| SEQ ID NO: 182 | | <10 μM |
| SEQ ID NO: 183 | | <10 μM |
| SEQ ID NO: 184 | | <10 μM |
| SEQ ID NO: 185 | | <10 μM |
| SEQ ID NO: 186 | | <10 μM |
| SEQ ID NO: 187 | | <10 μM |
| SEQ ID NO: 188 | | <10 μM |
| SEQ ID NO: 189 | | <10 μM |
| SEQ ID NO: 190 | | <10 μM |
| SEQ ID NO: 191 | | <10 μM |
| SEQ ID NO: 192 | | <10 μM |
| SEQ ID NO: 193 | | <10 μM |
| SEQ ID NO: 194 | | <10 μM |
| SEQ ID NO: 195 | | <10 μM |
| SEQ ID NO: 196 | | <10 μM |
| SEQ ID NO: 197 | | <10 μM |
| SEQ ID NO: 198 | | <10 μM |
| SEQ ID NO: 199 | | <10 μM |
| SEQ ID NO: 200 | | <10 μM |
| SEQ ID NO: 201 | | <10 μM |
| SEQ ID NO: 202 | | <10 μM |
| SEQ ID NO: 203 | | <10 μM |
| SEQ ID NO: 204 | | <10 μM |
| SEQ ID NO: 205 | | <10 μM |
| SEQ ID NO: 206 | | <10 μM |
| SEQ ID NO: 207 | | <10 μM |
| SEQ ID NO: 208 | | <10 μM |
| SEQ ID NO: 209 | | <10 μM |
| SEQ ID NO: 210 | | <10 μM |
| SEQ ID NO: 211 | | <10 μM |
| SEQ ID NO: 212 | | <10 μM |
| SEQ ID NO: 213 | | <10 μM |
| SEQ ID NO: 214 | | <10 μM |
| SEQ ID NO: 215 | | <10 μM |
| SEQ ID NO: 216 | | <10 μM |
| SEQ ID NO: 217 | | <10 μM |
| SEQ ID NO: 218 | | <10 μM |
| SEQ ID NO: 219 | | <10 μM |
| SEQ ID NO: 220 | | <10 μM |
| SEQ ID NO: 221 | | <10 μM |
| SEQ ID NO: 222 | | <10 μM |
| SEQ ID NO: 223 | | <10 μM |

TABLE 7-continued

| SEQUENCE | NAME | IC$_{50}$ in IL-17RA/IL7RC dimerization assay |
|---|---|---|
| SEQ ID NO: 224 | | <10 µM |
| SEQ ID NO: 225 | | <10 µM |
| SEQ ID NO: 226 | | <10 µM |
| SEQ ID NO: 227 | | <10 µM |
| SEQ ID NO: 228 | | <10 µM |
| SEQ ID NO: 229 | | <10 µM |
| SEQ ID NO: 230 | | <10 µM |
| SEQ ID NO: 231 | | <10 µM |
| SEQ ID NO: 232 | | <10 µM |
| SEQ ID NO: 233 | | <10 µM |
| SEQ ID NO: 234 | | <10 µM |
| SEQ ID NO: 235 | | <10 µM |
| SEQ ID NO: 236 | | <10 µM |
| SEQ ID NO: 237 | | <10 µM |
| SEQ ID NO: 238 | | <10 µM |
| SEQ ID NO: 239 | | <10 µM |
| SEQ ID NO: 240 | | <10 µM |
| SEQ ID NO: 241 | | <10 µM |
| SEQ ID NO: 242 | | <10 µM |
| SEQ ID NO: 243 | | <10 µM |
| SEQ ID NO: 244 | | <10 µM |
| SEQ ID NO: 245 | | <10 µM |
| SEQ ID NO: 246 | | <10 µM |
| SEQ ID NO: 247 | | <10 µM |
| SEQ ID NO: 248 | | <10 µM |
| SEQ ID NO: 249 | | <10 µM |
| SEQ ID NO: 250 | | <10 µM |
| SEQ ID NO: 251 | | <10 µM |
| SEQ ID NO: 252 | | <10 µM |
| SEQ ID NO: 253 | | <10 µM |
| SEQ ID NO: 254 | | <10 µM |
| SEQ ID NO: 255 | | <10 µM |
| SEQ ID NO: 256 | | <10 µM |
| SEQ ID NO: 257 | | <10 µM |

In FIG. 1, a dose-response profile for exemplary peptides is reported.

Example 6: Phenotipic Assay in Human Differentiated TH17 Cells and Viability Assay To evaluate the effect of the peptides of the invention on the target cells responsible for inflammation in ophthalmic or dermatological pathologies, we tested the ability of the peptide of SEQ ID NO: 18 to inhibit in vitro pro-inflammatory cytokines and metalloproteinases secretion by human Th17 cells.

Human primary CD4 T-cells were differentiated into Th17 cells in vitro by culturing the cells in Th17 differentiation medium for 10 days. In details, purified human peripheral blood CD4 T-cells were cultured in Th-17 differentiation medium (CellXVivo Human Th17, Tocris) per manufacturer's instructions. Briefly: 96-well tissue culture plates were coated with anti-CD3 and CD28 agonistic antibodies. Cells were counted via trypan blue exclusion and suspended at a concentration of 1E5 cells/ml in Th-17 differentiation medium. 0.2 mL of this suspension was plated into individual wells of a 96-well plate. Cells were incubated at 37° C. with 5% C02 for 10 days, with media replaced as needed. Following 10-day Cell Differentiation, the peptides synthetized in Example 1, such as the peptide of Seq. ID No 18, were diluted to the appropriate concentration in CGM (cell growth medium, XVivo-15, Lonza). Cell plate was centrifuged at 300×g for 5 min, and Th17 differentiation medium was removed.

Following differentiation, the cells were stimulated with both an activation cocktail containing Phorbol 12-myristate 13-acetate and Ionomycin in the presence of varying concentrations of test articles.

At 24 h following stimulation, culture supernatants were analyzed for expression of IL-17, IL-6, IL-23, MMP3 and examined for viability using the fluorescence viability dye, Alamar blue. The CD4 cells secreted high levels of IL-17 Å in response to stimulation with an activation cocktail, indicating successful differentiation into Th17 cells. Additionally, stimulated cells secreted IL-6, IL23 and MMP3.

Supernatant was removed and replaced with 200 µL of diluted peptide or vehicle (CGM+DMSO diluted as with TI concentration) in appropriate groups. Cells were incubated with peptide test items for 1 hour before stimulation. The following stimulation solutions were generated: 10× Cell Activation Cocktail: Diluted from 500× to 10× working solution in CGM. 22 µL of appropriate stimulants were added to wells 1 hr after TI addition. Finally, 25 µL of Alamar blue reagent (10×) was added to each well 20 hours after stimulant (4 hrs prior to 24 hr serum collection) to determine cell viability. 24 hrs. After Stimulant, Alamar blue fluorescence was measured per manufacturer's instructions. Remaining Supernatants were collected for subsequent multiplex protein analyses. Expression levels of IL-6, IL-17, and IL-23 as well as MMP3 in 24 hour stimulated culture supernatants was evaluated using a Luminex Multiplex Platform on a MAGPIX instrument.

Figure 2:
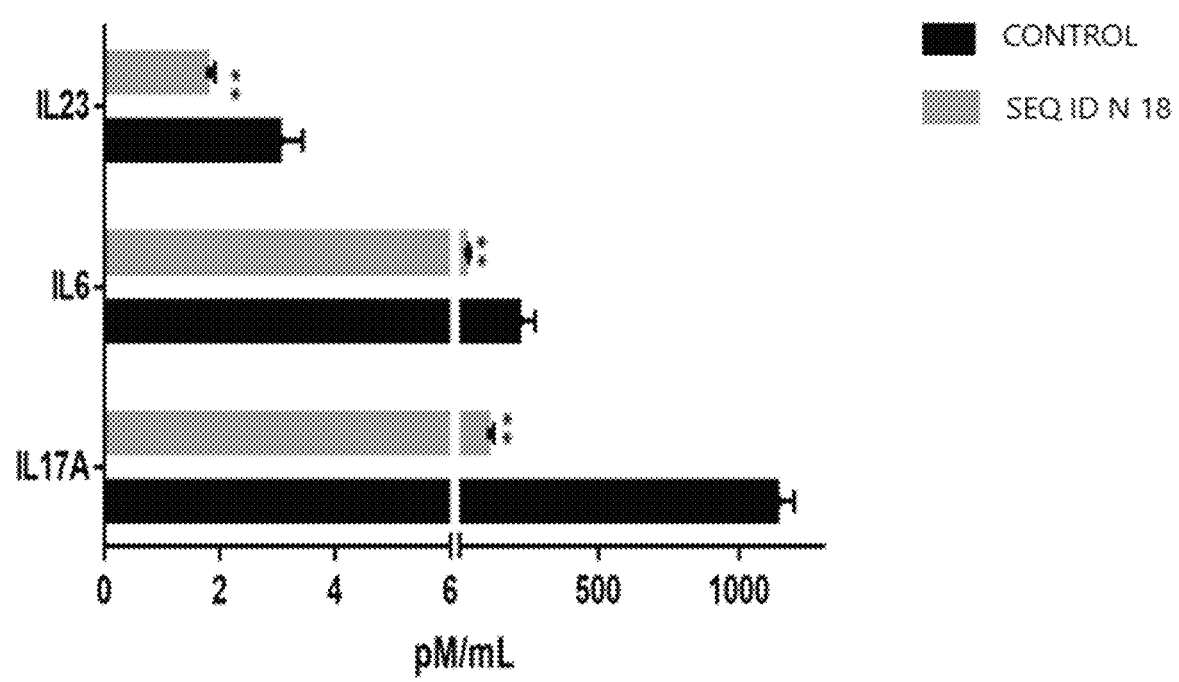
FIG. 2 shows the activity of the IL-17A binding peptide of SEQ ID NO:18 on secretion of IL6, IL-17A and IL23 by human differentiated and activated TH17 cells, measured as described in Example 6. The concentration of the different cytokines in the supernatant of TH17 cells with or without (control) peptide of SEQ ID NO:18 is reported.
Figure 3:
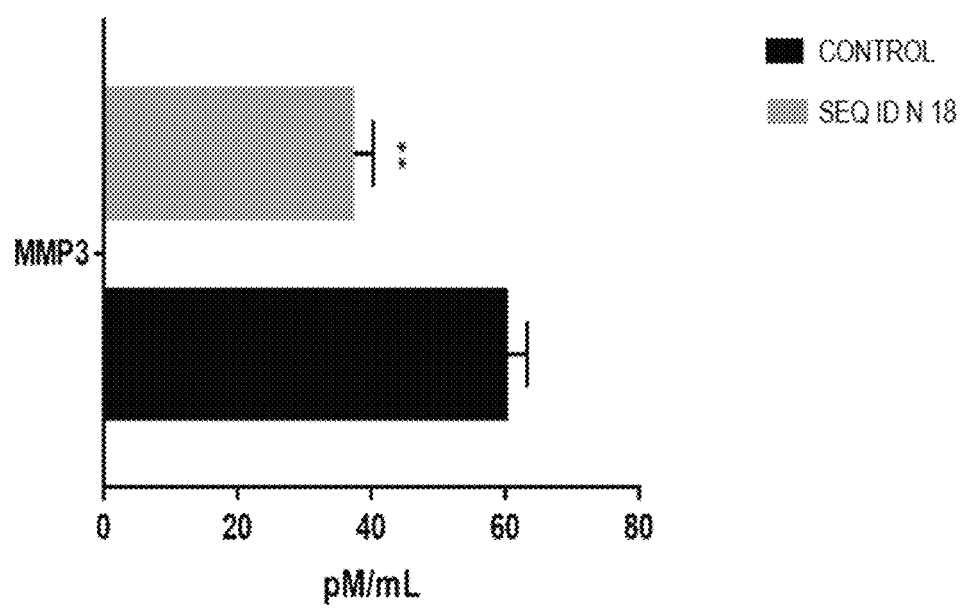
FIG. 3 shows the activity of the IL-17A binding peptide of SEQ ID NO:18 on secretion of Metalloproteinase 3 by human differentiated and activated TH17 cells, measured as described in Example 6. The concentration of Metalloproteinase 3 in the supernatant of TH17 cells with or without (CONTROL) peptide of SEQ ID NO:18 is reported.
Figure 4:
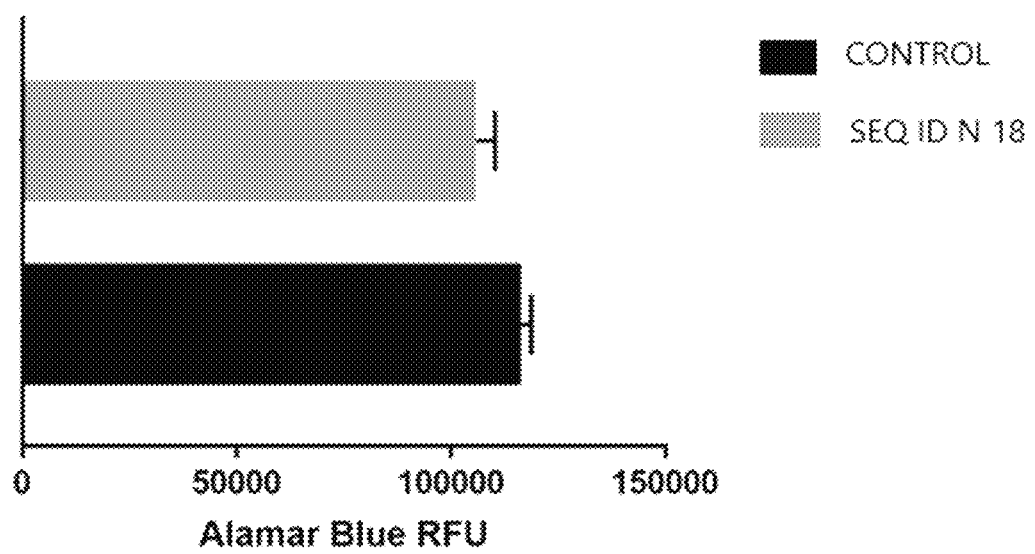
FIG. 4 shows viability of human TH17 cells after 24 h, in the presence and absence (control) of the peptide of SEQ ID NO: 18, as described in Example 6.
Figure 5:
FIG. 5 shows the binding site on IL-17A of the IL-17A peptides according to the invention.

FIGS. 2 and 3 show the effect of the peptide of SEQ ID NO: 18. As can be seen, this peptide is able to significantly reduce the secretion of IL-17 Å, IL-6 and IL-23 as well as the secretion of MMP3. As shown in FIG. 4 the inhibition of cytokines and metalloproteinases secretion is not due to cell viability issues since cell treatment with the peptide of SEQ. ID N. 18 for eleven days did not impair cell viability.

Example 7: Physical-Chemical Analysis of Peptides

The physical-chemical properties of the prior art peptide HAP and of some peptides according to the invention (see table 8) have been tested as described below.
i. Methods
a. Isoelectric Poitn IP Log D and Log P The main physicochemical properties (Isoelectric point (IP), log D (7.4) and log P) of the peptides of Table 8 below were determined by using the SiriusT3 apparatus (Sirius Analytical Instruments Ltd., East Sussex, UK) equipped with an Ag/AgCl double junction reference pH electrode, a Sirius D-PAS spectrometer and a turbidity sensing device. The pH electrode was calibrated titrimetrically in the pH range 1.8-12.2. An overhead stirrer was used and a temperature probe (Peltier controller) monitored the temperature during the course of the titration. The titration experiments were conducted in 0.15 M KCl Ionic Strength Adjusted solution (ISA water) under a nitrogen atmosphere at a temperature of 25±1° C. All tests were performed using standardized 0.5 M KOH and 0.5 M HCl as titration reagents, for the partition coefficient tests a saturated Octanol in ISA water (5% of ISA water) was used as partition solvent. The pKas were determined by potentiometric method by pH-metric titration. The powder (around 0.5 mg) was dissolved in 1.5 ml of ISA water and the titration was performed in triplicate in the pH range 2.0-12.0. Each Log P were performed in triplicate by dissolving the powder (around 1 mg) in 1 ml of ISA water followed by pH metric titration in three different percentages of octanol (in general 50%, 60%, 70%).
b. Water Solubility and Stability
General Procedure for the Preparation of the Stock Solutions
Each lyophilized peptide was weighed in an amber vial. A calculated volume of phosphate buffered solution at pH 7.8 was added in order to directly obtain 10 mM Stock Solutions. The recovered suspensions were stirred for 30 minutes by orbital shaker incubator at 37° C. Subsequent dilutions were performed to obtain the more diluted stock solutions for the less soluble compounds.

In order to evaluate the stability and the solubility, all the stock solutions were stored at 25° C.

The title was evaluated by UHPLC-MS analysis in comparison with the standard solutions, at 3 time points: T0, 3 days, 1 week.

The chromatographic profile was evaluated for the quantitative assay while the MS spectra were detected as support in the stability studies.

General Procedure for the Standard Solution Preparation

Each peptide was weighed and directly diluted at 100 μM with the phosphate buffer at pH 7.8. The solutions were stirred for 5 minutes by vortex and heated at 37° C. for 20 minutes. The obtained standard solution was stored at 25° C. in the dark under controlled temperature.

General Procedure for the Sample Preparation

A portion of the stock solutions was collected in an amber vial and diluted to 100 μM by phosphate buffer at pH 7.8 (dilution factor, 1:100).

Instrument Method

Reversed-phase UHPLC was performed operating at a flow rate of 0.3 ml/min with a Luna Omega Polar C18 column (pore size 1.6 μm, 2.1×100 mm). Solvent A was 0.5% Formic Acid in water and solvent B was 0.5% Formic Acid in acetonitrile. First, samples were loaded onto the column and washed isocratically at 10% B for 3 min. Then, a gradient of 10-95% B was run over 22 min, held at 95% for 2 min, and then decreased to 10% over 1 min and held, for the pressure stabilization, for 5 min. UV Absorption was monitored by DAD (220-400 nm). ESI-MS ion trap was used for the monitoring of TIC.

ii. Results

All peptides tested showed stability at 25° C. up to 1 week since no significant variations were found in the chromatographic profile and in the mass spectra.

The physchemical properties of the tested peptides are displayed in Table 8 below.

TABLE 8

| PEPTIDE | IP | Log D (7A) | logP | SOLUBILITY |
|---|---|---|---|---|
| SEQ ID NO: 1 | 5.14 | −3.58 | −5.98 | >10 mM |
| SEQ ID NO: 2 | 5.14 | −0.56 | 0.99 | >10 mM |
| SEQ ID NO: 3 | 3.90 | −1.37 | 1.33 | 10 μM |
| SEQ ID NO: 4 | 3.90 | −1.32 | 1.88 | 20 μM |
| SEQ ID NO: 5 | 5.19 | −1.26 | −0.51 | 1 mM |
| SEQ ID NO: 6 | 5.14 | −3.65 | −0.37 | >10 mM |
| SEQ ID NO: 7 | 5.19 | −1.41 | −0.86 | >10 mM |
| SEQ ID NO: 8 | 5.14 | −4.06 | −5.12 | >10 mM |
| SEQ ID NO: 9 | 8.28 | −1.08 | −0.53 | >10 mM |
| SEQ ID NO: 10 | 5.14 | −3.66 | 0.09 | >10 mM |
| SEQ ID NO: 11 | 4.25 | −2.92 | 1.05 | >10 mM |
| SEQ ID NO: 12 | 3.66 | −5.24 | 1.31 | 10 μM |
| SEQ ID NO: 13 | 6.06 | 1.15 | −0.49 | >10 mM |
| SEQ ID NO: 14 | 8.99 | −2.80 | −5.40 | >10 mM |
| SEQ ID NO: 15 | 3.51 | 1.88 | 1.66 | 50 μM |
| SEQ ID NO: 16 | 5.19 | 0.24 | 0.13 | >10 mM |
| SEQ ID NO: 17 | 8.05 | −3.68 | −0.44 | >10 mM |
| SEQ ID NO: 18 | 3.55 | −3.79 | 1.89 | 50 μM |
| SEQ ID NO: 41 | 3.54 | −1.94 | 1.24 | >10 mM |
| SEQ ID NO: 19 | 12.49 | −3.94 | −8 | 100 μM |
| SEQ ID NO: 20 | 11.29 | −3.69 | −6.79 | 100 μM |
| SEQ ID NO: 21 | 10.6 | −0.55 | −4.99 | >10 mM |
| SEQ ID NO: 22 | 4.26 | −3.18 | 0.4 | >10 mM |
| SEQ ID NO: 23 | 4.26 | −2.24 | 1.01 | 50 μM |
| SEQ ID NO: 24 | 5.14 | 2.15 | 2.45 | <50 μM |
| SEQ ID NO: 25 | 4.66 | −5.64 | 0.4 | 100 μM |
| SEQ ID NO: 26 | 8.13 | 0.148 | 0.69 | >10 mM |
| SEQ ID NO: 27 | 5.14 | 0.148 | 0.69 | >10 mM |
| SEQ ID NO: 28 | 12.25 | −6.44 | −6.36 | 100 μM |
| SEQ ID NO: 29 | 12.25 | −6.44 | −6.39 | >10 mM |
| SEQ ID NO: 30 | 12.95 | −3.89 | −7.44 | 100 μM |
| SEQ ID NO: 31 | 12.5 | −3.59 | −4.9 | >10 mM |
| SEQ ID NO: 32 | na | −3.59 | −10 | <50 μM |
| SEQ ID NO: 33 | 4.46 | −1.06 | 1.99 | 100 μM |
| SEQ ID NO: 34 | 5.14 | −3.38 | −5.43 | <50 μM |
| SEQ ID NO: 35 | 5.14 | −3.52 | −5.43 | >10 mM |
| SEQ ID NO: 36 | 8.13 | −1.24 | −1.09 | 100 μM |
| SEQ ID NO: 37 | 5.14 | −3.9 | −6.89 | >10 mM |
| SEQ ID NO: 38 | 5.14 | −3.46 | −5.87 | >10 mM |
| SEQ ID NO: 39 | 4.2 | −2.86 | −5.36 | >10 mM |
| SEQ ID NO: 40 | 4.21 | −3.5 | −4.93 | >10 mM |
| SEQ ID NO: 111 | 8.99 | −0.93 | −0.38 | <50 μM |
| SEQ ID NO: 112 | 8.99 | −7.295 | −4.76 | <50 μM |
| SEQ ID NO: 113 | 8.99 | −3.472 | −0.13 | <50 μM |
| SEQ ID NO: 114 | 8.99 | −3.591 | −0.21 | <50 μM |
| SEQ ID NO: 115 | 8.99 | −3.914 | −5.94 | <50 μM |
| SEQ ID NO: 121 | 8.99 | −1.474 | −0.51 | <50 μM |

As can be seen from the above, most of the peptides according to the invention have optimal physchem properties, showing a good balance between solubility and lipophilicity. The mean of Log D of the peptides was −2.64±2.06, while for most of the peptides, the solubility observed in water was very good (>10 mM). The properties observed make them particularly suitable to be used for ophthalmic and dermatological applications, since both hydrophobic and hydrophilic components are present in the derma and eye surface. They also explain the good permeability observed by peptides (see Example 8).

Example 8: Permeability Test

The peptides tested were the peptides of SEQ ID NO: 1, SEQ ID NO: 2, SEQ ID NO: 7, SEQ ID NO: 11, SEQ ID NO: 14, SEQ ID NO: 38, SEQ ID NO: 111, SEQ ID NO: 113. SEQ ID NO: 115 and SEQ ID NO: 121. They were dissolved in Cell Culture Grade Water (Corning, Manassas, VA, USA) in order to have 10 mM stock solution.

i. Methods

In Vitro Model

The I-HCEC, Immortalized Human Corneal Epithelial cell line was derived from Primary Human Corneal Epithelial Cells (>99% purity). These cells are suitable for studies of human cornea in health and disease. The cells were cultured following the protocol and using the media suggested by Innoprot, Bizkaia, Spain (IM-Corneal Epithelial Cell Medium ref. P60131).

Immunofluorescence

Qualitative and quantitative techniques were developed to first confirm and quantify the barrier integrity before proceeding with drug testing. First, we performed immunofluorescence for a protein characteristic of tight junctions (Z0-1) (Sugrue S P et al., (1997) Exp Eye Res. January; 64 (1): 11-20). The cells were seeded in coverslip coated with Collagen I 50 μg/ml (stock solution 3 mg/ml from Gibco, NY, USA) at a density of 1*104 cells/cm2 and cultured for 14 DIV and post-confluency the media were refreshed every day. Cells were fixed in methanol at −20° C. for 10 min, rinsed with phosphate buffer solution (PBS), incubated for 10 min at room temperature (RT) in PBS containing 4% bovine serum albumin (BSA; Sigma-Aldrich), and successively incubated with the primary and secondary antibodies for 60 min each at RT. Primary antibody was goat anti-human ZO-1 (1:100, Thermo Fisher) overnight at 4° C. followed by anti-goat Alexafluor 488 (1:10000). Cells were finally counterstained with DAPI (0.5 mg/ml) (Sigma-Aldrich) for 5 min at room temperature, mounted with Vectashield Mounting Medium (Vector Laboratories Inc, Burlingame, CA) and observed at confocal laser scanning Microscope (Leica TCS SP5, Wetzlar, Germany).

MTS Assay

Cell viability was determined at 24 h using Cell Titer One Solution Cell Proliferation Assay (Promega Corporation Madison, WI, USA) a colorimetric method based on 3-(4,5-dimethylthiazol-2-yl)-5-(3-carboxymethoxyphenil)-2-(4-sulfophenyl)-2H-tetrazolium (MTS). The quantity of formazan formed, as a function of viability, was measured at 492 nm using an ELISA plate reader, Infinite F200 (Tecan, Mannedorf, Swiss). The assay was performed at 50 and 100 µM (N=9). The results were expressed as absorbance at 492 nm.

TEER Assay

The barrier integrity of corneal epithelial cultures was verified using measurement of TEER (TransEpithelial/TransEndothelial Electrical Resistance)) and permeability of paracellular permeants (e.g., mannitol, 6-carboxyfluorescein) (Ronkko S et al., (2016) Drug Deliv Transl Res 6: 660-675). TEER is a widely accepted quantitative technique to measure integrity of tight junction dynamics in cell culture models of endothelial and epithelial monolayers. TEER values are indicators of the integrity of the cellular barriers before they are evaluated for transport of drugs or chemicals. TEER measurements can be performed in real-time without cell damage and generally are based on measuring osmic resistance or measuring impedance across a wide spectrum of frequencies (Snirivasan et al., 2015 J Lab Autom. 20(2): 107-126). To perform this assay Millicell ERS-2, Electrical Resistance System by EMD Millipore (Burlington, MA, USA), was used following manufacturer's instructions. The assay was performed at 50 and 100 µM (N=9). Results were expressed as Resistance (Q/cm2).

Permeability Test

The objective of this study was to evaluate the apparent permeability coefficient (Papp) value of the peptides across stratified human corneal epithelial cells. All peptides were tested at 50 µM in duplicate.

In particular, human corneal epithelial cells (hCEPIC) were stratified on Transwell cell culture inserts (Corning, N.Y., USA). The permeation experiments were performed taking samples from receiver chambers at 5, 30, 60 minutes time points and from donor chambers at the same time points. Each aliquot collected was analyzed by HPLC instrument (Knauer) equipped with C18 Vertex Plus Column (Knauer) thermostatically controlled at 40° C. The rate (apparent permeability coefficient, Papp) of the study compounds was calculated and compared to the Papp values of the low and high permeability markers, 6-carboxyfluorescein and Rhodamine B, respectively.

The apparent permeability coefficient (Papp) was calculated according to Equation:

$$Papp = (1/A \cdot C0)(dM/dt)$$

where dM/dt is the flux (nanomoles per second) across the cell layers;
A (square centimeters) is the exposed surface area of the insert membrane;
C0 is the initial drug concentration (micromolar) in the donor compartment at t=0 (Xiang et al., Drug Metab Dispos. 2009 May; 37(5):992-8.

Statistics

All groups (studied compound and rhodamine) were compared to low permeability control. All the other experiments were expressed as the meant S.E. and the significance were calculated by Student's t test versus control cells. Difference were considered to be statistically significant ($p<0.05$) as determined by Student's t test.

ii. Results

MTS and TEER Assays

In our experimental conditions, the peptides considered did not significantly affect cell viability or TEER at 50 µM and 100 µM test concentration.

Permeability Test

The results obtained for each peptide are shown in Table 9 below.

TABLE 9

| Peptide N/Name | Sequence | Permeability ($10^{-6}$ cm/sec) |
|---|---|---|
| SEQ ID NO: 1 | IHVTIPADLWDWINK | 19.333 |
| SEQ ID NO: 7 | IHVTIPADLWEWINK | 24.252 |
| SEQ ID NO: 11 | IHVTIPADLWDWIEK | 28.020 |
| SEQ ID NO: 2 | VHVTIPADLWDWINK | 28.862 |
| SEQ ID NO: 14 | IHVTIPADLWDWVRR | 28.873 |
| SEQ ID NO: 38 | VPGAGVPGAGIHVTIPADLWDWINK | 30.417 |
| SEQ ID NO: 121 | VHVTIPADLWEWFRR | 47.083 |
| SEQ ID NO: 115 | VHVTIPQDLWEWVRR | 68.800 |
| SEQ ID NO: 113 | VHVQIPADLWEWVRR | 76.797 |
| SEQ ID NO: 111 | VHVTIPAELWEWVRR | 83.698 |
| Rhodamine B | | 51.26 |
| 6-carboxyfluorescein | | 0.61 |

To verify that the HCE cell culture was useful in screening the peptides, the permeability of a lipophilic transcellular marker rhodamine B was determined. As expected, rhodamine B exhibited high permeability of the HCE cell culture ($51.26\pm5.44$ $10^{-6}$ cm/sec). Then, the permeability of 6-carboxyfluorescein was assayed and in agree with the literature ($0.61\pm0.33$ $10^{-6}$ cm/sec). This marker has a very low lipophilicity, and it permeates biological membranes only through the intercellular space.

The tested peptides showed a very good permeability towards the Immortalized Human Corneal Epithelial compared to high permeability standard, Rhodamine B. Obviously, the HCE permeability model does not include stroma or endothelium, but these layers are not critical barriers to corneal drug absorption. We found peptides with a good permeability (SEQ ID NO: 2) and peptides with a higher permeability compared to Rhodamine B (SEQ ID NO: 115. SEQ ID NO: 113 and SEQ ID NO: 111).

Example 9: Peptide-IL-17 Å Affinity Test

The peptide of the prior art HAP (SEQ ID NO:1) and peptide of SEQ ID NO:2 were tested for affinity for mIL-17 Å, as described below.

a. Immobilization of mIL-17 Å

For the immobilization of mouse IL-17 Å protein, amine coupling chemistry was used. On the sensorchip surface the dextran matrix was first activated with a mixture of 1-ethyl-3-carbodiimide (EDC) and N-hydroxysuccinimide (NHS) in order to obtain reactive succinimido esters. 10 ug/ml of IL17 was diluted in 10 mM acetate buffer at pH=5.0 and then the ligand passed over the surface to allow the esters to react spontaneously with uncharged amino groups, in this way the ligand is covalently linked to dextran. Covalent immobilization of mIL17 results in stable attachment of 3000 RU of ligand to the surface.

b. Characterization of the Peptides/IL17 Interaction

Figure 6:
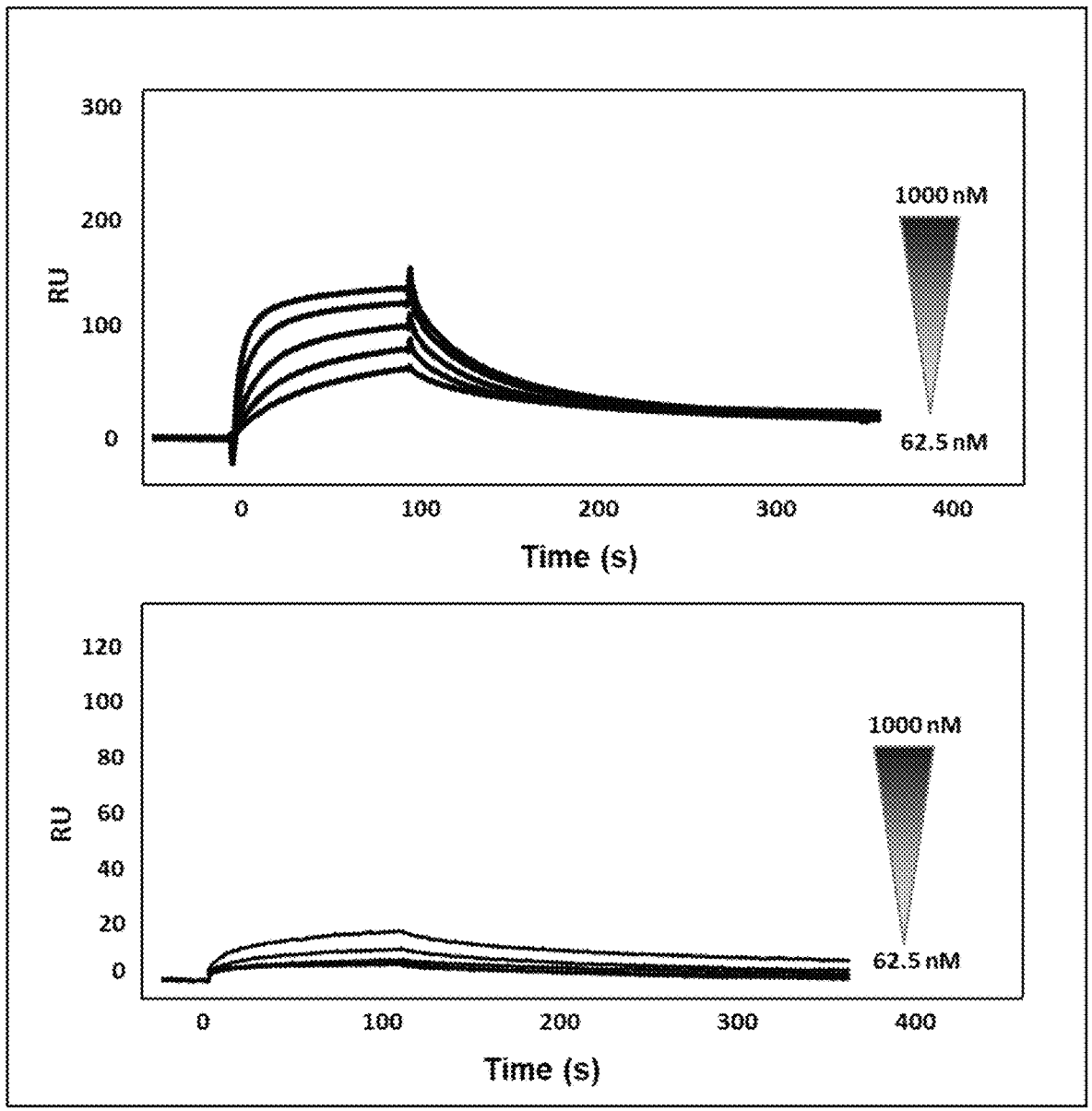
FIG. 6 shows the sensograms obtained in the experiment of Example 9 with the peptide of SEQ ID NO: 2 (upper panel) or SEQ ID NO: 1 (lower panel).
Figure 7:
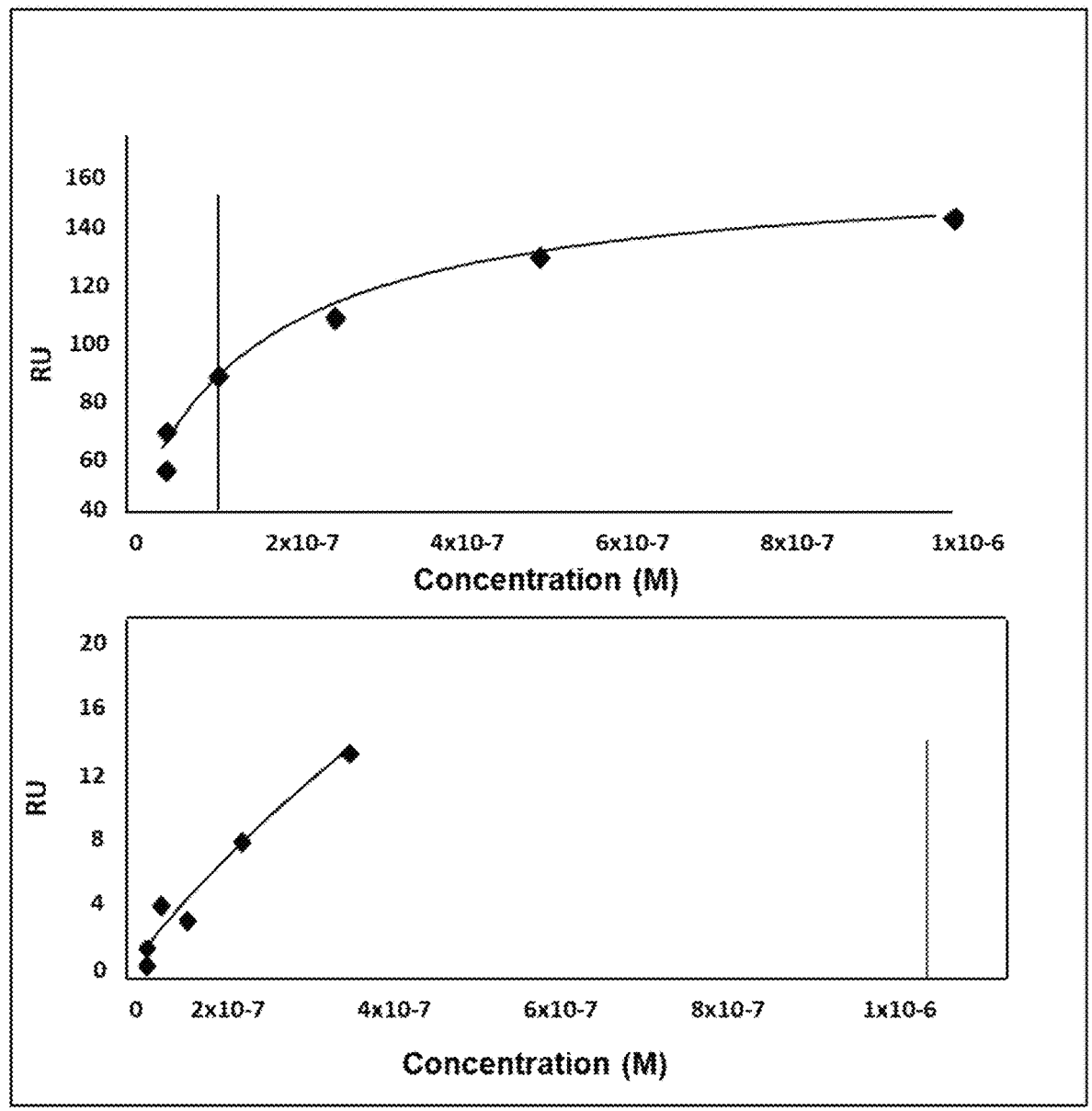
FIG. 7 shows the value of the affinity constant at different concentrations of the peptide of SEQ ID NO: 2 (upper panel) or SEQ ID NO: 1 (lower panel), obtained in the experiment of Example 9.

The peptides of SEQ ID NO: 1 (HAP) and SEQ ID NO: 2 were analyzed for their ability to bind the immobilized mIL-17 Å. The molecules were diluted at different concentrations (from 62.5 to 1000 nM) in HBS-EP buffer and injected on the sensorchip for 4 minutes and allowed to dissociate for 5 minutes. After each run, the sensorchip was regenerated by 2 M NaCl injection. Based on the sensorgrams (FIG. 1, panel A) and using the BIAevaluation software, the Scatchard analysis of the RU values at equilibrium allowed to determine an affinity constant as a function of the analyte concentration in solution (FIG. 6, panel B). The results obtained are shown in Table 10 below

TABLE 10

| Compound | Kdea (nM) |
|---|---|
| SEQ ID NO: 1 | 3700 |
| SEQ ID NO: 2 | 130 |

As shown in Table 8, the peptide of SEQ ID NO: 2 binds to IL-17 Å with a value of affinity equal to 130 nM, while peptide of SEQ ID NO: 1 binds to IL17-A with a very low affinity value (3700 nM).

In view of the results obtained in Example 8 and 9, the modification of the Isoleucine in position 1 in the HAP peptide of the prior art with a Valine, as in the peptide of SEQ ID NO: 2, leads to a striking difference regarding the physchemical properties, permeability and affinity for the ligand.

We summarize herein below the properties of the two peptides:

TABLE 11

| Property | SEQ ID NO: 1 (HAP) | SEQ ID NO: 2 |
|---|---|---|
| Sequence | IHVTIPADLWDWINK | VHVTIPADLWDWINK |
| logP | −5.98 | 0.99 |
| logD (7.4) | −3.68 | −0.56 |
| Permeabilitu (Papp ± SE) | 19.3 | 28.86 |
| SPR Kdeq (nM) | 3700 | 130 |

Table 11 shows the comparison data between peptide SEQ ID NO: 1 and SEQ ID NO: 2. We found great differences in term of log P and log D (6-log and 3-log difference, respectively): this explained the higher permeable observed with SEQ ID NO: 2 compared to SEQ ID NO: 1 (28.8 vs 19.3). The Kd (nM) measured in the Surface plasmon resonance (SPR) assay performed on mouse IL-17 Å, showed that SEQ ID NO: 2 was 28-fold more affine than SEQ ID NO: 1.

Furthermore, molecular dynamics simulations studies were also carried out, which indicate that Valine (SEQ ID NO: 2) instead of the Isoleucine (HAP) greatly stabilizes the folded structure: SEQ ID NO: 2 was predicted to be 80% more stable.

Example 10: In Vitro Evaluation of Expression of Inflammatory Cytokines

The peptide HAP (SEQ ID NO:1) and the peptide of SEQ ID NO:2 were tested in vitro for evaluation of their direct influence on expression of inflammatory cytokines in the cornea. The tests were conducted on Immortalized Human Corneal Epithelial cell line (1-HCEC) (Innoprot, Bizkaia, Spain, Ref. P10871). This is derived from Primary Human Corneal Epithelial Cells (>99% purity) and is suitable for studies of human cornea in health and disease. The cells were cultured following the protocol and using the media suggested by Innoprot (IM-Corneal Epithelial Cell Medium ref. P60131). The cell medium was supplemented with 5% Fetal Bovine Serum (FBS).

Cells were seeded at 320000 cells/well 6 plate and 15000 cells/well 96 plate. When the cells reached 80% of confluence were treated with SEQ ID NO: 1 and SEQ ID NO: 2 compounds in dose-curve (0.01-500 µM) for 24 hours.

Total RNA was isolated from 6 wells plate using QuickStart RNeasy Mini Kit (Qiagen, cat. No 74104) according to the manufacturers instructions. Retro-transcription was performed using SuperScript Vilo (ref. 11755050, Life technologies) and real-time PCR using TaqMan protocol (ref. 4444557, Applied Biosystem) adapted for CFX96 Real-Time System. The experiments were performed three times, each time in duplicate. The used probes from Thermo Fisher Scientific are: human CXCL8 (Hs00174103_m1), human IL6 (Hs00174131_m1), human TNFα (Hs99999043_m1). As housekeeping gene was used GAPDH (probe Hs02758991_g1). IL-8, IL-6 and TNF-α expression in I-HCEC was evaluated after treatment for 24 hours with different concentration of the peptide of SEQ ID NO: 1 or SEQ ID NO: 2 (0.01, 0.1, 1, 10, 100, 500 µM). Untreated I-HCEC were used as negative control (Vehicle).

Figure 8A:
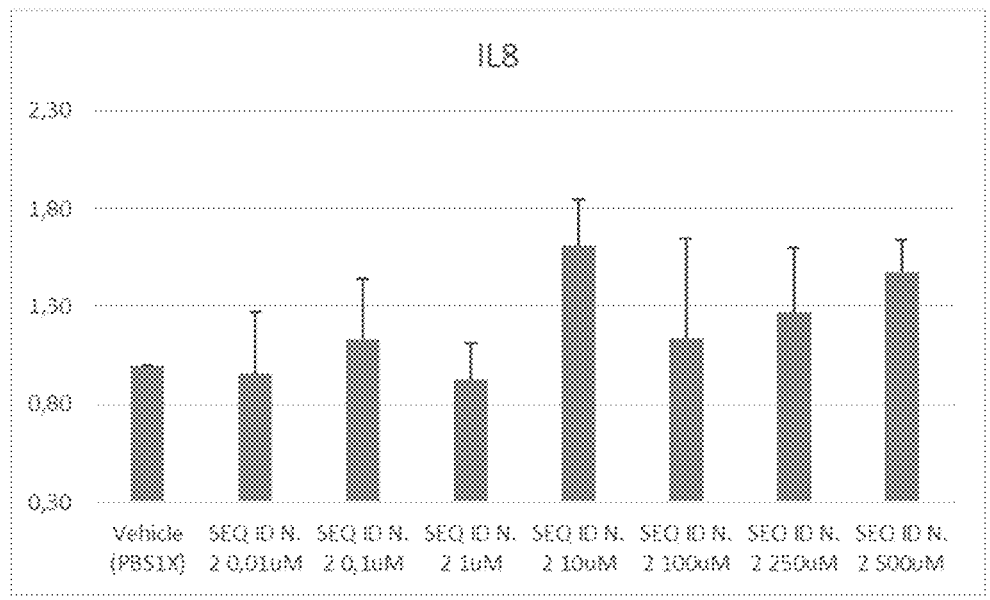
FIGS. 8A-8B show the level of expression of IL-8 measured by real-time PCR as described in Example 10 in HCEC cells not treated (vehicle) or treated with the peptide of SEQ ID NO: 2 (FIG. 8A) or with the peptide HAP (SEQ ID NO: 1) (FIG. 8B). The error bars represent the standard deviation. T-test was performed as statistical analysis. P-value *<0.05, <0.005, *<0,0005.
Figure 8B:
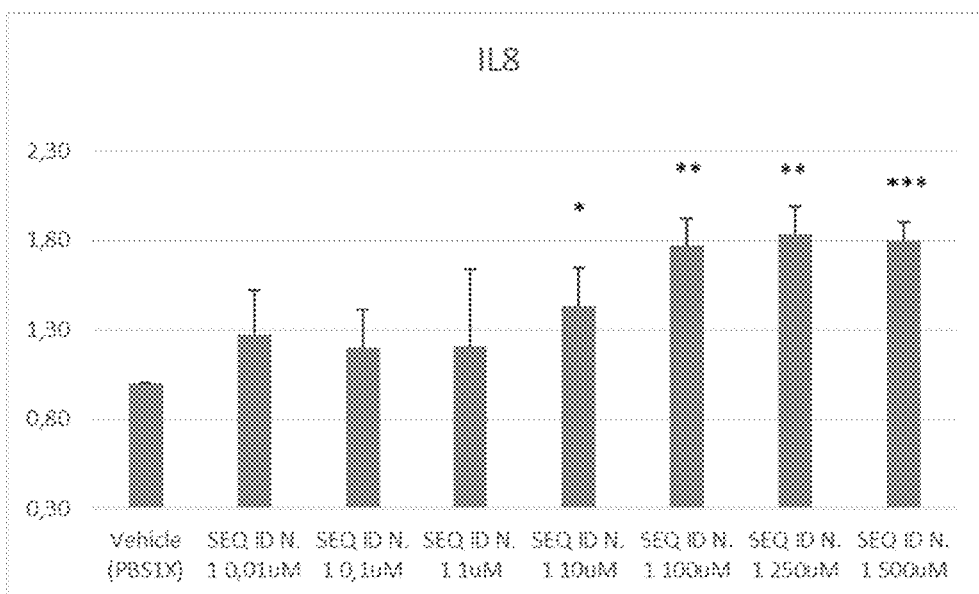
Figure 9A:
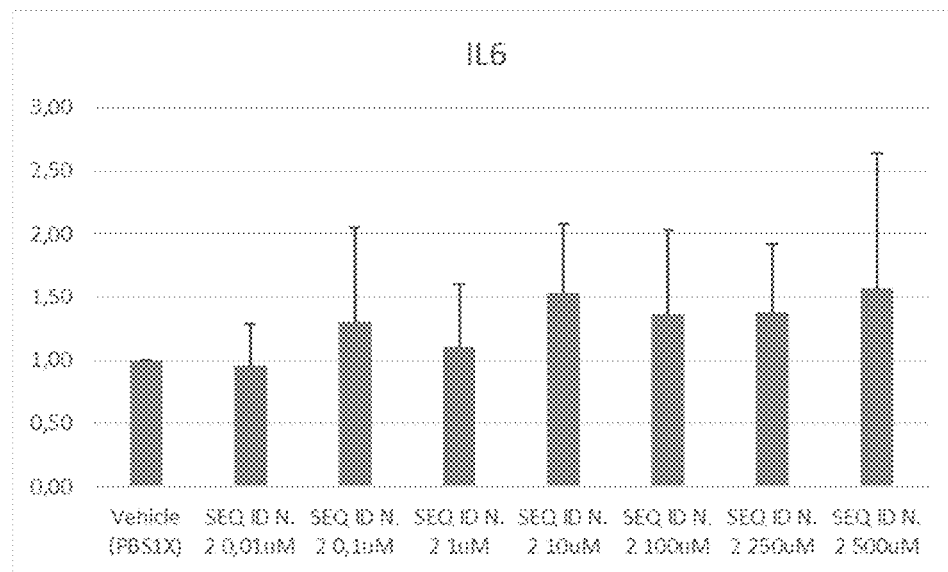
FIGS. 9A-9B show the amount of IL-6 measured by real-time PCR as described in Example 10 in HCEC cells not treated (vehicle) or treated with the peptide of SEQ ID NO: 2 (FIG. 9A) or with the peptide HAP (SEQ ID NO: 1) (FIG. 9B). The error bars represent the standard deviation. T-test was performed as statistical analysis. P-value *<0.05, *<0.005, ***<0,0005.
Figure 9B:
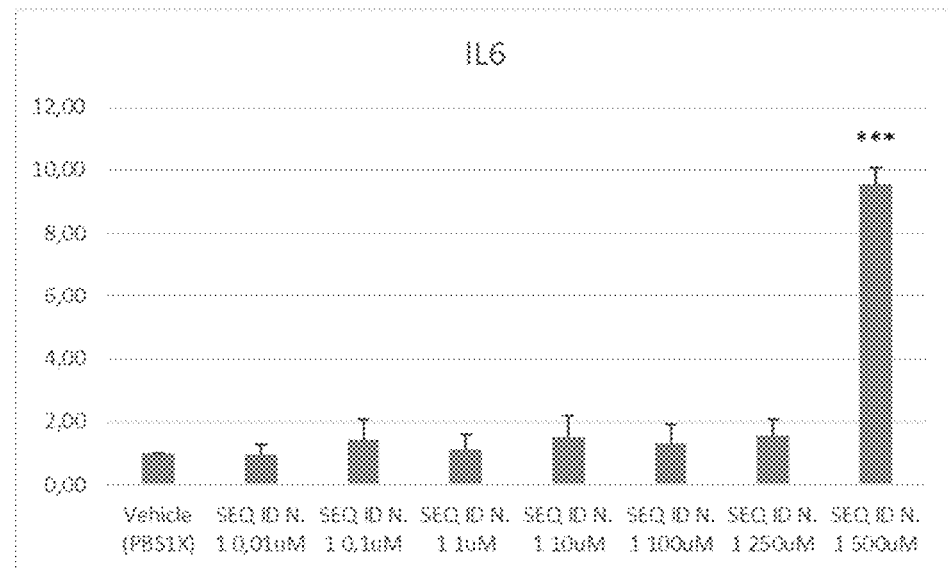
Figure 10A:
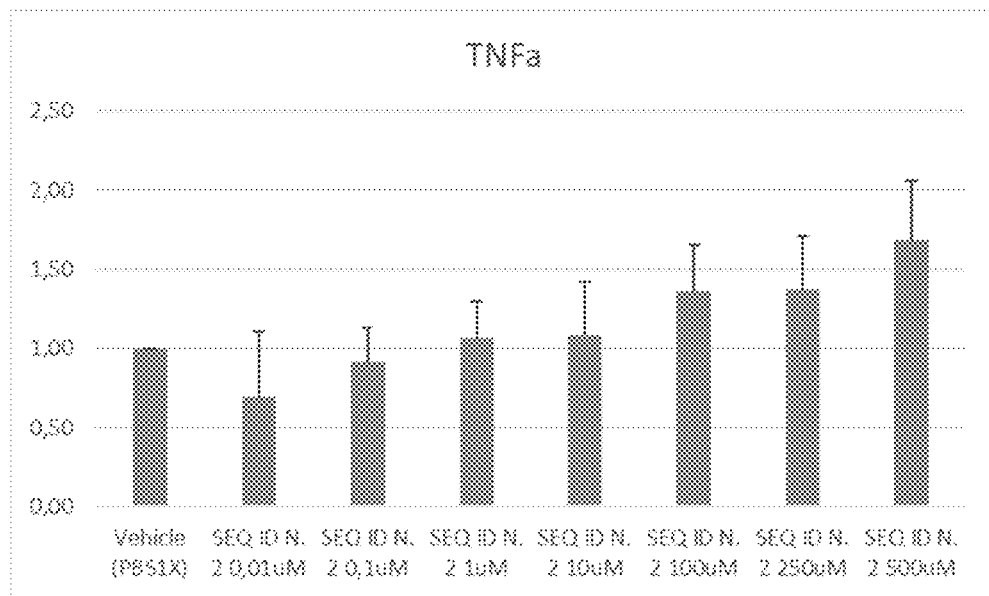
FIGS. 10A-10B show the amount of TNF-α measured by real-time PCR as described in Example 10, in HCEC cells not treated (vehicle) or treated with the peptide of SEQ ID NO: 2 (FIG. 10A) or with the peptide HAP (SEQ ID NO: 1) (FIG. 10B). The error bars represent the standard deviation. T-test was performed as statistical analysis. P-value *<0.05, <0.005, *<0,0005.
Figure 10B:
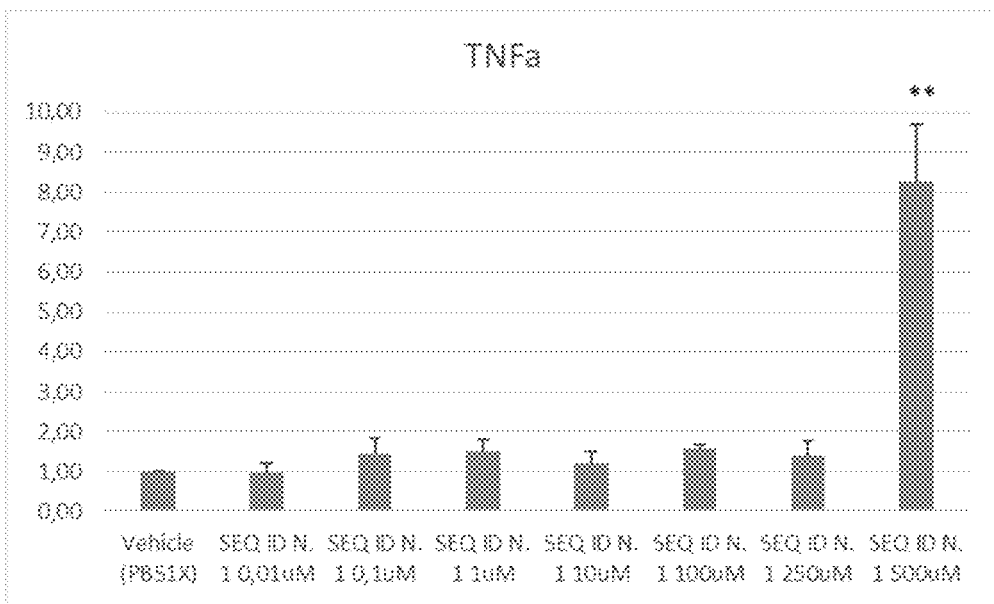

The results show that the compound SEQ ID NO: 2 does not change the expression of any of the measured inflammatory cytokines (FIGS. 8A, 9A and 10A), while the treatments with 500 µM of the compound SEQ ID NO: 1 significantly induce the expression of the two inflammatory cytokines IL-6 and TNFα (FIGS. 9B and 10B).

The data obtained demonstrate that peptide of SEQ ID NO: 1 has a direct pro-inflammatory activity and induces significantly the expression of IL-6 and TNF-α inflammatory cytokines by HCEC, with an increase of 10 and 8 fold, respectively. On the contrary, the peptide of SEQ ID NO: 2 does not show any effect on the expression of cytokines.

In view of the above, it can be concluded that the peptide of SEQ ID NO: 2 surprisingly shows significantly better tolerability and lack of toxicity compared to the peptide HAP of SEQ ID NO: 1.

The invention claimed is:

1. A peptide that specifically inhibits IL-17A binding to ILRA, comprising the amino acid sequence of Formula (I), wherein Formula (I) comprises an amino acid sequence selected from SEQ ID NO: 165, SEQ ID NO: 166, SEQ ID NO: 169, SEQ ID NO: 181, SEQ ID NO: 192, SEQ ID NO: 194, SEQ ID NO: 195, SEQ ID NO: 197, SEQ ID NO: 214, SEQ ID NO: 219, SEQ ID NO: 221, SEQ ID NO: 223, SEQ ID NO: 262, or SEQ ID NO: 263.

2. The peptide of claim 1, wherein the peptide consists of a 15 amino acid sequence.

3. A peptide that specifically inhibits IL-17A binding to ILRA, comprising the amino acid sequence of IHVTIPADLWDWINK (SEQ ID NO: 1), wherein the peptide further comprises a sequence at the C- and/or N-terminal of the peptide, wherein the peptide comprises, in order, a sequence selected from:

(a)
VPGDG (SEQ ID NO: 53)
--IHVTIPADLWDWINK, (SEQ ID NO: 1)

(b)
IHVTIPADLWDWINK (SEQ ID NO: 1)
--VPGDG, (SEQ ID NO: 53)

(c)
IHVTIPADLWDWINK (SEQ ID NO: 1)
--VPGWG, (SEQ ID NO: 47)

(d)
IHVTIPADLWDWINK (SEQ ID NO: 1)
--VPGAG, (SEQ ID NO: 50)

(e)
IHVTIPADLWDWINK (SEQ ID NO: 1)
--ARKKAAKA, (SEQ ID NO: 44)

(f)
VPGWG (SEQ ID NO: 47)
--IHVTIPADLWDWINK, (SEQ ID NO: 1)

(g)
VPGAG (SEQ ID NO: 50)
--IHVTIPADLWDWINK, (SEQ ID NO: 1)

(h)
IHVTIPADLWDWINK (SEQ ID NO: 1)
--VPGKG, (SEQ ID NO: 49)

(i)

VPGKG (SEQ ID NO: 49)

--IHVTIPADLWDWINK, (SEQ ID NO: 1)

(j)

ARKKAAKA (SEQ ID NO: 44)

--IHVTIPADLWDWINK, (SEQ ID NO: 1)

(k)

IHVTIPADLWDWINK (SEQ ID NO: 1)

--RRRRRRRR, (SEQ ID NO: 52)

(l)

IHVTIPADLWDWINK (SEQ ID NO: 1)

--TWWETWW, (SEQ ID NO: 46)

(m)

RRRRRRRR (SEQ ID NO: 52)

--IHVTIPADLWDWINK, (SEQ ID NO: 1)

(n)

IHVTIPADLWDWINK (SEQ ID NO: 1)

--RQIKIWFQNRRMKWKK, (SEQ ID NO: 51)

or (o) IHVTIPADLWDWINK (SEQ ID NO: 1)--RRRRRR (SEQ ID NO: 265).

4. The peptide of claim 1, wherein a protective cap group is bound at the C- and/or N-terminal, wherein the protective cap group is selected from the group consisting of amides, aldehydes, esters, p-Nitroanilide, 7-Amino-4-methylcoumarin and the protective group cap bound to a N-terminal being selected from acetyl, formyl, pyroglutamyl, fatty acids, urea, carbamate sulfonamide, and alkylamine.

5. A dimer formed by two peptides, wherein each peptide is a peptide of claim 1.

6. The dimer of claim 5, wherein the peptides are linked by a polyethylene spacer.

7. A bioconjugate comprising the peptide of claim 1 and a biomolecule, wherein the biomolecule is bound to the N- and/or C-terminal of the peptide.

8. The bioconjugate of claim 7, wherein the biomolecule is selected from the group consisting of capric acid, capronic acid, ascorbic acid, NAG-NAM, NAG, NAM, hyaluronic acid, alginic acid, chitin, (GalNAc)2, Gal-alpha1,3-GalNAc and trigalacturonic acid.

9. A pharmaceutical composition comprising the peptide of claim 1 and at least one pharmaceutically acceptable excipient.

10. A method of producing the peptide of claim 1, comprising:
(a) synthesizing the peptide; and
(b) purifying the peptide.

* * * * *

SEQUENCE LISTING

<160> NUMBER OF SEQ ID NOS: 274

<210> SEQ ID NO 1
<211> LENGTH: 15
<212> TYPE: PRT
<213> ORGANISM: Homo sapiens

<400> SEQUENCE: 1

Ile His Val Thr Ile Pro Ala Asp Leu Trp Asp Trp Ile Asn Lys
1               5                   10                  15

<210> SEQ ID NO 2
<211> LENGTH: 15
<212> TYPE: PRT
<213> ORGANISM: Homo sapiens

<400> SEQUENCE: 2

Val His Val Thr Ile Pro Ala Asp Leu Trp Asp Trp Ile Asn Lys
1               5                   10                  15

<210> SEQ ID NO 3
<211> LENGTH: 15
<212> TYPE: PRT
<213> ORGANISM: Homo sapiens

<400> SEQUENCE: 3

Ile Met Val Thr Ile Pro Ala Asp Leu Trp Asp Trp Ile Asn Lys
1               5                   10                  15

<210> SEQ ID NO 4
<211> LENGTH: 15
<212> TYPE: PRT
<213> ORGANISM: Homo sapiens

<400> SEQUENCE: 4

Val Met Val Thr Ile Pro Ala Asp Leu Trp Asp Trp Ile Asn Lys
1               5                   10                  15

<210> SEQ ID NO 5
<211> LENGTH: 15
<212> TYPE: PRT
<213> ORGANISM: Homo sapiens

<400> SEQUENCE: 5

Ile His Val Thr Ile Pro Ala Glu Leu Trp Asp Trp Ile Asn Lys
1               5                   10                  15

<210> SEQ ID NO 6
<211> LENGTH: 15
<212> TYPE: PRT
<213> ORGANISM: Homo sapiens

<400> SEQUENCE: 6

Ile His Val Thr Ile Pro Ala Asp Leu Tyr Asp Trp Ile Asn Lys
1               5                   10                  15

<210> SEQ ID NO 7
<211> LENGTH: 15
<212> TYPE: PRT
<213> ORGANISM: Homo sapiens

<400> SEQUENCE: 7

Ile His Val Thr Ile Pro Ala Asp Leu Tyr Glu Trp Ile Asn Lys
1               5                   10                  15

<210> SEQ ID NO 8
<211> LENGTH: 15
<212> TYPE: PRT
<213> ORGANISM: Homo sapiens

<400> SEQUENCE: 8

Ile His Val Thr Ile Pro Ala Asp Leu Trp Asp Trp Val Asn Lys
1               5                   10                  15

<210> SEQ ID NO 9
<211> LENGTH: 15
<212> TYPE: PRT
<213> ORGANISM: Homo sapiens

<400> SEQUENCE: 9

Ile His Val Thr Ile Pro Ala Asp Leu Trp Asp Trp Ile Arg Lys
1               5                   10                  15

<210> SEQ ID NO 10
<211> LENGTH: 15
<212> TYPE: PRT
<213> ORGANISM: Homo sapiens

<400> SEQUENCE: 10

Ile His Val Thr Ile Pro Ala Asp Leu Trp Asp Trp Ile Asn Arg
1               5                   10                  15

<210> SEQ ID NO 11
<211> LENGTH: 15
<212> TYPE: PRT
<213> ORGANISM: Homo sapiens

<400> SEQUENCE: 11

Ile His Val Thr Ile Pro Ala Asp Leu Trp Asp Trp Ile Glu Lys
1               5                   10                  15

<210> SEQ ID NO 12
<211> LENGTH: 15
<212> TYPE: PRT
<213> ORGANISM: Homo sapiens

<400> SEQUENCE: 12

Ile His Val Thr Ile Pro Ala Asp Leu Trp Asp Trp Ile Asn Glu
1               5                   10                  15

<210> SEQ ID NO 13
<211> LENGTH: 15
<212> TYPE: PRT
<213> ORGANISM: Homo sapiens

<400> SEQUENCE: 13

Ile His Val Thr Ile Pro Ala Asp Leu Tyr Glu Trp Ile Asn Lys
1               5                   10                  15

<210> SEQ ID NO 14
<211> LENGTH: 15
<212> TYPE: PRT
<213> ORGANISM: Homo sapiens

<400> SEQUENCE: 14

Ile His Val Thr Ile Pro Ala Asp Leu Trp Asp Trp Val Arg Arg
1               5                   10                  15

<210> SEQ ID NO 15

```
<211> LENGTH: 15
<212> TYPE: PRT
<213> ORGANISM: Homo sapiens

<400> SEQUENCE: 15

Ile His Val Thr Ile Pro Ala Asp Leu Trp Asp Trp Val Glu Glu
1               5                   10                  15

<210> SEQ ID NO 16
<211> LENGTH: 15
<212> TYPE: PRT
<213> ORGANISM: Homo sapiens

<400> SEQUENCE: 16

Val Met Val Thr Ile Pro Ala Asp Leu Tyr Glu Trp Ile Asn Lys
1               5                   10                  15

<210> SEQ ID NO 17
<211> LENGTH: 15
<212> TYPE: PRT
<213> ORGANISM: Homo sapiens

<400> SEQUENCE: 17

Val Met Val Thr Ile Pro Ala Asp Leu Tyr Glu Trp Ile Arg Arg
1               5                   10                  15

<210> SEQ ID NO 18
<211> LENGTH: 15
<212> TYPE: PRT
<213> ORGANISM: Homo sapiens

<400> SEQUENCE: 18

Val Met Val Thr Ile Pro Ala Asp Leu Tyr Glu Trp Ile Glu Glu
1               5                   10                  15

<210> SEQ ID NO 19
<211> LENGTH: 21
<212> TYPE: PRT
<213> ORGANISM: Homo sapiens

<400> SEQUENCE: 19

Val Met Val Thr Ile Pro Ala Asp Leu Tyr Glu Trp Ile Glu Glu Arg
1               5                   10                  15

Arg Arg Arg Arg Arg
                20

<210> SEQ ID NO 20
<211> LENGTH: 18
<212> TYPE: PRT
<213> ORGANISM: Homo sapiens

<400> SEQUENCE: 20

Val Met Val Thr Ile Pro Ala Asp Leu Tyr Glu Trp Ile Glu Glu Arg
1               5                   10                  15

Arg Arg

<210> SEQ ID NO 21
<211> LENGTH: 23
<212> TYPE: PRT
<213> ORGANISM: Homo sapiens

<400> SEQUENCE: 21

Val Met Val Thr Ile Pro Ala Asp Leu Tyr Glu Trp Ile Glu Glu Ala
1               5                   10                  15
```

Arg Lys Lys Ala Ala Lys Ala
            20

<210> SEQ ID NO 22
<211> LENGTH: 25
<212> TYPE: PRT
<213> ORGANISM: Homo sapiens

<400> SEQUENCE: 22

Val Met Val Thr Ile Pro Ala Asp Leu Tyr Glu Trp Ile Glu Glu Gly
1               5                   10                  15

Gly Thr Trp Trp Thr Glu Trp Ser Gln
            20                  25

<210> SEQ ID NO 23
<211> LENGTH: 22
<212> TYPE: PRT
<213> ORGANISM: Homo sapiens

<400> SEQUENCE: 23

Val Met Val Thr Ile Pro Ala Asp Leu Tyr Glu Trp Ile Glu Glu Thr
1               5                   10                  15

Trp Trp Glu Thr Trp Trp
            20

<210> SEQ ID NO 24
<211> LENGTH: 20
<212> TYPE: PRT
<213> ORGANISM: Homo sapiens

<400> SEQUENCE: 24

Val Met Val Thr Ile Pro Ala Asp Leu Tyr Glu Trp Ile Glu Glu Val
1               5                   10                  15

Pro Gly Trp Gly
            20

<210> SEQ ID NO 25
<211> LENGTH: 25
<212> TYPE: PRT
<213> ORGANISM: Homo sapiens

<400> SEQUENCE: 25

Val Met Val Thr Ile Pro Ala Asp Leu Tyr Glu Trp Ile Glu Glu Gly
1               5                   10                  15

Gly Lys Glu Thr Trp Trp Glu Thr Trp
            20                  25

<210> SEQ ID NO 26
<211> LENGTH: 20
<212> TYPE: PRT
<213> ORGANISM: Homo sapiens

<400> SEQUENCE: 26

Val Met Val Thr Ile Pro Ala Asp Leu Tyr Glu Trp Ile Glu Glu Val
1               5                   10                  15

Pro Gly Lys Gly
            20

<210> SEQ ID NO 27
<211> LENGTH: 20
<212> TYPE: PRT
<213> ORGANISM: Homo sapiens

```
<400> SEQUENCE: 27

Val Met Val Thr Ile Pro Ala Asp Leu Tyr Glu Trp Ile Glu Glu Val
1               5                   10                  15

Pro Gly Ala Gly
            20

<210> SEQ ID NO 28
<211> LENGTH: 31
<212> TYPE: PRT
<213> ORGANISM: Homo sapiens

<400> SEQUENCE: 28

Val Met Val Thr Ile Pro Ala Asp Leu Tyr Glu Trp Ile Glu Glu Arg
1               5                   10                  15

Gln Ile Lys Ile Trp Phe Gln Asn Arg Arg Met Lys Trp Lys Lys
            20                  25                  30

<210> SEQ ID NO 29
<211> LENGTH: 23
<212> TYPE: PRT
<213> ORGANISM: Homo sapiens

<400> SEQUENCE: 29

Arg Arg Arg Arg Arg Arg Arg Val Met Val Thr Ile Pro Ala Asp
1               5                   10                  15

Leu Tyr Glu Trp Ile Glu Glu
            20

<210> SEQ ID NO 30
<211> LENGTH: 23
<212> TYPE: PRT
<213> ORGANISM: Homo sapiens

<400> SEQUENCE: 30

Val Met Val Thr Ile Pro Ala Asp Leu Tyr Glu Trp Ile Glu Glu Arg
1               5                   10                  15

Arg Arg Arg Arg Arg Arg
            20

<210> SEQ ID NO 31
<211> LENGTH: 23
<212> TYPE: PRT
<213> ORGANISM: Homo sapiens

<400> SEQUENCE: 31

Ala Arg Lys Lys Ala Ala Lys Ala Val Met Val Thr Ile Pro Ala Asp
1               5                   10                  15

Leu Tyr Glu Trp Ile Glu Glu
            20

<210> SEQ ID NO 32
<211> LENGTH: 25
<212> TYPE: PRT
<213> ORGANISM: Homo sapiens

<400> SEQUENCE: 32

Gly Gly Thr Trp Trp Thr Glu Trp Ser Gln Val Met Val Thr Ile Pro
1               5                   10                  15

Ala Asp Leu Tyr Glu Trp Ile Glu Glu
            20                  25
```

<210> SEQ ID NO 33
<211> LENGTH: 25
<212> TYPE: PRT
<213> ORGANISM: Homo sapiens

<400> SEQUENCE: 33

Gly Gly Lys Glu Thr Trp Trp Glu Thr Trp Val Met Val Thr Ile Pro
1               5                   10                  15

Ala Asp Leu Tyr Glu Trp Ile Glu Glu
            20                  25

<210> SEQ ID NO 34
<211> LENGTH: 20
<212> TYPE: PRT
<213> ORGANISM: Homo sapiens

<400> SEQUENCE: 34

Val Pro Gly Trp Gly Val Met Val Thr Ile Pro Ala Asp Leu Tyr Glu
1               5                   10                  15

Trp Ile Glu Glu
            20

<210> SEQ ID NO 35
<211> LENGTH: 20
<212> TYPE: PRT
<213> ORGANISM: Homo sapiens

<400> SEQUENCE: 35

Val Pro Gly Ala Gly Val Met Val Thr Ile Pro Ala Asp Leu Tyr Glu
1               5                   10                  15

Trp Ile Glu Glu
            20

<210> SEQ ID NO 36
<211> LENGTH: 20
<212> TYPE: PRT
<213> ORGANISM: Homo sapiens

<400> SEQUENCE: 36

Val Pro Gly Lys Gly Val Met Val Thr Ile Pro Ala Asp Leu Tyr Glu
1               5                   10                  15

Trp Ile Glu Glu
            20

<210> SEQ ID NO 37
<211> LENGTH: 25
<212> TYPE: PRT
<213> ORGANISM: Homo sapiens

<400> SEQUENCE: 37

Val Met Val Thr Ile Pro Ala Asp Leu Tyr Glu Trp Ile Glu Glu Val
1               5                   10                  15

Pro Gly Ala Gly Val Pro Gly Ala Gly
            20                  25

<210> SEQ ID NO 38
<211> LENGTH: 25
<212> TYPE: PRT
<213> ORGANISM: Homo sapiens

<400> SEQUENCE: 38

Val Pro Gly Ala Gly Val Pro Gly Ala Gly Val Met Val Thr Ile Pro

```
1               5                   10                  15
Ala Asp Leu Tyr Glu Trp Ile Glu Glu
        20                  25

<210> SEQ ID NO 39
<211> LENGTH: 20
<212> TYPE: PRT
<213> ORGANISM: Homo sapiens

<400> SEQUENCE: 39

Val Pro Gly Asp Gly Val Met Val Thr Ile Pro Ala Asp Leu Tyr Glu
1               5                   10                  15

Trp Ile Glu Glu
        20

<210> SEQ ID NO 40
<211> LENGTH: 20
<212> TYPE: PRT
<213> ORGANISM: Homo sapiens

<400> SEQUENCE: 40

Val Met Val Thr Ile Pro Ala Asp Leu Tyr Glu Trp Ile Glu Glu Val
1               5                   10                  15

Pro Gly Asp Gly
        20

<210> SEQ ID NO 41
<211> LENGTH: 16
<212> TYPE: PRT
<213> ORGANISM: Homo sapiens

<400> SEQUENCE: 41

Asp Leu Ser Ala Val Cys Trp Ala Phe Pro Trp Asp Pro Glu Cys His
1               5                   10                  15

<210> SEQ ID NO 42
<211> LENGTH: 15
<212> TYPE: PRT
<213> ORGANISM: Homo sapiens

<400> SEQUENCE: 42

Ile Met Val Thr Ile Pro Ala Asp Leu Tyr Glu Trp Ile Glu Glu
1               5                   10                  15

<210> SEQ ID NO 43
<211> LENGTH: 16
<212> TYPE: PRT
<213> ORGANISM: Homo sapiens

<400> SEQUENCE: 43

Ile Met Val Thr Ile Pro Ala Asp Leu Tyr Glu Trp Ile Glu Glu Gln
1               5                   10                  15

<210> SEQ ID NO 44
<211> LENGTH: 8
<212> TYPE: PRT
<213> ORGANISM: Homo sapiens

<400> SEQUENCE: 44

Ala Arg Lys Lys Ala Ala Lys Ala
1               5

<210> SEQ ID NO 45
```

```
<211> LENGTH: 8
<212> TYPE: PRT
<213> ORGANISM: Homo sapiens

<400> SEQUENCE: 45

Thr Trp Trp Thr Glu Trp Ser Gln
1               5

<210> SEQ ID NO 46
<211> LENGTH: 7
<212> TYPE: PRT
<213> ORGANISM: Homo sapiens

<400> SEQUENCE: 46

Thr Trp Trp Glu Thr Trp Trp
1               5

<210> SEQ ID NO 47
<211> LENGTH: 5
<212> TYPE: PRT
<213> ORGANISM: Homo sapiens

<400> SEQUENCE: 47

Val Pro Gly Trp Gly
1               5

<210> SEQ ID NO 48
<211> LENGTH: 8
<212> TYPE: PRT
<213> ORGANISM: Homo sapiens

<400> SEQUENCE: 48

Lys Glu Thr Trp Trp Glu Thr Trp
1               5

<210> SEQ ID NO 49
<211> LENGTH: 5
<212> TYPE: PRT
<213> ORGANISM: Homo sapiens

<400> SEQUENCE: 49

Val Pro Gly Lys Gly
1               5

<210> SEQ ID NO 50
<211> LENGTH: 5
<212> TYPE: PRT
<213> ORGANISM: Homo sapiens

<400> SEQUENCE: 50

Val Pro Gly Ala Gly
1               5

<210> SEQ ID NO 51
<211> LENGTH: 16
<212> TYPE: PRT
<213> ORGANISM: Homo sapiens

<400> SEQUENCE: 51

Arg Gln Ile Lys Ile Trp Phe Gln Asn Arg Arg Met Lys Trp Lys Lys
1               5                   10                  15

<210> SEQ ID NO 52
<211> LENGTH: 8
<212> TYPE: PRT
```

```
<213> ORGANISM: Homo sapiens

<400> SEQUENCE: 52

Arg Arg Arg Arg Arg Arg Arg Arg
1               5

<210> SEQ ID NO 53
<211> LENGTH: 5
<212> TYPE: PRT
<213> ORGANISM: Homo sapiens

<400> SEQUENCE: 53

Val Pro Gly Asp Gly
1               5

<210> SEQ ID NO 54
<211> LENGTH: 5
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 4
<223> OTHER INFORMATION: Xaa = Any Amino Acid

<400> SEQUENCE: 54

Val Pro Gly Xaa Gly
1               5

<210> SEQ ID NO 55
<211> LENGTH: 4
<212> TYPE: PRT
<213> ORGANISM: Homo sapiens

<400> SEQUENCE: 55

Ile Pro Gly Gly
1

<210> SEQ ID NO 56
<211> LENGTH: 5
<212> TYPE: PRT
<213> ORGANISM: Homo sapiens

<400> SEQUENCE: 56

Ala Val Gly Val Pro
1               5

<210> SEQ ID NO 57
<211> LENGTH: 5
<212> TYPE: PRT
<213> ORGANISM: Artificial Sequence
<220> FEATURE:
<223> OTHER INFORMATION: Synthetic generated peptide
<220> FEATURE:
<221> NAME/KEY: VARIANT
<222> LOCATION: 4
<223> OTHER INFORMATION: Xaa = Any Amino Acid

<400> SEQUENCE: 57

Ile Pro Gly Xaa Gly
1               5

<210> SEQ ID NO 58
<211> LENGTH: 5
<212> TYPE: PRT
<213> ORGANISM: Homo sapiens
```

```
<400> SEQUENCE: 58

Ile Pro Gly Val Gly
1               5

<210> SEQ ID NO 59
<211> LENGTH: 5
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 4
<223> OTHER INFORMATION: Xaa = Any Amino Acid

<400> SEQUENCE: 59

Leu Pro Gly Xaa Gly
1               5

<210> SEQ ID NO 60
<211> LENGTH: 5
<212> TYPE: PRT
<213> ORGANISM: Homo sapiens

<400> SEQUENCE: 60

Leu Pro Gly Val Gly
1               5

<210> SEQ ID NO 61
<211> LENGTH: 6
<212> TYPE: PRT
<213> ORGANISM: Homo sapiens

<400> SEQUENCE: 61

Val Ala Pro Gly Val Gly
1               5

<210> SEQ ID NO 62
<211> LENGTH: 5
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Any Amino Acid

<400> SEQUENCE: 62

Xaa Pro Gly Val Gly
1               5

<210> SEQ ID NO 63
<211> LENGTH: 8
<212> TYPE: PRT
<213> ORGANISM: Homo sapiens

<400> SEQUENCE: 63

Gly Val Gly Val Pro Gly Val Gly
1               5

<210> SEQ ID NO 64
<211> LENGTH: 9
<212> TYPE: PRT
<213> ORGANISM: Homo sapiens
```

```
<400> SEQUENCE: 64

Val Pro Gly Phe Gly Val Gly Ala Gly
1               5

<210> SEQ ID NO 65
<211> LENGTH: 8
<212> TYPE: PRT
<213> ORGANISM: Homo sapiens

<400> SEQUENCE: 65

Val Pro Gly Gly Val Pro Gly Gly
1               5

<210> SEQ ID NO 66
<211> LENGTH: 15
<212> TYPE: PRT
<213> ORGANISM: Homo sapiens

<400> SEQUENCE: 66

Ile Val Val Thr Met Pro Ala Asp Leu Trp Asp Trp Ile Lys Ala
1               5                   10                  15

<210> SEQ ID NO 67
<211> LENGTH: 15
<212> TYPE: PRT
<213> ORGANISM: Homo sapiens

<400> SEQUENCE: 67

Ile Val Val Thr Met Pro Ala Asp Leu Trp Asp Trp Ile Arg Ala
1               5                   10                  15

<210> SEQ ID NO 68
<211> LENGTH: 15
<212> TYPE: PRT
<213> ORGANISM: Homo sapiens

<400> SEQUENCE: 68

Ile Val Val Thr Met Pro Ala Asp Leu Trp Asp Trp Ile Arg Lys
1               5                   10                  15

<210> SEQ ID NO 69
<211> LENGTH: 15
<212> TYPE: PRT
<213> ORGANISM: Homo sapiens

<400> SEQUENCE: 69

Ile Val Val Thr Met Pro Ala Asp Leu Trp Asp Trp Ile Ala Ala
1               5                   10                  15

<210> SEQ ID NO 70
<211> LENGTH: 15
<212> TYPE: PRT
<213> ORGANISM: Homo sapiens

<400> SEQUENCE: 70

Ile Val Val Thr Met Pro Ala Asp Leu Trp Asp Trp Ala Arg Ala
1               5                   10                  15

<210> SEQ ID NO 71
<211> LENGTH: 15
<212> TYPE: PRT
<213> ORGANISM: Homo sapiens

<400> SEQUENCE: 71
```

Ile Val Val Thr Met Pro Ala Asp Leu Trp Ala Trp Ile Arg Ala
1               5                   10                  15

<210> SEQ ID NO 72
<211> LENGTH: 15
<212> TYPE: PRT
<213> ORGANISM: Homo sapiens

<400> SEQUENCE: 72

Ile Val Val Thr Met Pro Ala Asp Leu Ala Asp Trp Ile Arg Ala
1               5                   10                  15

<210> SEQ ID NO 73
<211> LENGTH: 15
<212> TYPE: PRT
<213> ORGANISM: Homo sapiens

<400> SEQUENCE: 73

Ile Val Val Thr Met Pro Ala Asp Ala Trp Asp Trp Ile Arg Ala
1               5                   10                  15

<210> SEQ ID NO 74
<211> LENGTH: 15
<212> TYPE: PRT
<213> ORGANISM: Homo sapiens

<400> SEQUENCE: 74

Ile Val Val Thr Met Pro Ala Asp Leu Trp Asp Trp Ile Arg Ala
1               5                   10                  15

<210> SEQ ID NO 75
<211> LENGTH: 15
<212> TYPE: PRT
<213> ORGANISM: Homo sapiens

<400> SEQUENCE: 75

Ile Val Val Thr Ala Pro Ala Asp Leu Trp Asp Trp Ile Arg Ala
1               5                   10                  15

<210> SEQ ID NO 76
<211> LENGTH: 15
<212> TYPE: PRT
<213> ORGANISM: Homo sapiens

<400> SEQUENCE: 76

Ile Val Val Ala Met Pro Ala Asp Leu Trp Asp Trp Ile Arg Ala
1               5                   10                  15

<210> SEQ ID NO 77
<211> LENGTH: 15
<212> TYPE: PRT
<213> ORGANISM: Homo sapiens

<400> SEQUENCE: 77

Ile Ala Val Thr Met Pro Ala Asp Leu Trp Asp Trp Ile Arg Ala
1               5                   10                  15

<210> SEQ ID NO 78
<211> LENGTH: 15
<212> TYPE: PRT
<213> ORGANISM: Homo sapiens

<400> SEQUENCE: 78

Ala Val Val Thr Met Pro Ala Asp Leu Trp Asp Trp Ile Arg Ala
1               5                   10                  15

<210> SEQ ID NO 79
<211> LENGTH: 15
<212> TYPE: PRT
<213> ORGANISM: Homo sapiens

<400> SEQUENCE: 79

Ile His Val Thr Met Pro Ala Asp Leu Trp Asp Trp Ile Arg Ala
1               5                   10                  15

<210> SEQ ID NO 80
<211> LENGTH: 15
<212> TYPE: PRT
<213> ORGANISM: Homo sapiens

<400> SEQUENCE: 80

Ile Gln Val Thr Met Pro Ala Asp Leu Trp Asp Trp Ile Arg Ala
1               5                   10                  15

<210> SEQ ID NO 81
<211> LENGTH: 15
<212> TYPE: PRT
<213> ORGANISM: Homo sapiens

<400> SEQUENCE: 81

Ile Arg Val Thr Met Pro Ala Asp Leu Trp Asp Trp Ile Arg Ala
1               5                   10                  15

<210> SEQ ID NO 82
<211> LENGTH: 15
<212> TYPE: PRT
<213> ORGANISM: Homo sapiens

<400> SEQUENCE: 82

Ile Thr Val Thr Met Pro Ala Asp Leu Trp Asp Trp Ile Arg Ala
1               5                   10                  15

<210> SEQ ID NO 83
<211> LENGTH: 15
<212> TYPE: PRT
<213> ORGANISM: Homo sapiens

<400> SEQUENCE: 83

Ile Trp Val Thr Met Pro Ala Asp Leu Trp Asp Trp Ile Arg Ala
1               5                   10                  15

<210> SEQ ID NO 84
<211> LENGTH: 15
<212> TYPE: PRT
<213> ORGANISM: Homo sapiens

<400> SEQUENCE: 84

Ile Tyr Val Thr Met Pro Ala Asp Leu Trp Asp Trp Ile Arg Ala
1               5                   10                  15

<210> SEQ ID NO 85
<211> LENGTH: 15
<212> TYPE: PRT
<213> ORGANISM: Homo sapiens

<400> SEQUENCE: 85

Ile Val Val Thr Ile Pro Ala Asp Leu Trp Asp Trp Ile Arg Ala
1               5                   10                  15

```
<210> SEQ ID NO 86
<211> LENGTH: 15
<212> TYPE: PRT
<213> ORGANISM: Homo sapiens

<400> SEQUENCE: 86

Ile Val Val Thr Leu Pro Ala Asp Leu Trp Asp Trp Ile Arg Ala
1               5                   10                  15

<210> SEQ ID NO 87
<211> LENGTH: 15
<212> TYPE: PRT
<213> ORGANISM: Homo sapiens

<400> SEQUENCE: 87

Ile Val Val Thr Val Pro Ala Asp Leu Trp Asp Trp Ile Arg Ala
1               5                   10                  15

<210> SEQ ID NO 88
<211> LENGTH: 15
<212> TYPE: PRT
<213> ORGANISM: Homo sapiens

<400> SEQUENCE: 88

Ile Val Val Thr Met Pro Ala Asp Leu Trp Asp Trp Ile Met Ala
1               5                   10                  15

<210> SEQ ID NO 89
<211> LENGTH: 15
<212> TYPE: PRT
<213> ORGANISM: Homo sapiens

<400> SEQUENCE: 89

Ile Val Val Thr Met Pro Ala Asp Leu Trp Asp Trp Ile Asn Ala
1               5                   10                  15

<210> SEQ ID NO 90
<211> LENGTH: 15
<212> TYPE: PRT
<213> ORGANISM: Homo sapiens

<400> SEQUENCE: 90

Ile Val Val Thr Met Pro Ala Asp Leu Trp Asp Trp Ile Gln Ala
1               5                   10                  15

<210> SEQ ID NO 91
<211> LENGTH: 15
<212> TYPE: PRT
<213> ORGANISM: Homo sapiens

<400> SEQUENCE: 91

Ile Val Val Thr Ile Pro Ala Asp Leu Trp Asp Trp Ile Arg Ala
1               5                   10                  15

<210> SEQ ID NO 92
<211> LENGTH: 15
<212> TYPE: PRT
<213> ORGANISM: Homo sapiens

<400> SEQUENCE: 92

Ile Val Val Thr Leu Pro Ala Asp Leu Trp Asp Trp Ile Arg Ala
1               5                   10                  15

<210> SEQ ID NO 93
<211> LENGTH: 15
```

```
<212> TYPE: PRT
<213> ORGANISM: Homo sapiens

<400> SEQUENCE: 93

Ile His Val Thr Ile Pro Ala Asp Leu Trp Asp Trp Ile Asn Lys
1               5                   10                  15

<210> SEQ ID NO 94
<211> LENGTH: 14
<212> TYPE: PRT
<213> ORGANISM: Homo sapiens

<400> SEQUENCE: 94

Ile His Val Thr Ile Pro Ala Asp Leu Trp Asp Trp Ile Asn
1               5                   10

<210> SEQ ID NO 95
<211> LENGTH: 13
<212> TYPE: PRT
<213> ORGANISM: Homo sapiens

<400> SEQUENCE: 95

Ile His Val Thr Ile Pro Ala Asp Leu Trp Asp Trp Ile
1               5                   10

<210> SEQ ID NO 96
<211> LENGTH: 20
<212> TYPE: PRT
<213> ORGANISM: Homo sapiens

<400> SEQUENCE: 96

Asp Ser Ser Ala Val Cys Trp Ala Phe Pro His His Pro Leu Cys His
1               5                   10                  15

Met Lys Ala Thr
            20

<210> SEQ ID NO 97
<211> LENGTH: 16
<212> TYPE: PRT
<213> ORGANISM: Homo sapiens

<400> SEQUENCE: 97

Ala Asp Ala Asp Met Cys Trp Phe Phe Pro Thr Ser Pro Trp Cys His
1               5                   10                  15

<210> SEQ ID NO 98
<211> LENGTH: 17
<212> TYPE: PRT
<213> ORGANISM: Homo sapiens

<400> SEQUENCE: 98

Asp Leu Ser Ala Val Cys Trp Ala Phe Pro Trp Asp Pro Glu Cys His
1               5                   10                  15

Met

<210> SEQ ID NO 99
<211> LENGTH: 16
<212> TYPE: PRT
<213> ORGANISM: Homo sapiens

<400> SEQUENCE: 99

Asp Ser Ser Ala Val Cys Trp Ala Phe Pro Tyr Leu Pro Glu Cys His
1               5                   10                  15
```

```
<210> SEQ ID NO 100
<211> LENGTH: 16
<212> TYPE: PRT
<213> ORGANISM: Homo sapiens

<400> SEQUENCE: 100

Asp Ile Ser Ala Val Cys Trp Ala Phe Pro Phe Asp Pro Glu Cys His
1               5                   10                  15

<210> SEQ ID NO 101
<211> LENGTH: 20
<212> TYPE: PRT
<213> ORGANISM: Homo sapiens

<400> SEQUENCE: 101

Ala Tyr Glu Cys Pro Arg Leu Glu Tyr Asp Met Phe Gly Ala Leu His
1               5                   10                  15

Cys Leu Pro Ser
            20

<210> SEQ ID NO 102
<211> LENGTH: 15
<212> TYPE: PRT
<213> ORGANISM: Homo sapiens

<400> SEQUENCE: 102

Cys Pro Arg Leu Glu Tyr Asp Met Phe Gly Ala Leu His Cys Leu
1               5                   10                  15

<210> SEQ ID NO 103
<211> LENGTH: 15
<212> TYPE: PRT
<213> ORGANISM: Homo sapiens

<400> SEQUENCE: 103

Cys Leu Asp Leu Gln Tyr Asp Pro Trp Gly Ala Leu His Cys Ile
1               5                   10                  15

<210> SEQ ID NO 104
<211> LENGTH: 15
<212> TYPE: PRT
<213> ORGANISM: Homo sapiens

<400> SEQUENCE: 104

Cys Phe Asp Leu Gln Tyr Asp Pro Trp Gly Ala Leu His Cys Ile
1               5                   10                  15

<210> SEQ ID NO 105
<211> LENGTH: 15
<212> TYPE: PRT
<213> ORGANISM: Homo sapiens

<400> SEQUENCE: 105

Cys Leu Asp Leu Gln Tyr Asp Met Phe Gly Ala Leu His Cys Val
1               5                   10                  15

<210> SEQ ID NO 106
<211> LENGTH: 15
<212> TYPE: PRT
<213> ORGANISM: Homo sapiens

<400> SEQUENCE: 106

Cys Leu Asp Leu Val Tyr Asp Pro Trp Gly Ala Leu His Cys Ile
1               5                   10                  15
```

<210> SEQ ID NO 107
<211> LENGTH: 15
<212> TYPE: PRT
<213> ORGANISM: Homo sapiens

<400> SEQUENCE: 107

Cys Trp Val Leu Glu Tyr Asp Met Phe Gly Ala Leu His Cys Arg
1               5                   10                  15

<210> SEQ ID NO 108
<211> LENGTH: 15
<212> TYPE: PRT
<213> ORGANISM: Homo sapiens

<400> SEQUENCE: 108

Cys Trp Ala Leu Glu Tyr Asp Met Phe Gly Tyr Leu His Cys Arg
1               5                   10                  15

<210> SEQ ID NO 109
<211> LENGTH: 15
<212> TYPE: PRT
<213> ORGANISM: Homo sapiens

<400> SEQUENCE: 109

Cys Trp Val Leu Glu Tyr Asp Met Phe Gly Phe Leu His Cys Arg
1               5                   10                  15

<210> SEQ ID NO 110
<211> LENGTH: 15
<212> TYPE: PRT
<213> ORGANISM: Homo sapiens

<400> SEQUENCE: 110

Cys Trp Val Leu Glu Tyr Asp Met Phe Gly Tyr Leu His Cys Arg
1               5                   10                  15

<210> SEQ ID NO 111
<211> LENGTH: 15
<212> TYPE: PRT
<213> ORGANISM: Homo sapiens

<400> SEQUENCE: 111

Val His Val Thr Ile Pro Ala Glu Leu Trp Glu Trp Val Arg Arg
1               5                   10                  15

<210> SEQ ID NO 112
<211> LENGTH: 15
<212> TYPE: PRT
<213> ORGANISM: Homo sapiens

<400> SEQUENCE: 112

Val His Phe Thr Ile Pro Ala Asp Leu Trp Glu Trp Val Arg Arg
1               5                   10                  15

<210> SEQ ID NO 113
<211> LENGTH: 15
<212> TYPE: PRT
<213> ORGANISM: Homo sapiens

<400> SEQUENCE: 113

Val His Val Gln Ile Pro Ala Asp Leu Trp Glu Trp Val Arg Arg
1               5                   10                  15

```
<210> SEQ ID NO 114
<211> LENGTH: 15
<212> TYPE: PRT
<213> ORGANISM: Homo sapiens

<400> SEQUENCE: 114

Val His Val Thr Phe Pro Ala Asp Leu Trp Glu Trp Val Arg Arg
1               5                   10                  15

<210> SEQ ID NO 115
<211> LENGTH: 15
<212> TYPE: PRT
<213> ORGANISM: Homo sapiens

<400> SEQUENCE: 115

Val His Val Thr Ile Pro Gln Asp Leu Trp Glu Trp Val Arg Arg
1               5                   10                  15

<210> SEQ ID NO 116
<211> LENGTH: 15
<212> TYPE: PRT
<213> ORGANISM: Homo sapiens

<400> SEQUENCE: 116

Val His Val Thr Ile Pro Ala Asn Leu Trp Glu Trp Val Arg Arg
1               5                   10                  15

<210> SEQ ID NO 117
<211> LENGTH: 15
<212> TYPE: PRT
<213> ORGANISM: Homo sapiens

<400> SEQUENCE: 117

Val His Val Thr Ile Pro Ala Asp Phe Trp Glu Trp Val Arg Arg
1               5                   10                  15

<210> SEQ ID NO 118
<211> LENGTH: 15
<212> TYPE: PRT
<213> ORGANISM: Homo sapiens

<400> SEQUENCE: 118

Val His Val Thr Ile Pro Ala Asp Leu Tyr Glu Trp Val Arg Arg
1               5                   10                  15

<210> SEQ ID NO 119
<211> LENGTH: 15
<212> TYPE: PRT
<213> ORGANISM: Homo sapiens

<400> SEQUENCE: 119

Val His Val Thr Ile Pro Ala Asp Leu Trp Asn Trp Val Arg Arg
1               5                   10                  15

<210> SEQ ID NO 120
<211> LENGTH: 15
<212> TYPE: PRT
<213> ORGANISM: Homo sapiens

<400> SEQUENCE: 120

Val His Val Thr Ile Pro Ala Asp Leu Trp Glu Phe Val Arg Arg
1               5                   10                  15

<210> SEQ ID NO 121
<211> LENGTH: 15
```

```
<212> TYPE: PRT
<213> ORGANISM: Homo sapiens

<400> SEQUENCE: 121

Val His Val Thr Ile Pro Ala Asp Leu Trp Glu Trp Phe Arg Arg
1               5                   10                  15

<210> SEQ ID NO 122
<211> LENGTH: 15
<212> TYPE: PRT
<213> ORGANISM: Homo sapiens

<400> SEQUENCE: 122

Val His Val Tyr Ile Pro Ala Glu Leu Trp Glu Trp Val Arg Arg
1               5                   10                  15

<210> SEQ ID NO 123
<211> LENGTH: 15
<212> TYPE: PRT
<213> ORGANISM: Homo sapiens

<400> SEQUENCE: 123

Val His Val Thr Ile Pro Ala Glu Trp Trp Glu Trp Val Arg Arg
1               5                   10                  15

<210> SEQ ID NO 124
<211> LENGTH: 15
<212> TYPE: PRT
<213> ORGANISM: Homo sapiens

<400> SEQUENCE: 124

Val His Phe Thr Phe Pro Gln Asp Leu Trp Glu Trp Val Arg Arg
1               5                   10                  15

<210> SEQ ID NO 125
<211> LENGTH: 15
<212> TYPE: PRT
<213> ORGANISM: Homo sapiens

<400> SEQUENCE: 125

Val His Phe Thr Phe Pro Gln Asp Phe Trp Glu Trp Val Arg Arg
1               5                   10                  15

<210> SEQ ID NO 126
<211> LENGTH: 15
<212> TYPE: PRT
<213> ORGANISM: Homo sapiens

<400> SEQUENCE: 126

Val His Phe Thr Ile Pro Gln Asp Leu Tyr Glu Trp Val Arg Arg
1               5                   10                  15

<210> SEQ ID NO 127
<211> LENGTH: 15
<212> TYPE: PRT
<213> ORGANISM: Homo sapiens

<400> SEQUENCE: 127

Val His Phe Thr Phe Pro Gln Asp Leu Trp Asn Trp Val Arg Arg
1               5                   10                  15

<210> SEQ ID NO 128
<211> LENGTH: 15
<212> TYPE: PRT
<213> ORGANISM: Homo sapiens
```

```
<400> SEQUENCE: 128

Val His Phe Thr Phe Pro Gln Asp Leu Trp Glu Phe Val Arg Arg
1               5                   10                  15

<210> SEQ ID NO 129
<211> LENGTH: 15
<212> TYPE: PRT
<213> ORGANISM: Homo sapiens

<400> SEQUENCE: 129

Val His Phe Thr Phe Pro Gln Asp Leu Trp Glu Trp Phe Arg Arg
1               5                   10                  15

<210> SEQ ID NO 130
<211> LENGTH: 15
<212> TYPE: PRT
<213> ORGANISM: Homo sapiens

<400> SEQUENCE: 130

Val His Phe Gln Phe Pro Ala Asp Leu Trp Glu Trp Val Arg Arg
1               5                   10                  15

<210> SEQ ID NO 131
<211> LENGTH: 15
<212> TYPE: PRT
<213> ORGANISM: Homo sapiens

<400> SEQUENCE: 131

Val His Phe Gln Phe Pro Ala Asp Phe Trp Glu Trp Val Arg Arg
1               5                   10                  15

<210> SEQ ID NO 132
<211> LENGTH: 15
<212> TYPE: PRT
<213> ORGANISM: Homo sapiens

<400> SEQUENCE: 132

Val His Phe Gln Phe Pro Ala Asp Leu Tyr Glu Trp Val Arg Arg
1               5                   10                  15

<210> SEQ ID NO 133
<211> LENGTH: 15
<212> TYPE: PRT
<213> ORGANISM: Homo sapiens

<400> SEQUENCE: 133

Val His Phe Gln Phe Pro Ala Asp Leu Trp Asn Trp Val Arg Arg
1               5                   10                  15

<210> SEQ ID NO 134
<211> LENGTH: 15
<212> TYPE: PRT
<213> ORGANISM: Homo sapiens

<400> SEQUENCE: 134

Val His Phe Gln Phe Pro Ala Asp Leu Trp Glu Phe Val Arg Arg
1               5                   10                  15

<210> SEQ ID NO 135
<211> LENGTH: 15
<212> TYPE: PRT
<213> ORGANISM: Homo sapiens

<400> SEQUENCE: 135
```

Val His Phe Gln Phe Pro Ala Asp Leu Trp Glu Trp Phe Arg Arg
1               5                   10                  15

<210> SEQ ID NO 136
<211> LENGTH: 15
<212> TYPE: PRT
<213> ORGANISM: Homo sapiens

<400> SEQUENCE: 136

Val His Phe Gln Phe Pro Gln Asp Trp Trp Glu Trp Val Arg Arg
1               5                   10                  15

<210> SEQ ID NO 137
<211> LENGTH: 15
<212> TYPE: PRT
<213> ORGANISM: Homo sapiens

<400> SEQUENCE: 137

Val His Phe Gln Ile Pro Gln Asp Trp Trp Glu Trp Val Arg Arg
1               5                   10                  15

<210> SEQ ID NO 138
<211> LENGTH: 15
<212> TYPE: PRT
<213> ORGANISM: Homo sapiens

<400> SEQUENCE: 138

Val His Phe Gln Ile Phe Gln Asp Trp Trp Glu Trp Val Arg Arg
1               5                   10                  15

<210> SEQ ID NO 139
<211> LENGTH: 15
<212> TYPE: PRT
<213> ORGANISM: Homo sapiens

<400> SEQUENCE: 139

Val His Phe Gln Phe Pro Gln Asp Trp Trp Asn Trp Val Arg Arg
1               5                   10                  15

<210> SEQ ID NO 140
<211> LENGTH: 15
<212> TYPE: PRT
<213> ORGANISM: Homo sapiens

<400> SEQUENCE: 140

Val His Phe Gln Phe Pro Gln Asp Leu Trp Glu Phe Val Arg Arg
1               5                   10                  15

<210> SEQ ID NO 141
<211> LENGTH: 15
<212> TYPE: PRT
<213> ORGANISM: Homo sapiens

<400> SEQUENCE: 141

Val His Phe Gln Phe Pro Gln Asp Trp Trp Glu Trp Phe Arg Arg
1               5                   10                  15

<210> SEQ ID NO 142
<211> LENGTH: 15
<212> TYPE: PRT
<213> ORGANISM: Homo sapiens

<400> SEQUENCE: 142

Val His Phe Thr Ile Pro Ala Asp Phe Trp Glu Trp Phe Arg Arg

-continued

```
1               5                   10                  15
```

<210> SEQ ID NO 143
<211> LENGTH: 15
<212> TYPE: PRT
<213> ORGANISM: Homo sapiens

<400> SEQUENCE: 143

```
Val His Val Gln Ile Pro Ala Asp Phe Trp Glu Trp Phe Arg Arg
1               5                   10                  15
```

<210> SEQ ID NO 144
<211> LENGTH: 15
<212> TYPE: PRT
<213> ORGANISM: Homo sapiens

<400> SEQUENCE: 144

```
Val His Val Thr Phe Pro Ala Asp Leu Trp Glu Trp Phe Arg Arg
1               5                   10                  15
```

<210> SEQ ID NO 145
<211> LENGTH: 15
<212> TYPE: PRT
<213> ORGANISM: Homo sapiens

<400> SEQUENCE: 145

```
Val His Val Thr Ile Pro Gln Asp Phe Trp Glu Trp Phe Arg Arg
1               5                   10                  15
```

<210> SEQ ID NO 146
<211> LENGTH: 15
<212> TYPE: PRT
<213> ORGANISM: Homo sapiens

<400> SEQUENCE: 146

```
Val His Phe Thr Ile Pro Gln Asp Trp Trp Glu Trp Val Arg Arg
1               5                   10                  15
```

<210> SEQ ID NO 147
<211> LENGTH: 15
<212> TYPE: PRT
<213> ORGANISM: Homo sapiens

<400> SEQUENCE: 147

```
Val His Phe Thr Phe Pro Gln Asp Leu Tyr Asn Trp Val Arg Arg
1               5                   10                  15
```

<210> SEQ ID NO 148
<211> LENGTH: 15
<212> TYPE: PRT
<213> ORGANISM: Homo sapiens

<400> SEQUENCE: 148

```
Val His Phe Thr Phe Pro Gln Asp Leu Tyr Asn Phe Val Arg Arg
1               5                   10                  15
```

<210> SEQ ID NO 149
<211> LENGTH: 15
<212> TYPE: PRT
<213> ORGANISM: Homo sapiens

<400> SEQUENCE: 149

```
Val His Val Thr Ile Pro Ala Asp Leu Tyr Asn Phe Arg Arg
1               5                   10                  15
```

```
<210> SEQ ID NO 150
<211> LENGTH: 15
<212> TYPE: PRT
<213> ORGANISM: Homo sapiens

<400> SEQUENCE: 150

Val His Phe Gln Phe Pro Gln Asp Leu Trp Glu Trp Val Arg Arg
1               5                   10                  15

<210> SEQ ID NO 151
<211> LENGTH: 14
<212> TYPE: PRT
<213> ORGANISM: Homo sapiens

<400> SEQUENCE: 151

Val His Phe Thr Ile Pro Gln Asp Leu Tyr Asn Trp Arg Arg
1               5                   10

<210> SEQ ID NO 152
<211> LENGTH: 15
<212> TYPE: PRT
<213> ORGANISM: Homo sapiens

<400> SEQUENCE: 152

Val His Phe Thr Ile Pro Ala Asp Leu Tyr Asn Phe Val Arg Arg
1               5                   10                  15

<210> SEQ ID NO 153
<211> LENGTH: 15
<212> TYPE: PRT
<213> ORGANISM: Homo sapiens

<400> SEQUENCE: 153

Val His Phe Gln Ile Pro Gln Asp Leu Tyr Asn Phe Arg Arg
1               5                   10                  15

<210> SEQ ID NO 154
<211> LENGTH: 15
<212> TYPE: PRT
<213> ORGANISM: Homo sapiens

<400> SEQUENCE: 154

Val His Phe Gln Phe Pro Gln Glu Trp Tyr Asn Trp Phe Arg Arg
1               5                   10                  15

<210> SEQ ID NO 155
<211> LENGTH: 15
<212> TYPE: PRT
<213> ORGANISM: Homo sapiens

<400> SEQUENCE: 155

Val Arg Phe Gln Phe Gly Gln Glu Trp Tyr Asn Phe Phe Arg Arg
1               5                   10                  15

<210> SEQ ID NO 156
<211> LENGTH: 15
<212> TYPE: PRT
<213> ORGANISM: Homo sapiens

<400> SEQUENCE: 156

Val Pro Gly Ala Gly Val Pro Gly Ala Gly Ile His Val Thr Ile
1               5                   10                  15

<210> SEQ ID NO 157
```

```
<211> LENGTH: 17
<212> TYPE: PRT
<213> ORGANISM: Homo sapiens

<400> SEQUENCE: 157

Val Pro Gly Ala Gly Val Pro Gly Ala Gly Ile His Val Thr Ile Pro
1               5                   10                  15

Ala

<210> SEQ ID NO 158
<211> LENGTH: 15
<212> TYPE: PRT
<213> ORGANISM: Homo sapiens

<400> SEQUENCE: 158

Ala His Val Thr Ile Pro Ala Asp Leu Trp Asp Trp Ile Asn Lys
1               5                   10                  15

<210> SEQ ID NO 159
<211> LENGTH: 15
<212> TYPE: PRT
<213> ORGANISM: Homo sapiens

<400> SEQUENCE: 159

Gly His Val Thr Ile Pro Ala Asp Leu Trp Asp Trp Ile Asn Lys
1               5                   10                  15

<210> SEQ ID NO 160
<211> LENGTH: 15
<212> TYPE: PRT
<213> ORGANISM: Homo sapiens

<400> SEQUENCE: 160

Leu His Val Thr Ile Pro Ala Asp Leu Trp Asp Trp Ile Asn Lys
1               5                   10                  15

<210> SEQ ID NO 161
<211> LENGTH: 15
<212> TYPE: PRT
<213> ORGANISM: Homo sapiens

<400> SEQUENCE: 161

Pro His Val Thr Ile Pro Ala Asp Leu Trp Asp Trp Ile Asn Lys
1               5                   10                  15

<210> SEQ ID NO 162
<211> LENGTH: 15
<212> TYPE: PRT
<213> ORGANISM: Homo sapiens

<400> SEQUENCE: 162

Ile Arg Val Thr Ile Pro Ala Asp Leu Trp Asp Trp Ile Asn Lys
1               5                   10                  15

<210> SEQ ID NO 163
<211> LENGTH: 15
<212> TYPE: PRT
<213> ORGANISM: Homo sapiens

<400> SEQUENCE: 163

Ile Lys Val Thr Ile Pro Ala Asp Leu Trp Asp Trp Ile Asn Lys
1               5                   10                  15

<210> SEQ ID NO 164
```

```
<210> SEQ ID NO 164
<211> LENGTH: 15
<212> TYPE: PRT
<213> ORGANISM: Homo sapiens

<400> SEQUENCE: 164

Ile Glu Val Thr Ile Pro Ala Asp Leu Trp Asp Trp Ile Asn Lys
1               5                   10                  15

<210> SEQ ID NO 165
<211> LENGTH: 15
<212> TYPE: PRT
<213> ORGANISM: Homo sapiens

<400> SEQUENCE: 165

Ile Gln Val Thr Ile Pro Ala Asp Leu Trp Asp Trp Ile Asn Lys
1               5                   10                  15

<210> SEQ ID NO 166
<211> LENGTH: 15
<212> TYPE: PRT
<213> ORGANISM: Homo sapiens

<400> SEQUENCE: 166

Ile Tyr Val Thr Ile Pro Ala Asp Leu Trp Asp Trp Ile Asn Lys
1               5                   10                  15

<210> SEQ ID NO 167
<211> LENGTH: 15
<212> TYPE: PRT
<213> ORGANISM: Homo sapiens

<400> SEQUENCE: 167

Ile His Ala Thr Ile Pro Ala Asp Leu Trp Asp Trp Ile Asn Lys
1               5                   10                  15

<210> SEQ ID NO 168
<211> LENGTH: 15
<212> TYPE: PRT
<213> ORGANISM: Homo sapiens

<400> SEQUENCE: 168

Ile His Gly Thr Ile Pro Ala Asp Leu Trp Asp Trp Ile Asn Lys
1               5                   10                  15

<210> SEQ ID NO 169
<211> LENGTH: 15
<212> TYPE: PRT
<213> ORGANISM: Homo sapiens

<400> SEQUENCE: 169

Ile His Leu Thr Ile Pro Ala Asp Leu Trp Asp Trp Ile Asn Lys
1               5                   10                  15

<210> SEQ ID NO 170
<211> LENGTH: 15
<212> TYPE: PRT
<213> ORGANISM: Homo sapiens

<400> SEQUENCE: 170

Ile His Pro Thr Ile Pro Ala Asp Leu Trp Asp Trp Ile Asn Lys
1               5                   10                  15

<210> SEQ ID NO 171
<211> LENGTH: 15
<212> TYPE: PRT
```

<213> ORGANISM: Homo sapiens

<400> SEQUENCE: 171

Ile His Ile Thr Ile Pro Ala Asp Leu Trp Asp Trp Ile Asn Lys
1               5                   10                  15

<210> SEQ ID NO 172
<211> LENGTH: 15
<212> TYPE: PRT
<213> ORGANISM: Homo sapiens

<400> SEQUENCE: 172

Ile His Tyr Thr Ile Pro Ala Asp Leu Trp Asp Trp Ile Asn Lys
1               5                   10                  15

<210> SEQ ID NO 173
<211> LENGTH: 15
<212> TYPE: PRT
<213> ORGANISM: Homo sapiens

<400> SEQUENCE: 173

Ile His Trp Thr Ile Pro Ala Asp Leu Trp Asp Trp Ile Asn Lys
1               5                   10                  15

<210> SEQ ID NO 174
<211> LENGTH: 15
<212> TYPE: PRT
<213> ORGANISM: Homo sapiens

<400> SEQUENCE: 174

Ile His Phe Thr Ile Pro Ala Asp Leu Trp Asp Trp Ile Asn Lys
1               5                   10                  15

<210> SEQ ID NO 175
<211> LENGTH: 15
<212> TYPE: PRT
<213> ORGANISM: Homo sapiens

<400> SEQUENCE: 175

Ile His Val Ser Ile Pro Ala Asp Leu Trp Asp Trp Ile Asn Lys
1               5                   10                  15

<210> SEQ ID NO 176
<211> LENGTH: 15
<212> TYPE: PRT
<213> ORGANISM: Homo sapiens

<400> SEQUENCE: 176

Ile His Val Tyr Ile Pro Ala Asp Leu Trp Asp Trp Ile Asn Lys
1               5                   10                  15

<210> SEQ ID NO 177
<211> LENGTH: 15
<212> TYPE: PRT
<213> ORGANISM: Homo sapiens

<400> SEQUENCE: 177

Ile His Val Asn Ile Pro Ala Asp Leu Trp Asp Trp Ile Asn Lys
1               5                   10                  15

<210> SEQ ID NO 178
<211> LENGTH: 15
<212> TYPE: PRT
<213> ORGANISM: Homo sapiens -continued

<400> SEQUENCE: 178

Ile His Val Gln Ile Pro Ala Asp Leu Trp Asp Trp Ile Asn Lys
1               5                   10                  15

<210> SEQ ID NO 179
<211> LENGTH: 15
<212> TYPE: PRT
<213> ORGANISM: Homo sapiens

<400> SEQUENCE: 179

Ile His Val Thr Ala Pro Ala Asp Leu Trp Asp Trp Ile Asn Lys
1               5                   10                  15

<210> SEQ ID NO 180
<211> LENGTH: 15
<212> TYPE: PRT
<213> ORGANISM: Homo sapiens

<400> SEQUENCE: 180

Ile His Val Thr Gly Pro Ala Asp Leu Trp Asp Trp Ile Asn Lys
1               5                   10                  15

<210> SEQ ID NO 181
<211> LENGTH: 15
<212> TYPE: PRT
<213> ORGANISM: Homo sapiens

<400> SEQUENCE: 181

Ile His Val Thr Leu Pro Ala Asp Leu Trp Asp Trp Ile Asn Lys
1               5                   10                  15

<210> SEQ ID NO 182
<211> LENGTH: 15
<212> TYPE: PRT
<213> ORGANISM: Homo sapiens

<400> SEQUENCE: 182

Ile His Val Thr Pro Pro Ala Asp Leu Trp Asp Trp Ile Asn Lys
1               5                   10                  15

<210> SEQ ID NO 183
<211> LENGTH: 15
<212> TYPE: PRT
<213> ORGANISM: Homo sapiens

<400> SEQUENCE: 183

Ile His Val Thr Val Pro Ala Asp Leu Trp Asp Trp Ile Asn Lys
1               5                   10                  15

<210> SEQ ID NO 184
<211> LENGTH: 15
<212> TYPE: PRT
<213> ORGANISM: Homo sapiens

<400> SEQUENCE: 184

Ile His Val Thr Phe Pro Ala Asp Leu Trp Asp Trp Ile Asn Lys
1               5                   10                  15

<210> SEQ ID NO 185
<211> LENGTH: 15
<212> TYPE: PRT
<213> ORGANISM: Homo sapiens

<400> SEQUENCE: 185

Ile His Val Thr Tyr Pro Ala Asp Leu Trp Asp Trp Ile Asn Lys
1               5                   10                  15

<210> SEQ ID NO 186
<211> LENGTH: 15
<212> TYPE: PRT
<213> ORGANISM: Homo sapiens

<400> SEQUENCE: 186

Ile His Val Thr Ile Ala Ala Asp Leu Trp Asp Trp Ile Asn Lys
1               5                   10                  15

<210> SEQ ID NO 187
<211> LENGTH: 15
<212> TYPE: PRT
<213> ORGANISM: Homo sapiens

<400> SEQUENCE: 187

Ile His Val Thr Ile Gly Ala Asp Leu Trp Asp Trp Ile Asn Lys
1               5                   10                  15

<210> SEQ ID NO 188
<211> LENGTH: 15
<212> TYPE: PRT
<213> ORGANISM: Homo sapiens

<400> SEQUENCE: 188

Ile His Val Thr Ile Leu Ala Asp Leu Trp Asp Trp Ile Asn Lys
1               5                   10                  15

<210> SEQ ID NO 189
<211> LENGTH: 15
<212> TYPE: PRT
<213> ORGANISM: Homo sapiens

<400> SEQUENCE: 189

Ile His Val Thr Ile Val Ala Asp Leu Trp Asp Trp Ile Asn Lys
1               5                   10                  15

<210> SEQ ID NO 190
<211> LENGTH: 15
<212> TYPE: PRT
<213> ORGANISM: Homo sapiens

<400> SEQUENCE: 190

Ile His Val Thr Ile Ile Ala Asp Leu Trp Asp Trp Ile Asn Lys
1               5                   10                  15

<210> SEQ ID NO 191
<211> LENGTH: 15
<212> TYPE: PRT
<213> ORGANISM: Homo sapiens

<400> SEQUENCE: 191

Ile His Val Thr Ile Asn Ala Asp Leu Trp Asp Trp Ile Asn Lys
1               5                   10                  15

<210> SEQ ID NO 192
<211> LENGTH: 15
<212> TYPE: PRT
<213> ORGANISM: Homo sapiens

<400> SEQUENCE: 192

Ile His Val Thr Ile Pro Gly Asp Leu Trp Asp Trp Ile Asn Lys
1               5                   10                  15

```
<210> SEQ ID NO 193
<211> LENGTH: 15
<212> TYPE: PRT
<213> ORGANISM: Homo sapiens

<400> SEQUENCE: 193

Ile His Val Thr Ile Pro Leu Asp Leu Trp Asp Trp Ile Asn Lys
1               5                   10                  15

<210> SEQ ID NO 194
<211> LENGTH: 15
<212> TYPE: PRT
<213> ORGANISM: Homo sapiens

<400> SEQUENCE: 194

Ile His Val Thr Ile Pro Pro Asp Leu Trp Asp Trp Ile Asn Lys
1               5                   10                  15

<210> SEQ ID NO 195
<211> LENGTH: 15
<212> TYPE: PRT
<213> ORGANISM: Homo sapiens

<400> SEQUENCE: 195

Ile His Val Thr Ile Pro Val Asp Leu Trp Asp Trp Ile Asn Lys
1               5                   10                  15

<210> SEQ ID NO 196
<211> LENGTH: 15
<212> TYPE: PRT
<213> ORGANISM: Homo sapiens

<400> SEQUENCE: 196

Ile His Val Thr Ile Pro Ile Asp Leu Trp Asp Trp Ile Asn Lys
1               5                   10                  15

<210> SEQ ID NO 197
<211> LENGTH: 15
<212> TYPE: PRT
<213> ORGANISM: Homo sapiens

<400> SEQUENCE: 197

Ile His Val Thr Ile Pro Asn Asp Leu Trp Asp Trp Ile Asn Lys
1               5                   10                  15

<210> SEQ ID NO 198
<211> LENGTH: 15
<212> TYPE: PRT
<213> ORGANISM: Homo sapiens

<400> SEQUENCE: 198

Ile His Val Thr Ile Pro Gln Asp Leu Trp Asp Trp Ile Asn Lys
1               5                   10                  15

<210> SEQ ID NO 199
<211> LENGTH: 15
<212> TYPE: PRT
<213> ORGANISM: Homo sapiens

<400> SEQUENCE: 199

Ile His Val Thr Ile Pro Ala Gln Leu Trp Asp Trp Ile Asn Lys
1               5                   10                  15
```

```
<210> SEQ ID NO 200
<211> LENGTH: 15
<212> TYPE: PRT
<213> ORGANISM: Homo sapiens

<400> SEQUENCE: 200

Ile His Val Thr Ile Pro Ala Tyr Leu Trp Asp Trp Ile Asn Lys
1               5                   10                  15

<210> SEQ ID NO 201
<211> LENGTH: 15
<212> TYPE: PRT
<213> ORGANISM: Homo sapiens

<400> SEQUENCE: 201

Ile His Val Thr Ile Pro Ala Asp Ala Trp Asp Trp Ile Asn Lys
1               5                   10                  15

<210> SEQ ID NO 202
<211> LENGTH: 15
<212> TYPE: PRT
<213> ORGANISM: Homo sapiens

<400> SEQUENCE: 202

Ile His Val Thr Ile Pro Ala Asp Gly Trp Asp Trp Ile Asn Lys
1               5                   10                  15

<210> SEQ ID NO 203
<211> LENGTH: 15
<212> TYPE: PRT
<213> ORGANISM: Homo sapiens

<400> SEQUENCE: 203

Ile His Val Thr Ile Pro Ala Asp Pro Trp Asp Trp Ile Asn Lys
1               5                   10                  15

<210> SEQ ID NO 204
<211> LENGTH: 15
<212> TYPE: PRT
<213> ORGANISM: Homo sapiens

<400> SEQUENCE: 204

Ile His Val Thr Ile Pro Ala Asp Val Trp Asp Trp Ile Asn Lys
1               5                   10                  15

<210> SEQ ID NO 205
<211> LENGTH: 15
<212> TYPE: PRT
<213> ORGANISM: Homo sapiens

<400> SEQUENCE: 205

Ile His Val Thr Ile Pro Ala Asp Ile Trp Asp Trp Ile Asn Lys
1               5                   10                  15

<210> SEQ ID NO 206
<211> LENGTH: 15
<212> TYPE: PRT
<213> ORGANISM: Homo sapiens

<400> SEQUENCE: 206

Ile His Val Thr Ile Pro Ala Asp Leu His Asp Trp Ile Asn Lys
1               5                   10                  15

<210> SEQ ID NO 207
<211> LENGTH: 15
```

<212> TYPE: PRT
<213> ORGANISM: Homo sapiens

<400> SEQUENCE: 207

Ile His Val Thr Ile Pro Ala Asp Leu Phe Asp Trp Ile Asn Lys
1               5                   10                  15

<210> SEQ ID NO 208
<211> LENGTH: 15
<212> TYPE: PRT
<213> ORGANISM: Homo sapiens

<400> SEQUENCE: 208

Ile His Val Thr Ile Pro Ala Asp Leu Trp Asn Trp Ile Asn Lys
1               5                   10                  15

<210> SEQ ID NO 209
<211> LENGTH: 15
<212> TYPE: PRT
<213> ORGANISM: Homo sapiens

<400> SEQUENCE: 209

Ile His Val Thr Ile Pro Ala Asp Leu Trp Asp His Ile Asn Lys
1               5                   10                  15

<210> SEQ ID NO 210
<211> LENGTH: 15
<212> TYPE: PRT
<213> ORGANISM: Homo sapiens

<400> SEQUENCE: 210

Ile His Val Thr Ile Pro Ala Asp Leu Trp Asp Phe Ile Asn Lys
1               5                   10                  15

<210> SEQ ID NO 211
<211> LENGTH: 15
<212> TYPE: PRT
<213> ORGANISM: Homo sapiens

<400> SEQUENCE: 211

Ile His Val Thr Ile Pro Ala Asp Leu Trp Asp Tyr Ile Asn Lys
1               5                   10                  15

<210> SEQ ID NO 212
<211> LENGTH: 15
<212> TYPE: PRT
<213> ORGANISM: Homo sapiens

<400> SEQUENCE: 212

Ile His Val Thr Ile Pro Ala Asp Leu Trp Asp Trp Glu Asn Lys
1               5                   10                  15

<210> SEQ ID NO 213
<211> LENGTH: 15
<212> TYPE: PRT
<213> ORGANISM: Homo sapiens

<400> SEQUENCE: 213

Ile His Val Thr Ile Pro Ala Asp Leu Trp Asp Trp Lys Asn Lys
1               5                   10                  15

<210> SEQ ID NO 214
<211> LENGTH: 15
<212> TYPE: PRT
<213> ORGANISM: Homo sapiens

<400> SEQUENCE: 214

Ile His Val Thr Ile Pro Ala Asp Leu Trp Asp Trp Ala Asn Lys
1               5                   10                  15

<210> SEQ ID NO 215
<211> LENGTH: 15
<212> TYPE: PRT
<213> ORGANISM: Homo sapiens

<400> SEQUENCE: 215

Ile His Val Thr Ile Pro Ala Asp Leu Trp Asp Trp Gly Asn Lys
1               5                   10                  15

<210> SEQ ID NO 216
<211> LENGTH: 15
<212> TYPE: PRT
<213> ORGANISM: Homo sapiens

<400> SEQUENCE: 216

Ile His Val Thr Ile Pro Ala Asp Leu Trp Asp Trp Leu Asn Lys
1               5                   10                  15

<210> SEQ ID NO 217
<211> LENGTH: 15
<212> TYPE: PRT
<213> ORGANISM: Homo sapiens

<400> SEQUENCE: 217

Ile His Val Thr Ile Pro Ala Asp Leu Trp Asp Trp Pro Asn Lys
1               5                   10                  15

<210> SEQ ID NO 218
<211> LENGTH: 15
<212> TYPE: PRT
<213> ORGANISM: Homo sapiens

<400> SEQUENCE: 218

Ile His Val Thr Ile Pro Ala Asp Leu Trp Asp Trp Phe Asn Lys
1               5                   10                  15

<210> SEQ ID NO 219
<211> LENGTH: 15
<212> TYPE: PRT
<213> ORGANISM: Homo sapiens

<400> SEQUENCE: 219

Ile His Val Thr Ile Pro Ala Asp Leu Trp Asp Trp Tyr Asn Lys
1               5                   10                  15

<210> SEQ ID NO 220
<211> LENGTH: 15
<212> TYPE: PRT
<213> ORGANISM: Homo sapiens

<400> SEQUENCE: 220

Ile His Val Thr Ile Pro Ala Asp Leu Trp Asp Trp Ile Gln Lys
1               5                   10                  15

<210> SEQ ID NO 221
<211> LENGTH: 15
<212> TYPE: PRT
<213> ORGANISM: Homo sapiens

<400> SEQUENCE: 221

```
Ile His Val Thr Ile Pro Ala Asp Leu Trp Asp Trp Ile Asp Lys
1               5                   10                  15

<210> SEQ ID NO 222
<211> LENGTH: 15
<212> TYPE: PRT
<213> ORGANISM: Homo sapiens

<400> SEQUENCE: 222

Ile His Val Thr Ile Pro Ala Asp Leu Trp Asp Trp Ile Asn His
1               5                   10                  15

<210> SEQ ID NO 223
<211> LENGTH: 15
<212> TYPE: PRT
<213> ORGANISM: Homo sapiens

<400> SEQUENCE: 223

Ile His Val Thr Ile Pro Ala Asp Leu Trp Asp Trp Ile Asn Asp
1               5                   10                  15

<210> SEQ ID NO 224
<211> LENGTH: 15
<212> TYPE: PRT
<213> ORGANISM: Homo sapiens

<400> SEQUENCE: 224

Val His Val Thr Val Pro Gln Glu Leu Trp Glu Trp Val Arg Arg
1               5                   10                  15

<210> SEQ ID NO 225
<211> LENGTH: 15
<212> TYPE: PRT
<213> ORGANISM: Homo sapiens

<400> SEQUENCE: 225

Val His Val Thr Val Pro Gln Glu Leu Phe Glu Trp Val Arg Arg
1               5                   10                  15

<210> SEQ ID NO 226
<211> LENGTH: 15
<212> TYPE: PRT
<213> ORGANISM: Homo sapiens

<400> SEQUENCE: 226

Val His Val Thr Val Pro Gln Glu Leu Tyr Glu Trp Val Arg Arg
1               5                   10                  15

<210> SEQ ID NO 227
<211> LENGTH: 15
<212> TYPE: PRT
<213> ORGANISM: Homo sapiens

<400> SEQUENCE: 227

Val His Val Thr Val Pro Gln Glu Leu Trp Glu Trp Val Glu Glu
1               5                   10                  15

<210> SEQ ID NO 228
<211> LENGTH: 15
<212> TYPE: PRT
<213> ORGANISM: Homo sapiens

<400> SEQUENCE: 228

Val His Val Thr Val Pro Gln Glu Leu Phe Glu Trp Val Glu Glu
```

```
                1               5              10              15
```

<210> SEQ ID NO 229
<211> LENGTH: 15
<212> TYPE: PRT
<213> ORGANISM: Homo sapiens

<400> SEQUENCE: 229

```
Val His Val Thr Val Pro Gln Glu Leu Tyr Glu Trp Val Glu Glu
 1               5                  10                  15
```

<210> SEQ ID NO 230
<211> LENGTH: 15
<212> TYPE: PRT
<213> ORGANISM: Homo sapiens

<400> SEQUENCE: 230

```
Val His Val Ser Ile Pro Gln Glu Leu Trp Glu Trp Val Arg Arg
 1               5                  10                  15
```

<210> SEQ ID NO 231
<211> LENGTH: 15
<212> TYPE: PRT
<213> ORGANISM: Homo sapiens

<400> SEQUENCE: 231

```
Val His Val Ser Val Pro Gln Glu Leu Trp Glu Trp Val Arg Arg
 1               5                  10                  15
```

<210> SEQ ID NO 232
<211> LENGTH: 15
<212> TYPE: PRT
<213> ORGANISM: Homo sapiens

<400> SEQUENCE: 232

```
Val His Val Ser Val Pro Gln Glu Leu Tyr Glu Trp Val Arg Arg
 1               5                  10                  15
```

<210> SEQ ID NO 233
<211> LENGTH: 15
<212> TYPE: PRT
<213> ORGANISM: Homo sapiens

<400> SEQUENCE: 233

```
Val Arg Val Thr Ile Pro Gln Glu Leu Trp Glu Trp Val Arg Arg
 1               5                  10                  15
```

<210> SEQ ID NO 234
<211> LENGTH: 15
<212> TYPE: PRT
<213> ORGANISM: Homo sapiens

<400> SEQUENCE: 234

```
Val Arg Val Thr Val Pro Gln Glu Leu Tyr Glu Trp Val Arg Arg
 1               5                  10                  15
```

<210> SEQ ID NO 235
<211> LENGTH: 15
<212> TYPE: PRT
<213> ORGANISM: Homo sapiens

<400> SEQUENCE: 235

```
Val Arg Val Thr Val Pro Gln Glu Leu Trp Glu Trp Val Arg Arg
 1               5                  10                  15
```

```
<210> SEQ ID NO 236
<211> LENGTH: 15
<212> TYPE: PRT
<213> ORGANISM: Homo sapiens

<400> SEQUENCE: 236

Val His Val Thr Val Pro Gln Glu Ile Tyr Glu Trp Val Arg Arg
1               5                   10                  15

<210> SEQ ID NO 237
<211> LENGTH: 15
<212> TYPE: PRT
<213> ORGANISM: Homo sapiens

<400> SEQUENCE: 237

Val His Val Thr Ile Pro Gln Glu Ile Trp Glu Trp Val Arg Arg
1               5                   10                  15

<210> SEQ ID NO 238
<211> LENGTH: 15
<212> TYPE: PRT
<213> ORGANISM: Homo sapiens

<400> SEQUENCE: 238

Val His Phe Thr Val Pro Gln Glu Leu Tyr Glu Trp Val Arg Arg
1               5                   10                  15

<210> SEQ ID NO 239
<211> LENGTH: 15
<212> TYPE: PRT
<213> ORGANISM: Homo sapiens

<400> SEQUENCE: 239

Val Lys Ile Ser Val Pro Ala Asp Leu Trp Asp Trp Ile Asn Lys
1               5                   10                  15

<210> SEQ ID NO 240
<211> LENGTH: 15
<212> TYPE: PRT
<213> ORGANISM: Homo sapiens

<400> SEQUENCE: 240

Leu Arg Ile Ser Val Pro Ala Asp Leu Trp Asp Trp Ile Asn Lys
1               5                   10                  15

<210> SEQ ID NO 241
<211> LENGTH: 15
<212> TYPE: PRT
<213> ORGANISM: Homo sapiens

<400> SEQUENCE: 241

Leu Arg Ile Tyr Val Pro Ala Asp Leu Trp Asp Trp Ile Asn Lys
1               5                   10                  15

<210> SEQ ID NO 242
<211> LENGTH: 15
<212> TYPE: PRT
<213> ORGANISM: Homo sapiens

<400> SEQUENCE: 242

Val Arg Gly Tyr Val Pro Ala Asp Leu Trp Asp Trp Ile Asn Lys
1               5                   10                  15

<210> SEQ ID NO 243
```

<211> LENGTH: 15
<212> TYPE: PRT
<213> ORGANISM: Homo sapiens

<400> SEQUENCE: 243

Val Arg Ala Tyr Val Pro Ala Asp Leu Trp Asp Trp Ile Asn Lys
1               5                   10                  15

<210> SEQ ID NO 244
<211> LENGTH: 15
<212> TYPE: PRT
<213> ORGANISM: Homo sapiens

<400> SEQUENCE: 244

Val Arg Leu Tyr Val Pro Ala Asp Leu Trp Asp Trp Ile Asn Lys
1               5                   10                  15

<210> SEQ ID NO 245
<211> LENGTH: 15
<212> TYPE: PRT
<213> ORGANISM: Homo sapiens

<400> SEQUENCE: 245

Val Arg Ile Tyr Leu Pro Ala Asp Leu Trp Asp Trp Ile Asn Lys
1               5                   10                  15

<210> SEQ ID NO 246
<211> LENGTH: 15
<212> TYPE: PRT
<213> ORGANISM: Homo sapiens

<400> SEQUENCE: 246

Ile His Val Thr Ile Pro Leu Glu Ile Phe Glu Trp Leu Gln His
1               5                   10                  15

<210> SEQ ID NO 247
<211> LENGTH: 15
<212> TYPE: PRT
<213> ORGANISM: Homo sapiens

<400> SEQUENCE: 247

Ile His Val Thr Ile Pro Leu Glu Ile Phe Glu Trp Ala Gln His
1               5                   10                  15

<210> SEQ ID NO 248
<211> LENGTH: 15
<212> TYPE: PRT
<213> ORGANISM: Homo sapiens

<400> SEQUENCE: 248

Ile His Val Thr Ile Pro Leu Glu Ile Phe Glu Trp Leu Gln Arg
1               5                   10                  15

<210> SEQ ID NO 249
<211> LENGTH: 15
<212> TYPE: PRT
<213> ORGANISM: Homo sapiens

<400> SEQUENCE: 249

Ile His Val Thr Ile Pro Leu Glu Val Phe Glu Trp Leu Gln His
1               5                   10                  15

<210> SEQ ID NO 250
<211> LENGTH: 15
<212> TYPE: PRT

<213> ORGANISM: Homo sapiens

<400> SEQUENCE: 250

Ile His Val Thr Ile Pro Gly Glu Ile Phe Glu Trp Leu Gln His
1               5                   10                  15

<210> SEQ ID NO 251
<211> LENGTH: 15
<212> TYPE: PRT
<213> ORGANISM: Homo sapiens

<400> SEQUENCE: 251

Val Arg Phe Ser Val Pro Gln Glu Ile Tyr Glu Trp Val Arg Arg
1               5                   10                  15

<210> SEQ ID NO 252
<211> LENGTH: 15
<212> TYPE: PRT
<213> ORGANISM: Homo sapiens

<400> SEQUENCE: 252

Leu Arg Ile Ser Val Pro Leu Glu Ile Phe Glu Trp Leu Gln His
1               5                   10                  15

<210> SEQ ID NO 253
<211> LENGTH: 15
<212> TYPE: PRT
<213> ORGANISM: Homo sapiens

<400> SEQUENCE: 253

Leu Arg Gly Ser Val Pro Leu Glu Ile Phe Glu Trp Leu Gln His
1               5                   10                  15

<210> SEQ ID NO 254
<211> LENGTH: 15
<212> TYPE: PRT
<213> ORGANISM: Homo sapiens

<400> SEQUENCE: 254

Val Lys Ile Ser Val Pro Leu Glu Ile Phe Glu Trp Leu Gln His
1               5                   10                  15

<210> SEQ ID NO 255
<211> LENGTH: 15
<212> TYPE: PRT
<213> ORGANISM: Homo sapiens

<400> SEQUENCE: 255

Val Glu Phe Asn Phe Pro Gln Gln Val Tyr Glu Trp Phe Asp Asp
1               5                   10                  15

<210> SEQ ID NO 256
<211> LENGTH: 15
<212> TYPE: PRT
<213> ORGANISM: Homo sapiens

<400> SEQUENCE: 256

Val Glu Phe Asn Phe Pro Gln Gln Val Tyr Glu Trp Val Arg Arg
1               5                   10                  15

<210> SEQ ID NO 257
<211> LENGTH: 15
<212> TYPE: PRT
<213> ORGANISM: Homo sapiens -continued

<400> SEQUENCE: 257

Thr Trp Tyr Val Phe Asn Glu Gln His Gln Glu Tyr Val Arg Lys
1               5                   10                  15

<210> SEQ ID NO 258
<211> LENGTH: 15
<212> TYPE: PRT
<213> ORGANISM: Artificial
<220> FEATURE:
<223> OTHER INFORMATION: Synthetic peptide sequence
<220> FEATURE:
<221> NAME/KEY: X
<222> LOCATION: (1)..(1)
<223> OTHER INFORMATION: wherein, independently from each other: X is I,
      V, D, K, W, A, G, L or P
<220> FEATURE:
<221> NAME/KEY: X
<222> LOCATION: (2)..(2)
<223> OTHER INFORMATION: X is H, M, K, N, R, E, Q, W or Y
<220> FEATURE:
<221> NAME/KEY: X
<222> LOCATION: (3)..(3)
<223> OTHER INFORMATION: X is V, F, A, G, L, P, I, Y or W
<220> FEATURE:
<221> NAME/KEY: X
<222> LOCATION: (4)..(4)
<223> OTHER INFORMATION: X is T, Q, H, S, N or Y
<220> FEATURE:
<221> NAME/KEY: X
<222> LOCATION: (5)..(5)
<223> OTHER INFORMATION: X is I, F, A, G, L, P, V or Y
<220> FEATURE:
<221> NAME/KEY: X
<222> LOCATION: (6)..(6)
<223> OTHER INFORMATION: X is P, G, A, L, V, I or N
<220> FEATURE:
<221> NAME/KEY: X
<222> LOCATION: (7)..(7)
<223> OTHER INFORMATION: X is A, Q, G, L, P, V, I, N or E
<220> FEATURE:
<221> NAME/KEY: X
<222> LOCATION: (8)..(8)
<223> OTHER INFORMATION: X is D, E, N, Q or Y
<220> FEATURE:
<221> NAME/KEY: X
<222> LOCATION: (9)..(9)
<223> OTHER INFORMATION: X is L, V, F, W, A, G, P, I or H
<220> FEATURE:
<221> NAME/KEY: X
<222> LOCATION: (10)..(10)
<223> OTHER INFORMATION: X is W, Y, F or Q or it is absent
<220> FEATURE:
<221> NAME/KEY: X
<222> LOCATION: (11)..(11)
<223> OTHER INFORMATION: X is D, E or N or it is absent
<220> FEATURE:
<221> NAME/KEY: X
<222> LOCATION: (12)..(12)
<223> OTHER INFORMATION: X is W, F, V, H or Y or it is absent
<220> FEATURE:
<221> NAME/KEY: X
<222> LOCATION: (13)..(13)
<223> OTHER INFORMATION: X is I, V, F, E, K, A, G, L, P or Y or it is
      absent
<220> FEATURE:
<221> NAME/KEY: X
<222> LOCATION: (14)..(14)
<223> OTHER INFORMATION: X is N, R, E, F, Q or D or it is absent
<220> FEATURE:
<221> NAME/KEY: X
<222> LOCATION: (15)..(15)
<223> OTHER INFORMATION: is K, R, E, F, V, W, H or D or it is absent

<400> SEQUENCE: 258

Xaa Xaa Xaa Xaa Xaa Xaa Xaa Xaa Xaa Xaa Xaa Xaa Xaa Xaa Xaa
1               5                   10                  15

<210> SEQ ID NO 259
<211> LENGTH: 13
<212> TYPE: PRT
<213> ORGANISM: Artificial
<220> FEATURE:
<223> OTHER INFORMATION: Synthetic peptide sequence

<400> SEQUENCE: 259

His Val Thr Ile Pro Ala Asp Leu Trp Asp Trp Ile Asn
1               5                   10

<210> SEQ ID NO 260
<211> LENGTH: 13
<212> TYPE: PRT
<213> ORGANISM: Artificial
<220> FEATURE:
<223> OTHER INFORMATION: Synthetic peptide sequence

<400> SEQUENCE: 260

Ile His Val Thr Ile Pro Ala Asp Leu Trp Asp Trp Ile
1               5                   10

<210> SEQ ID NO 261
<211> LENGTH: 12
<212> TYPE: PRT
<213> ORGANISM: Artificial
<220> FEATURE:
<223> OTHER INFORMATION: Synthetic peptide sequence

<400> SEQUENCE: 261

Ile His Val Thr Ile Pro Ala Asp Leu Trp Asp Trp
1               5                   10

<210> SEQ ID NO 262
<211> LENGTH: 15
<212> TYPE: PRT
<213> ORGANISM: Artificial
<220> FEATURE:
<223> OTHER INFORMATION: Synthetic peptide sequence

<400> SEQUENCE: 262

Lys His Val Thr Ile Pro Ala Asp Leu Trp Asp Trp Ile Asn Lys
1               5                   10                  15

<210> SEQ ID NO 263
<211> LENGTH: 15
<212> TYPE: PRT
<213> ORGANISM: Artificial
<220> FEATURE:
<223> OTHER INFORMATION: Synthetic peptide sequence

<400> SEQUENCE: 263

Val His Val Thr Ile Pro Asn Glu Leu Trp Glu Trp Val Arg Arg
1               5                   10                  15

<210> SEQ ID NO 264
<211> LENGTH: 16
<212> TYPE: PRT
<213> ORGANISM: Artificial
<220> FEATURE:
<223> OTHER INFORMATION: Synthetic peptide sequence
<220> FEATURE:
<221> NAME/KEY: Y
<222> LOCATION: (1)..(1)
<223> OTHER INFORMATION: wherein: Y is A, T, V, K, R, I, L, X, or G
<220> FEATURE:
<221> NAME/KEY: Y

```
<222> LOCATION: (2)..(2)
<223> OTHER INFORMATION: Y is R, W, P, E, Q, or A
<220> FEATURE:
<221> NAME/KEY: Y
<222> LOCATION: (3)..(3)
<223> OTHER INFORMATION: Y is K, W, G, T, I, R, or P
<220> FEATURE:
<221> NAME/KEY: Y
<222> LOCATION: (4)..(4)
<223> OTHER INFORMATION: Y is K, T, E, W, A, R, D, G, X, or F
<220> FEATURE:
<221> NAME/KEY: Y
<222> LOCATION: (5)..(5)
<223> OTHER INFORMATION: Y is A, E, T, G, W, I, R, P, or V
<220> FEATURE:
<221> NAME/KEY: Y
<222> LOCATION: (6)..(6)
<223> OTHER INFORMATION: Y is A, W, E, R, G, P, or absent
<220> FEATURE:
<221> NAME/KEY: Y
<222> LOCATION: (7)..(7)
<223> OTHER INFORMATION: Y is K, S, W, T, F, R, V, G, or absent
<220> FEATURE:
<221> NAME/KEY: Y
<222> LOCATION: (8)..(8)
<223> OTHER INFORMATION: Y is A, Q, W, R, G, or absent
<220> FEATURE:
<221> NAME/KEY: Y
<222> LOCATION: (9)..(9)
<223> OTHER INFORMATION: Y is N, G or absent
<220> FEATURE:
<221> NAME/KEY: Y
<222> LOCATION: (10)..(10)
<223> OTHER INFORMATION: Y is R or absent
<220> FEATURE:
<221> NAME/KEY: Y
<222> LOCATION: (11)..(11)
<223> OTHER INFORMATION: Y is R or absent
<220> FEATURE:
<221> NAME/KEY: Y
<222> LOCATION: (12)..(12)
<223> OTHER INFORMATION: Y is M or absent
<220> FEATURE:
<221> NAME/KEY: Y
<222> LOCATION: (13)..(13)
<223> OTHER INFORMATION: Y is K or absent
<220> FEATURE:
<221> NAME/KEY: Y
<222> LOCATION: (14)..(14)
<223> OTHER INFORMATION: Y is W or absent
<220> FEATURE:
<221> NAME/KEY: Y
<222> LOCATION: (15)..(15)
<223> OTHER INFORMATION: Y is K or absent
<220> FEATURE:
<221> NAME/KEY: Y
<222> LOCATION: (16)..(16)
<223> OTHER INFORMATION: Y is K or absent

<400> SEQUENCE: 264

Tyr Tyr Tyr Tyr Tyr Tyr Tyr Tyr Tyr Tyr Tyr Tyr Tyr Tyr Tyr Tyr
1               5                   10                  15

<210> SEQ ID NO 265
<211> LENGTH: 6
<212> TYPE: PRT
<213> ORGANISM: Artificial
<220> FEATURE:
<223> OTHER INFORMATION: Synthetic peptide sequence

<400> SEQUENCE: 265

Arg Arg Arg Arg Arg Arg
1               5

<210> SEQ ID NO 266
```

```
<211> LENGTH: 15
<212> TYPE: PRT
<213> ORGANISM: Artificial
<220> FEATURE:
<223> OTHER INFORMATION: Synthetic peptide sequence

<400> SEQUENCE: 266

Ile His Val Thr Ile Pro Ala Asp Leu Trp Glu Trp Ile Glu Lys
1               5                   10                  15

<210> SEQ ID NO 267
<211> LENGTH: 15
<212> TYPE: PRT
<213> ORGANISM: Artificial
<220> FEATURE:
<223> OTHER INFORMATION: Synthetic peptide sequence

<400> SEQUENCE: 267

Ile His Val Thr Ile Pro Ala Asp Leu Trp Glu Trp Ile Asn Glu
1               5                   10                  15

<210> SEQ ID NO 268
<211> LENGTH: 15
<212> TYPE: PRT
<213> ORGANISM: Artificial
<220> FEATURE:
<223> OTHER INFORMATION: Synthetic peptide sequence

<400> SEQUENCE: 268

Ile His Val Thr Ile Pro Ala Asp Leu Trp Asp Trp Ile Glu Lys
1               5                   10                  15

<210> SEQ ID NO 269
<211> LENGTH: 15
<212> TYPE: PRT
<213> ORGANISM: Artificial
<220> FEATURE:
<223> OTHER INFORMATION: Synthetic peptide sequence

<400> SEQUENCE: 269

Val His Val Thr Ile Pro Ala Asp Leu Trp Glu Trp Ile Glu Lys
1               5                   10                  15

<210> SEQ ID NO 270
<211> LENGTH: 15
<212> TYPE: PRT
<213> ORGANISM: Artificial
<220> FEATURE:
<223> OTHER INFORMATION: Synthetic peptide sequence

<400> SEQUENCE: 270

Val His Val Thr Ile Pro Ala Asp Leu Trp Glu Trp Ile Asn Glu
1               5                   10                  15

<210> SEQ ID NO 271
<211> LENGTH: 15
<212> TYPE: PRT
<213> ORGANISM: Artificial
<220> FEATURE:
<223> OTHER INFORMATION: Synthetic peptide sequence

<400> SEQUENCE: 271

Val His Val Thr Ile Pro Ala Asp Leu Trp Glu Trp Ile Asn Lys
1               5                   10                  15

<210> SEQ ID NO 272
<211> LENGTH: 15
```

```
<212> TYPE: PRT
<213> ORGANISM: Artificial
<220> FEATURE:
<223> OTHER INFORMATION: Synthetic peptide sequence

<400> SEQUENCE: 272

Ile His Val Thr Ile Pro Ala Asp Leu Trp Glu Trp Ile Asn Lys
1               5                   10                  15

<210> SEQ ID NO 273
<211> LENGTH: 15
<212> TYPE: PRT
<213> ORGANISM: Artificial
<220> FEATURE:
<223> OTHER INFORMATION: Synthetic peptide sequence

<400> SEQUENCE: 273

Val His Val Thr Ile Pro Ala Asp Leu Trp Asp Trp Ile Asn Glu
1               5                   10                  15

<210> SEQ ID NO 274
<211> LENGTH: 15
<212> TYPE: PRT
<213> ORGANISM: Artificial
<220> FEATURE:
<223> OTHER INFORMATION: Synthetic peptide sequence

<400> SEQUENCE: 274

Val His Val Thr Ile Pro Ala Asp Leu Trp Asp Trp Ile Glu Lys
1               5                   10                  15
```

UNITED STATES PATENT AND TRADEMARK OFFICE
CERTIFICATE OF CORRECTION

| | | |
|---|---|---|
| PATENT NO. | : 12,358,950 B2 | Page 1 of 1 |
| APPLICATION NO. | : 17/555154 | |
| DATED | : July 15, 2025 | |
| INVENTOR(S) | : Marcello Allegretti et al. | |

It is certified that error appears in the above-identified patent and that said Letters Patent is hereby corrected as shown below:

In the Claims

Claim 3, Column 127, Line 22, delete "(1)" and insert -- (l) --.

Claim 8, Column 128, Line 24, delete "capronic" and insert -- caproic --.

Signed and Sealed this
Twenty-eighth Day of October, 2025

John A. Squires
*Director of the United States Patent and Trademark Office*